United States Patent
Xi et al.

(10) Patent No.: US 10,640,515 B2
(45) Date of Patent: May 5, 2020

(54) HEPATITIS C VIRUS INHIBITOR AND USES THEREOF

(71) Applicant: ZHEJIANG PALO ALTO PHARMACEUTICALS,INC, Quzhou, Zhejiang (CN)

(72) Inventors: Zhijian Xi, Zhejiang (CN); Huaqiang Xu, Zhejiang (CN); Chunping Lu, Zhejiang (CN)

(73) Assignee: ZHEJIANG PALO ALTO PHARMACEUTICALS, INC, Quzhou (CN)

( * ) Notice: Subject to any disclaimer, the term of this patent is extended or adjusted under 35 U.S.C. 154(b) by 0 days.

(21) Appl. No.: 16/231,265

(22) Filed: Dec. 21, 2018

(65) Prior Publication Data

US 2019/0135828 A1    May 9, 2019

Related U.S. Application Data

(63) Continuation of application No. PCT/CN2017/085152, filed on May 19, 2017.

(30) Foreign Application Priority Data

Jun. 21, 2016 (CN) .......................... 2016 1 0460768

(51) Int. Cl.
   *C07D 498/04* (2006.01)
   *A61P 31/14* (2006.01)
   *A61K 38/05* (2006.01)

(52) U.S. Cl.
   CPC ............ *C07D 498/04* (2013.01); *A61K 38/05* (2013.01); *A61P 31/14* (2018.01)

(58) Field of Classification Search
   CPC ........ A61K 38/05; A61P 31/14; C07D 498/04
   See application file for complete search history.

(56) References Cited

FOREIGN PATENT DOCUMENTS

| CN | 102427729 A | 4/2012 |
| CN | 103459399 A | 12/2013 |
| WO | 2015065817 A1 | 5/2015 |
| WO | 2015065821 A1 | 5/2015 |
| WO | 2015124063 A1 | 8/2015 |

*Primary Examiner* — Valerie Rodriguez-Garcia
(74) *Attorney, Agent, or Firm* — Wayne & Ken, LLC; Tony Hom

(57) ABSTRACT

Disclosed is a compound of formula (I-a) as an inhibitor of hepatitis C virus (HCV), or an optical isomer, a pharmaceutically acceptable salt, a hydrate or a solvate thereof, usable to treat HCV infections or hepatitis C diseases and also usable as an inhibitor of HCV non-structural protein 5A (NS5A)

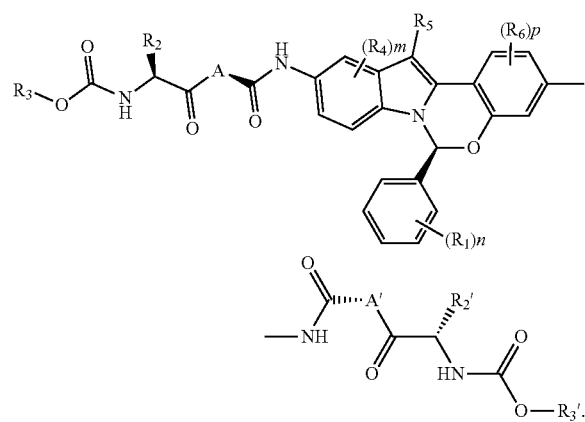

In the formula (I-a), A and A' are independently

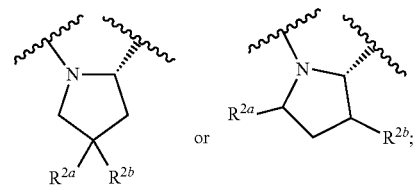

each $R_1$, $R_4$ and $R_6$ are independently selected from the group consisting of fluorine, chlorine, bromine and iodine; $R_2$ and $R_2'$ are independently selected from substituted or unsubstituted $C_1$-$C_6$ alkyl; $R_3$ and $R_3'$ are independently selected from substituted or unsubstituted $C_1$-$C_6$ alkyl; $R_5$ is selected from the group consisting of hydrogen, fluorine, chlorine, bromine and iodine; n is 2, 3, 4 or 5; m is 0, 1, 2 or 3; and p is 0, 1, 2 or 3.

7 Claims, No Drawings

HEPATITIS C VIRUS INHIBITOR AND USES THEREOF

CROSS-REFERENCE TO RELATED APPLICATIONS

This application is a continuation of International Patent Application No. PCT/CN2017/085152, filed on May 19, 2017 which claims the benefit of priority from Chinese Application No. 201610460768.6, filed on Jun. 21, 2016. The contents of the aforementioned applications, including any intervening amendments thereto, are incorporated herein by reference.

TECHNICAL FIELD

The present invention relates to pharmaceuticals, and more specifically to a hepatitis C virus (HCV) inhibitor and uses thereof.

BACKGROUND OF THE INVENTION

Hepatitis C virus (HCV) is a main human pathogen and there are about 200 million cases infected with HCV worldwide. Chronic HCV infection will develop advanced progressive liver diseases, including cirrhosis and hepatocellular carcinoma. Therefore, chronic HCV infection is one of the major causes of death worldwide in patients who suffer from liver diseases. According to data released by the Health Planning Commission, the reported cases of hepatitis C virus (HCV) infection in China has increased year by year in the past 10 years, and the general situation tends to be negative.

HCV is a positive-strand RNA virus, and its genome consists of approximately 9,600 nucleotides, including non-coding regions at both ends, i.e., an internal ribosome entry site (IRES) and an open reading frame (ORF). HCV genome comprises 10 genes that are expressed to produce a total of 10 structural proteins (a core protein, envelope proteins E1 and E2, an ion channel protein P7) and non-structural proteins (NS2, NS3, NS4A, NS4B, NS5A and NS5B). NS5A is an HCV non-structural protein 5A whose function is not fully understood. Currently, it is believed that NS5A is associated with formation of viral replication complex and virus-host interaction. Therefore, NS5A is essential for the life cycle of virus and virus replication is highly sensitive to its inhibitions (inhibitors of NS5A has a strong antiviral activity in vitro).

Currently, combination therapy of α-interferon and a broad-spectrum antiviral drug ribavirin is used as a standard therapy for treating hepatitis C. For a monotherapy, the PEGylated α-interferon is superior to the unmodified α-interferon. The latest clinical results show that the therapeutic effect is significantly improved using combination of PEGylated α-interferon and ribavirin as compared to the combination of alpha-interferon and ribavirin. However, it still does not work for some patients with chronic HCV infection leading to side effects to many patients, and thus is not suitable for a long-term treatment.

Therefore, there is a need to develop a novel and effective drug for treating the chronic HCV infection.

SUMMARY

An object of the present invention is to provide a class of compounds as HCV inhibitors.

In a first aspect, the present invention provides a compound of formula (I) or an optical isomer, a pharmaceutically acceptable salt, a hydrate or a solvate thereof:

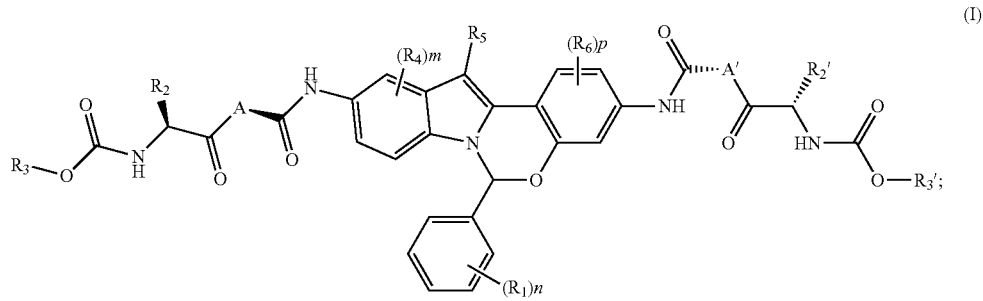

wherein A and A' are independently

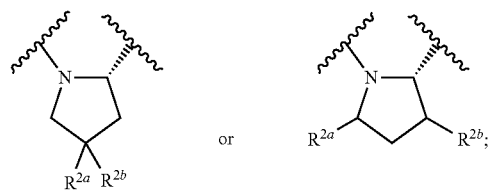

where $R^{2a}$ and $R^{2b}$ are independently selected from the group consisting of hydrogen, halogen, hydroxyl, amino, cyano group, substituted or unsubstituted $C_1$-$C_6$ alkyl, substituted or unsubstituted $C_1$-$C_6$ alkoxy and substituted or unsubstituted $C_1$-$C_6$ alkylamino; where the substituted groups comprise one or more substituents selected from the group consisting of halogen, $C_1$-$C_3$ alkyl, $C_1$-$C_3$haloalkyl, nitro, hydroxyl, amino and cyano group; or $R^{2a}$ and $R^{2b}$ are cyclized to form a $C_3$-$C_8$ cycloalkyl or a 3- to 8-membered heterocyclic group;

each $R_1$, $R_4$ and $R_6$ are independently selected from the group consisting of halogen, nitro, hydroxyl, amino, cyano group, substituted or unsubstituted $C_1$-$C_6$ alkyl, substituted or unsubstituted $C_3$-$C_8$ cycloalkyl, substituted or unsubstituted $C_1$-$C_6$ alkoxy, substituted or unsubstituted $C_1$-$C_6$ alkylamino, substituted or unsubstituted $C_1$-$C_6$ carboxyl, substituted or unsubstituted $C_1$-$C_6$ ester group, substituted or unsubstituted $C_2$-$C_6$ alkanoyl and substituted or unsubstituted $C_2$-$C_6$ alkylamide group; where substitution comprises one or more substituents selected from the group consisting of halogen, $C_1$-$C_3$ alkyl, $C_1$-$C_3$haloalkyl, nitro, hydroxyl, amino and cyano group;

n is 0, 1, 2, 3, 4 or 5;

m is 0, 1, 2 or 3;

p is 0, 1, 2 or 3:

$R_2$ and $R_2'$ are independently selected from the group consisting of hydrogen, halogen, hydroxyl, amino, cyano group, substituted or unsubstituted $C_1$-$C_6$ alkyl, substituted or unsubstituted $C_1$-$C_6$ alkoxy and substituted or unsubstituted $C_1$-$C_6$ alkylamino; where substitution comprises one or more substituents selected from the group consisting of halogen, $C_1$-$C_3$ alkyl, $C_1$-$C_3$haloalkyl, nitro, hydroxyl, amino and cyano group:

$R_3$ and $R_3'$ are independently selected from the group consisting of hydrogen, substituted or unsubstituted $C_1$-$C_6$ alkyl, substituted or unsubstituted $C_1$-$C_6$ alkoxy and substituted or unsubstituted $C_1$-$C_6$ alkylamino; where substitution comprises one or more substituents selected from the group consisting of halogen, $C_1$-$C_3$ alkyl, $C_1$-$C_3$haloalkyl, nitro, hydroxyl, amino and cyano group; and $R_5$ is selected from the group consisting of hydrogen, halogen, hydroxyl, amino, cyano group, substituted or unsubstituted $C_1$-$C_6$ alkyl, substituted or unsubstituted $C_1$-$C_3$ alkoxy and substituted or unsubstituted $C_1$-$C_6$ alkylamino; where substitution comprises one or more substituents selected from the group consisting of halogen, $C_1$-$C_3$ alkyl, $C_1$-$C_3$haloalkyl, nitro, hydroxyl, amino and cyano group.

In another preferred embodiment, n is 2, 3, 4 or 5; and at least two of $R_1$ are fluorine.

In another preferred embodiment, $R^2$ and $R^{2b}$ are independently selected from the group consisting of hydrogen, fluorine, chlorine, bromine and iodine; or $R^{2a}$ and $R^{2b}$ are cyclized together with bonded carbon atoms to form a $C_3$-$C_8$ cycloalkyl; and/or each $R_1$ is independently selected from the group consisting of fluorine, chlorine, bromine and iodine; and/or each $R_4$ is independently selected from the group consisting of fluorine, chlorine, bromine and iodine; and/or each $R_6$ is independently selected from the group consisting of fluorine, chlorine, bromine and iodine; and/or $R_2$ and $R_2'$ are independently selected from the group consisting of substituted or unsubstituted $C_1$-$C_6$ alkyl; where substitution comprises one or more substituents selected from the group consisting of halogen, $C_1$-$C_3$ alkyl, $C_1$-$C_3$haloalkyl, nitro, hydroxyl, amino and cyano group; and/or $R_3$ and $R_3'$ are independently selected from the group consisting of substituted or unsubstituted $C_1$-$C_6$ alkyl; where substitution comprises one or more substituents selected from the group consisting of halogen, $C_1$-$C_3$ alkyl, $C_1$-$C_3$haloalkyl, nitro, hydroxyl, amino and cyano group; and/or $R_5$ is selected from the group consisting of fluorine, chlorine, bromine and iodine.

In another preferred embodiment, the compound is shown as formula I-a

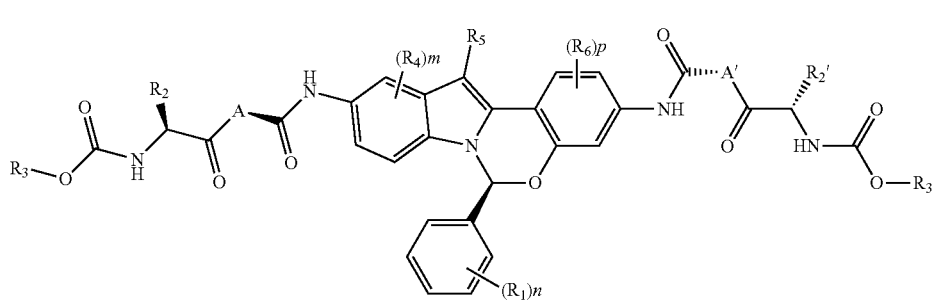

I-a wherein A, A', $R_1$, n, $R_2$, $R_2'$, $R_3$ and $R_3'$ are defined in the same manner as above.

In another preferred embodiment, the compound of formula (I) is shown as formula I-a.

In another preferred embodiment, each $R_1$ is selected from the group consisting of fluorine, hydrogen and $C_1$-$C_3$alkyl.

In another preferred embodiment, each $R_1$ is fluorine.

In another preferred embodiment, $R_2$ and $R_2'$ are independently selected from the group consisting of ethyl, n-propyl and isopropyl.

In another preferred embodiment, $R_3$ and $R_3'$ are independently methyl.

In another preferred embodiment, the compound of formula (I) is selected from:

| ID | Structure |
|---|---|
| PA6001-B | 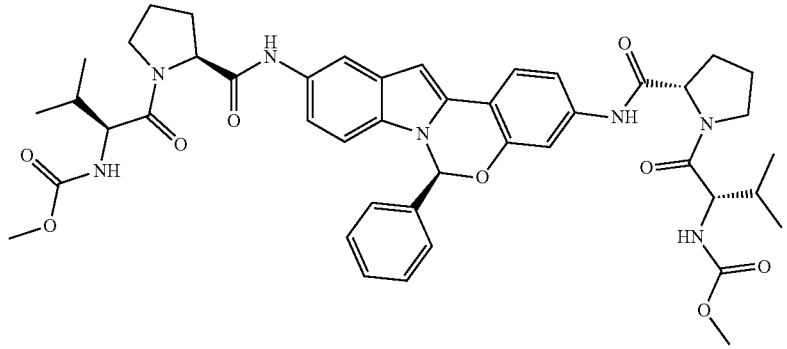 [SMILES: COC(=O)N[C@H](C(=O)N1CCC[C@H]1C(=O)Nc1ccc2c(c1)O[C@@H](c1ccccc1)n1c-2cc2cc(NC(=O)[C@@H]3CCCN3C(=O)[C@@H](NC(=O)OC)C(C)C)ccc21)C(C)C] |
| PA6016 | 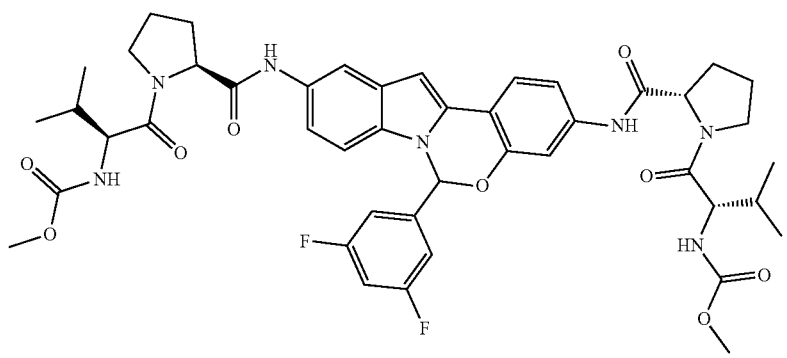 [SMILES: COC(=O)N[C@H](C(=O)N1CCC[C@H]1C(=O)Nc1ccc2c(c1)OC(c1cc(F)cc(F)c1)n1c-2cc2cc(NC(=O)[C@@H]3CCCN3C(=O)[C@@H](NC(=O)OC)C(C)C)ccc21)C(C)C] |
| PA6016-B | 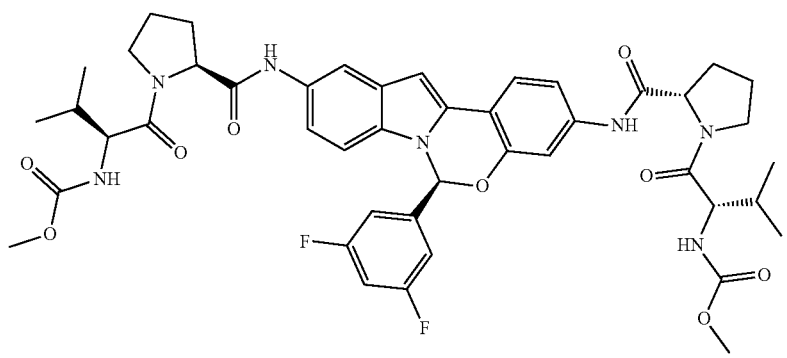 [SMILES: COC(=O)N[C@H](C(=O)N1CCC[C@H]1C(=O)Nc1ccc2c(c1)O[C@@H](c1cc(F)cc(F)c1)n1c-2cc2cc(NC(=O)[C@@H]3CCCN3C(=O)[C@@H](NC(=O)OC)C(C)C)ccc21)C(C)C] |
| PA6031 | 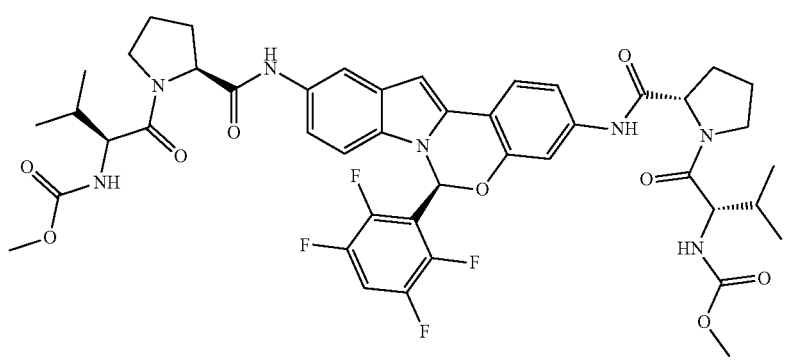 [SMILES: COC(=O)N[C@H](C(=O)N1CCC[C@H]1C(=O)Nc1ccc2c(c1)O[C@@H](c1c(F)c(F)cc(F)c1F)n1c-2cc2cc(NC(=O)[C@@H]3CCCN3C(=O)[C@@H](NC(=O)OC)C(C)C)ccc21)C(C)C] |

In a second aspect, the present invention provides a therapeutically effective amount of a pharmaceutical composition comprising the compound or an optical isomer, a pharmaceutically acceptable salt, a hydrate or a solvate thereof according to the first aspect, and a pharmaceutically acceptable auxiliary, diluent or carrier.

In another preferred embodiment, the pharmaceutical composition further comprises at least one HCV inhibitor. The HCV inhibitor inhibits HCV replication process and/or function of HCV protein.

In another preferred embodiment, the HCV inhibitor is selected from the group consisting of Sofosbuvir, PA2020, PA2029, Paritaprevir, Asunaprevir, etc.

In another preferred embodiment, the HCV replication process comprises HCV entry, HCV uncoating, HCV transcription, HCV replication, HCV assembly and/or HCV release.

In another preferred embodiment, the HCV protein is selected from the group consisting of NS2, NS3, NS4A, NS4B, NS5A and NS5B.

In a third aspect, the present invention provides use of the compound or an optical isomer, a pharmaceutically acceptable salt, a hydrate or a solvate thereof according to the first aspect of the invention, or the pharmaceutical composition according to the second aspect of the invention in the manufacture of a pharmaceutical composition for treating and/or preventing an acute or chronic disease associated with hepatitis C virus (HCV) infection.

In another preferred embodiment, the disease associated with HCV infection is an acute or chronic hepatitis C.

In another preferred embodiment, HCV is a non-structural protein 5A (NS5A) of HCV.

In a forth aspect, the present invention provides a method of preparing the compound according to the first aspect of the invention or a stereoisomer thereof, which comprises the following steps:

(a) reacting compound 1 with diphenylmethanimine in an inert solvent to form compound 2

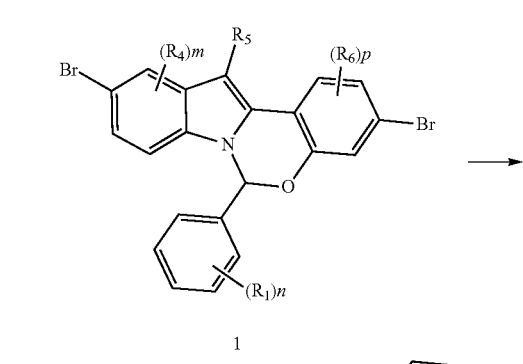

1

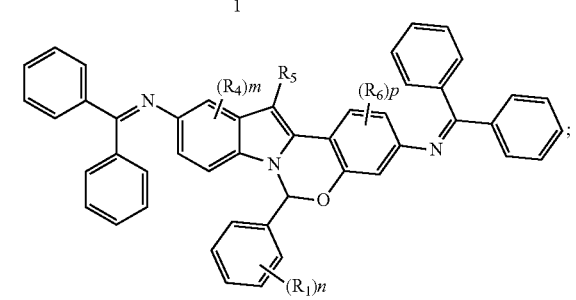

2

(b) reacting compound 2 with an acid in an inert solvent to form compound 3

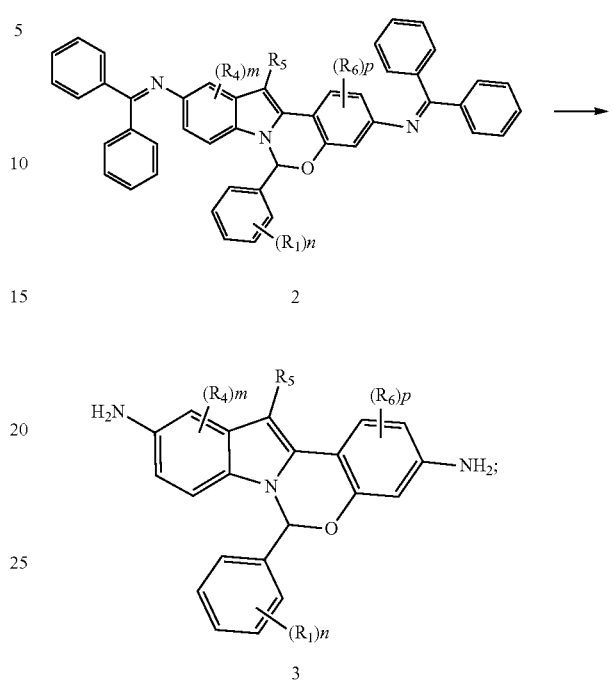

(c) reacting compound 3 with

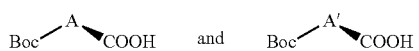

an inert solvent to form compound 4

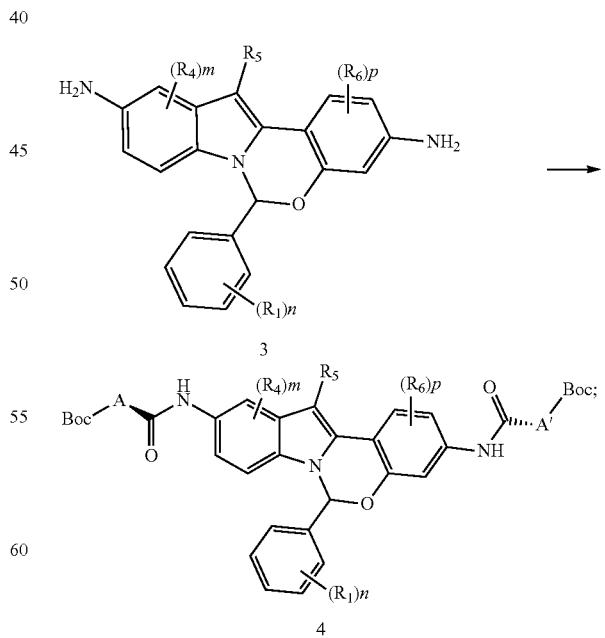

(d) reacting compound 4 with an acid in an inert solvent to form compound 5

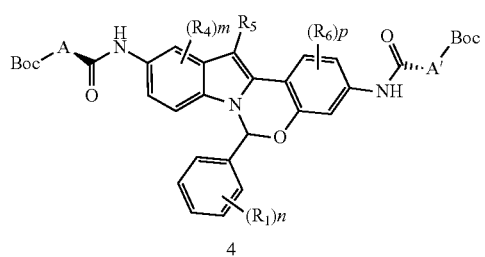

4

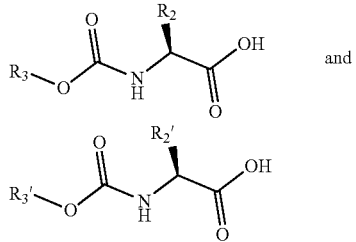

and (e) reacting compound 5 with

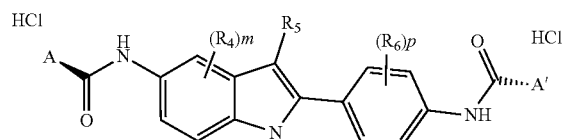

5

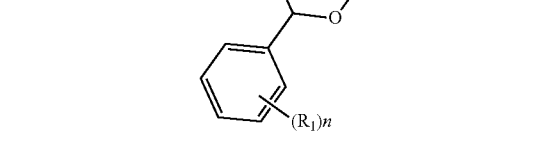

10 and in an inert solvent to form the compound of formula (I)

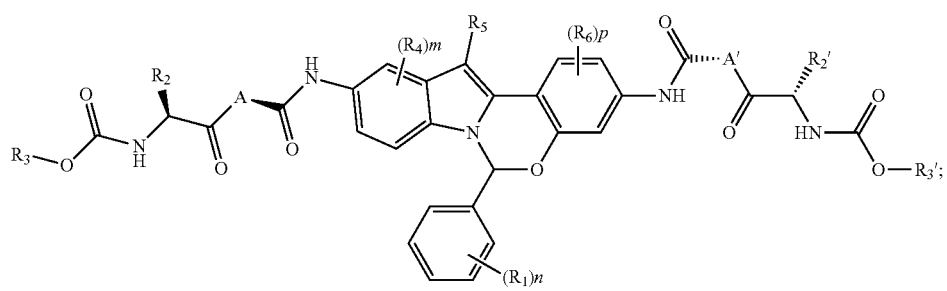

5

-continued

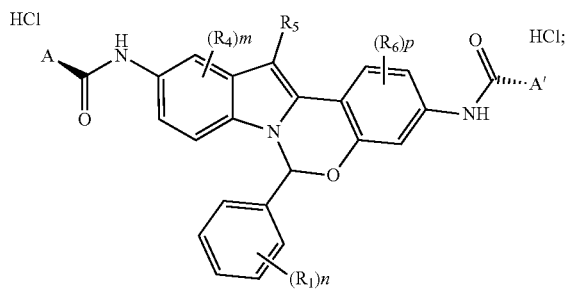

5

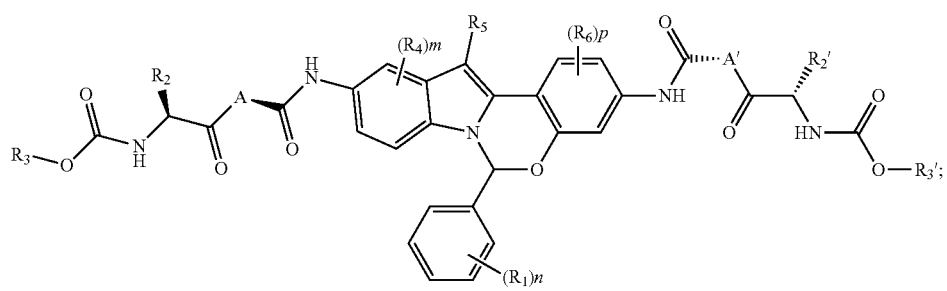

(I)

wherein A, A', $R_1$, n, $R_2$, $R_2'$, $R_3$, $R_3'$, $R_4$, m, $R_5$, $R_6$ and p are defined in the same manner as above.

In another preferred embodiment, respective stereoisomers of compound 2, 3, 4, 5 and the compound of formula (I) are obtained when compound 1 is replaced with a stereoisomer thereof.

In another preferred embodiment, a step of subjecting the compound of formula (I) to chiral resolution to form an optical isomer of the compound of formula (I) is further comprised after step (e).

In a fifth aspect, the present invention provides an intermediate of formula (2) or (3), or a stereoisomer thereof,

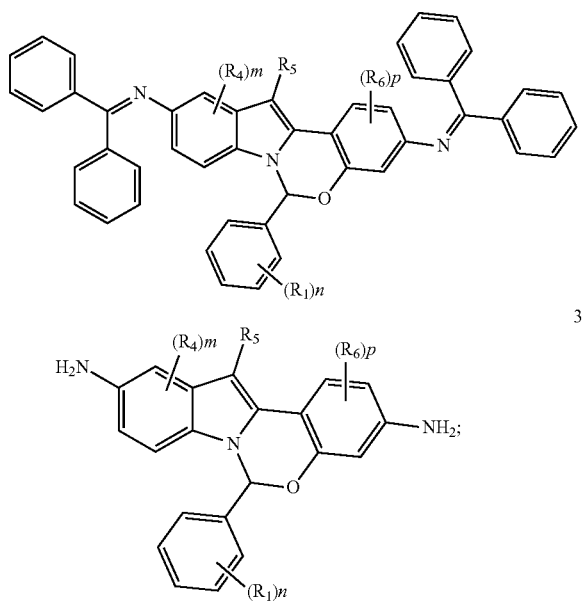

wherein $R_1$, n, $R_4$, m, $R_5$, $R_6$ and p are defined in the same manner as above.

In a sixth aspect, the present invention provides a method of preparing the compound of formula (2) or a stereoisomer thereof, which comprises the following step:

(a) reacting compound 1 with diphenylmethanimine in an inert solvent to form compound 2

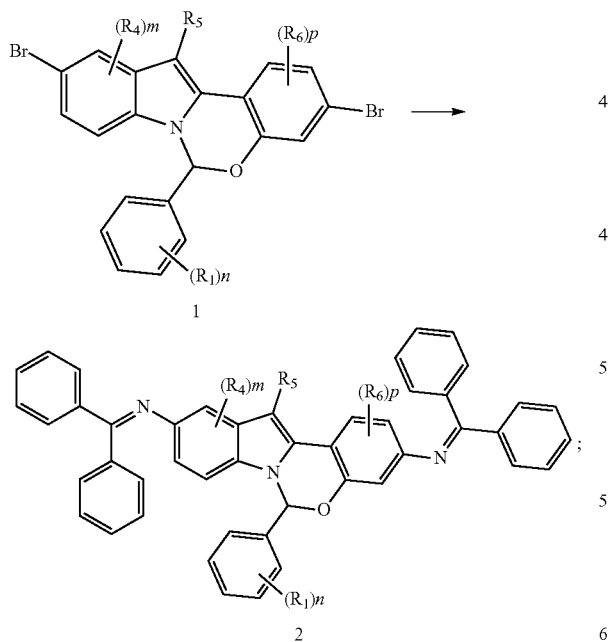

wherein, $R_1$, n, $R_4$, m, $R_5$, $R_6$ and p are defined in the same manner as above.

In another preferred embodiment, a stereoisomer of compound 2 is obtained when compound 1 is replaced with a stereoisomer thereof.

In a seventh aspect, the present invention provides a method of preparing the compound of formula (3) or a stereoisomer thereof, which comprises the following steps:

(a) reacting compound 1 with diphenylmethanimine in an inert solvent to form compound 2; and

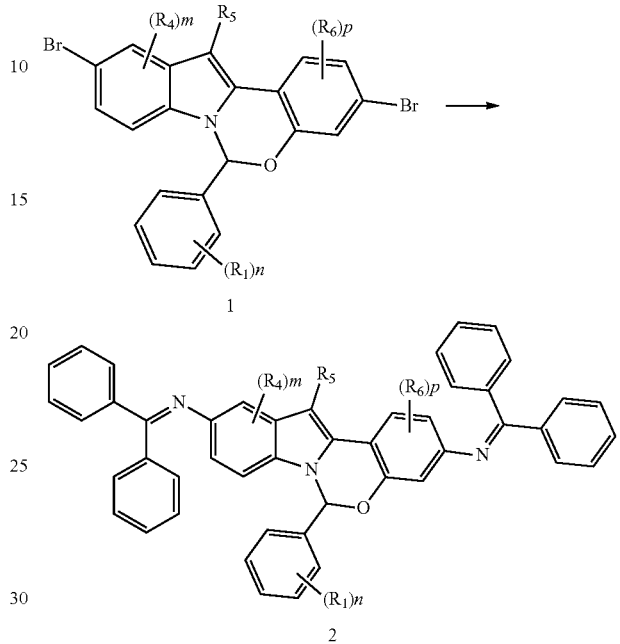

(b) reacting compound 2 with an acid in an inert solvent to form compound 3;

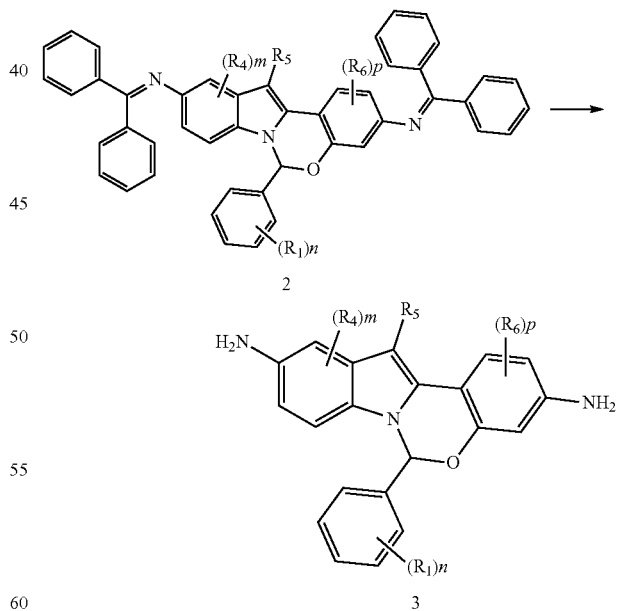

wherein, $R_1$, n, $R_4$, m, $R_5$, $R_6$ and p are defined in the same manner as above.

In another preferred embodiment, respective stereoisomers of compound 2 and compound 3 are obtained when compound 1 is replaced with a stereoisomer thereof.

It should be understood that various technical features of the present invention described above and various technical features described hereinafter (for example, in embodiments) can be combined with each other to constitute a new or preferred technical solution that will not be described here due to pages of this application.

DETAILED DESCRIPTION OF EMBODIMENTS

The inventor has surprisingly found, through a long-term and in-depth research, that some compounds have excellent anti-HCV activities, and based on this the inventor has completed the present invention.

Terminology

As used herein, term "$C_1$-$C_6$ alkyl" refers to a straight or branched alkyl having 1 to 6 carbon atoms, such as methyl, ethyl, propyl, isopropyl, butyl, isobutyl, sec-butyl, a t-butyl, or the like.

As used herein, term "$C_1$-$C_6$alkoxy" refers to a straight or branched alkoxy having 1 to 6 carbon atoms, such as methoxy, ethoxy, propoxy, isopropoxy, butoxy, isobutoxy, sec-butoxy, tert-butoxy, or the like.

As used herein, term "$C_3$-$C_8$ cycloalkyl" refers to a cycloalkyl having 3 to 8 carbon atoms, such as cyclopropyl, cyclobutyl, cyclopentyl, cyclohexyl, or the like.

As used herein, term "3- to 8-membered heterocyclic group" refers to a heterocyclic group having 3 to 8 ring atoms, which may comprise 1 to 2 hetero atoms selected from nitrogen, oxygen and sulfur, that is, pyrrole, furan, thiazole, or the like.

As used herein, term "$C_1$-$C_6$carboxyl" refers to a carboxyl having 1 to 6 carbon atoms, such as formyloxy, acetoxy, propionyloxy, butyryloxy, or the like.

As used herein, term "$C_1$-$C_6$ester group" refers to an ester group having 1 to 6 carbon atoms, such as —$COOCH_3$, —$COOCH_2CH_3$, —$COOCH_2CH_2CH_3$, or the like.

As used herein, term "$C_2$-$C_6$ alkanoyl" refers to a substituent" straight or branched alkyl-carbonyl having 2 to 6 carbon atoms", such as acetyl, propionyl, butyryl, or the like.

As used herein, term "$C_2$-$C_6$alkylamide" refers to a substituent "straight or branched alkyl-amide group having 2 to 6 carbon atoms", such as acetamido, propionamide, butyramide, or the like.

As used herein, term "$C_1$-$C_6$alkylamino" refers to a substituent "straight or branched alkyl-amino having 1 to 6 carbon atoms", such as methylamino, dimethylamino, an ethylamino, propylamine, diethylamino, or the like.

Term "halogen" refers to F, Cl, Br or I.

Term "halogenated" refers to fluorinated, chlorinated, bromated or iodinated.

As used herein, term "containing", "including" or "comprising" means that various ingredients may be used together in the mixture or composition of the invention. Therefore, terms "mainly consisting of" and "consisting of" are incorporated into the term "containing".

As used herein, term "pharmaceutically acceptable" ingredient refers to a substance which is suitable for humans and/or animals without excessive adverse effects such as toxicity, irritation and allergy, that is, a substance with a reasonable benefit-risk ratio.

As used herein, term "effective amount" refers to an amount at which a therapeutic agent used can treat, alleviate or prevent a target disease or condition or an amount at which a therapeutic agent used can exhibit a detectable therapeutic or prophylactic effect. A precise effective amount to a subject depends on the size and health of the subject, the nature and extent of the symptom and the selected therapeutic agent and/or combination of therapeutic agents. Therefore, it is useless to specify a precise effective amount in advance. However, for some specific conditions, a clinician is able to determine the effective amount through conventional experiment.

As used herein, term "substitution", unless otherwise specified, means that one or more hydrogen atoms on a group are substituted with a substituent selected from the groups consisting of halogen, $C_1$-$C_3$ alkyl, $C_1$-$C_3$ haloalkyl, nitro, hydroxyl, amino and cyano group.

Unless otherwise specified, all compounds used in the present invention are intended to comprise all possible optical isomers, such as single chiral compounds, or a mixture of various chiral compounds (i.e., racemates). Among all the compounds of the present invention, each of the chiral carbon atoms may be optionally R or S configuration, or a mixture thereof.

As used herein, term "compound of the present invention" refers to a compound of formula (I). Such term further involves various crystal forms, stereoisomers, tautomers, nitrogen oxides, metabolites, prodrugs, pharmaceutically acceptable salts, hydrates or solvates of the compounds of formula (I).

As used herein, term "pharmaceutically acceptable salt" refers to a salt formed by the compound of the invention with an acid or base and suitable for use as a medicine. The pharmaceutically acceptable salts comprise inorganic and organic salts. A preferred class of salts is formed by the compound of the invention with an acid. The acids suitable for forming the salts comprise but are not limited to: inorganic acids such as drochloric acid, hydrobromic acid, hydrofluoric acid, sulfuric acid, nitric acid and phosphoric acid, organic acids such as formic acid, acetic acid, propionic acid, oxalic acid, malonic acid, succinic acid, fumaric acid, maleic acid, lactic acid, malic acid, tartaric acid, citric acid, picric acid, methanesulfonic acid, phenylmethanesulfonic acid and benzenesulfonic acid, and acidic amino acids such as aspartic acid and glutamic acid.

Some of the compounds of the invention may be crystallized or recrystallized with water or various organic solvents, where various solvates may be formed. The solvates of the present invention comprise stoichiometric solvates such as hydrates and compounds containing variable amounts of crystal water formed upon the preparation using lyophilizaton. It should be understood that various thermodynamically stable isomers may be present after preparation of the compounds of the invention, such as tautomers, conformers, meso compounds, and enantiomers or diastereomers. The above-described variations will be apparent for those skilled in the art after reading the disclosure of the present invention.

Compound of Formula (I) and Preparation Thereof

The present invention provides a compound of formula (I),

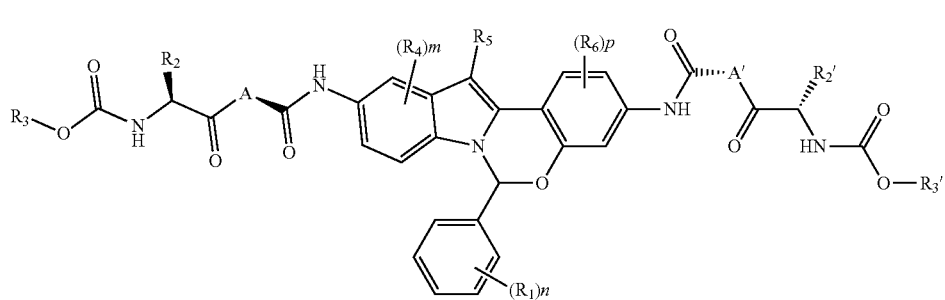

wherein, A, A', $R_1$, n, $R_2$, $R_2'$, $R_3$, $R_3'$, $R_4$, m, $R_5$, $R_6$ and p are defined in the same manner as above.

The present invention further provides a method of preparing the compound of formula (I). Certainly, the compound of the present invention can be prepared using a conventional method in the art and can also be prepared using the method provided herein.

In another preferred embodiment, the method provided by the present invention comprises the following steps:

(a) reacting compound 1 with diphenylmethanimine using a catalytic system (such as a catalytic system including $pd_2(dba)_3$, BINAP and sodium tert-butoxide) in an inert solvent to form compound 2

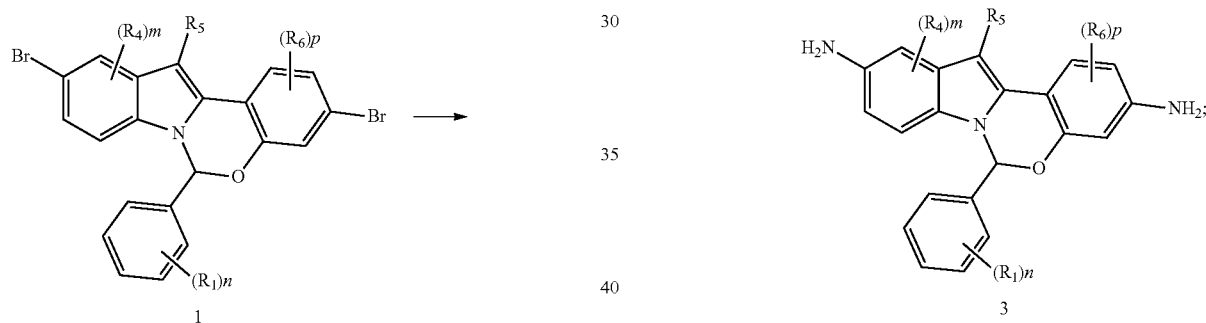

(b) reacting compound 2 with an acid (such as an inert solvent containing hydrochloric acid or hydrogen chloride) in an inert solvent to form compound 3

(c) reacting compound 3 with

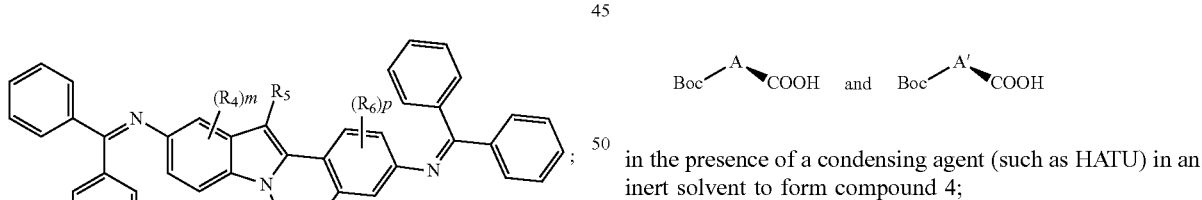

in the presence of a condensing agent (such as HATU) in an inert solvent to form compound 4;

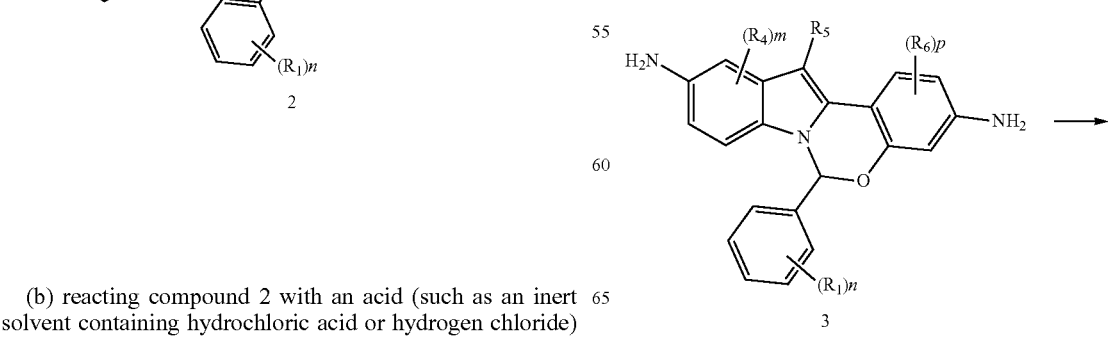

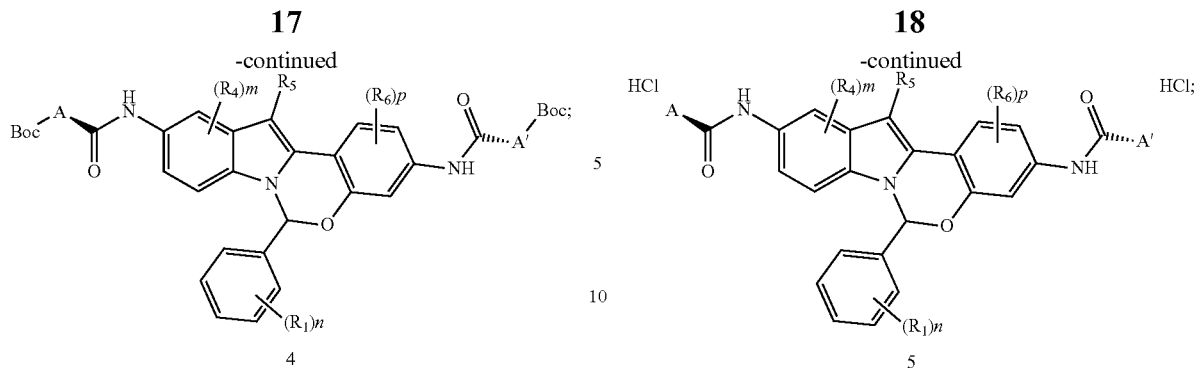
(d) reacting compound 4 with an acid (such as an inert solvent containing hydrogen chloride) in an inert solvent to form compound 5;
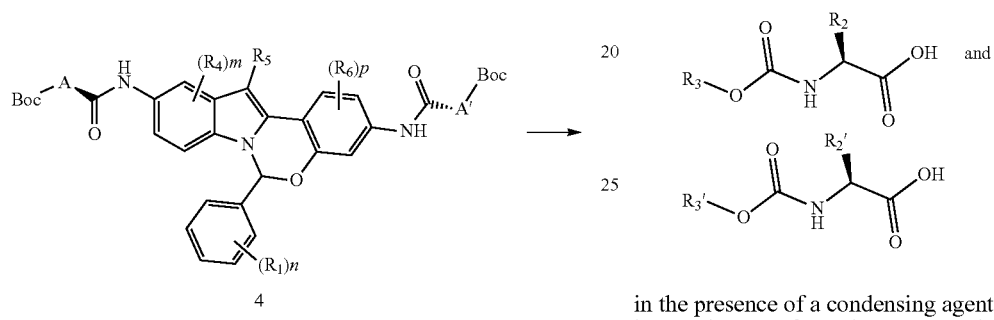
and
(e) reacting compound 5 with
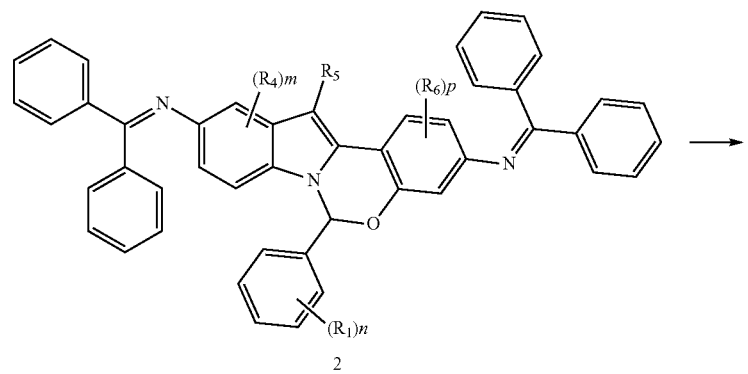
in the presence of a condensing agent (such as HATU) in an inert solvent to form the compound of formula (I)
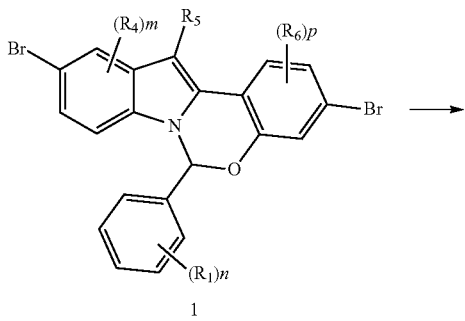

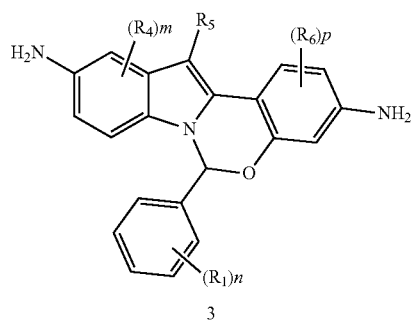

3

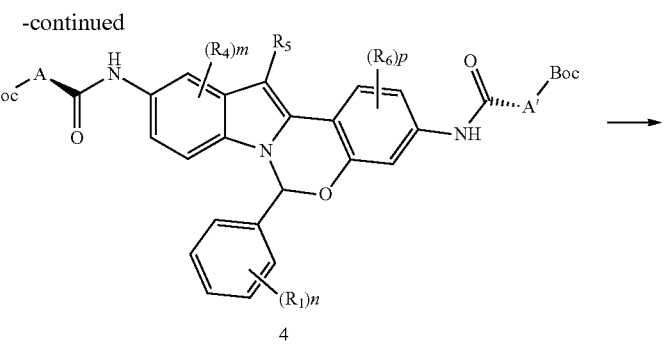

4

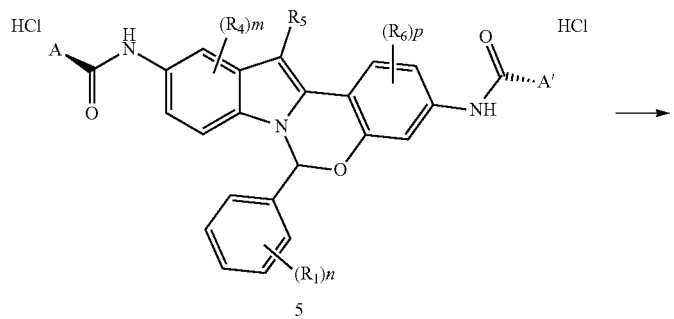

5

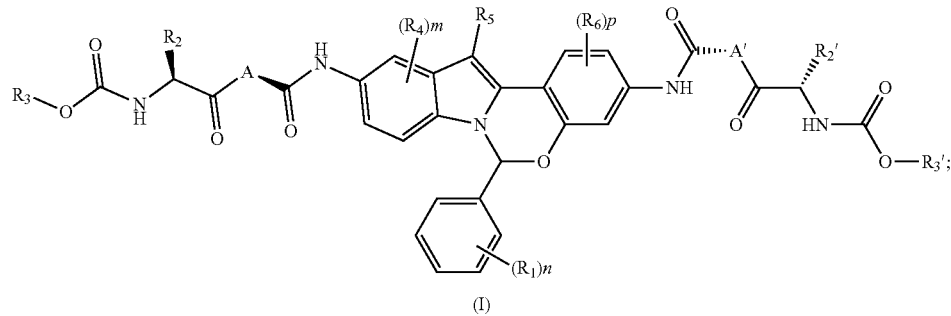

(I)

wherein, A, A', $R_1$, n, $R_2$, $R_2'$, $R_3$, $R_3'$, $R_4$, m, $R_5$, $R_6$ and p are defined in the same manner as above.

In another preferred embodiment, the inert solvent used in the preparation method of the invention is selected from the group consisting of acetic acid, ethanol, N, N-dimethylformamide (DMF), toluene, tetrahydrofuran, dichloromethane, ethyl acetate (EA), or a combination thereof.

In another preferred embodiment, such reactions are carried out at 20-150° C., preferably at 25-120° C.

It should be understood that if a compound of formula (I-a) used as a starting material is a chiral compound, a corresponding final compound is also a chiral compound. For example, a method of preparing the compound of formula (I-a) comprises the following steps:

(a) reacting a compound of formula (1-a) with diphenylmethanimine in an inert solvent to form a compound of formula (2-a);

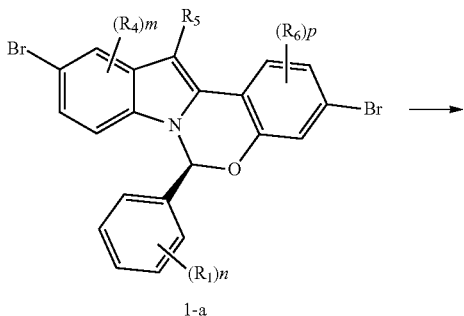

1-a

-continued

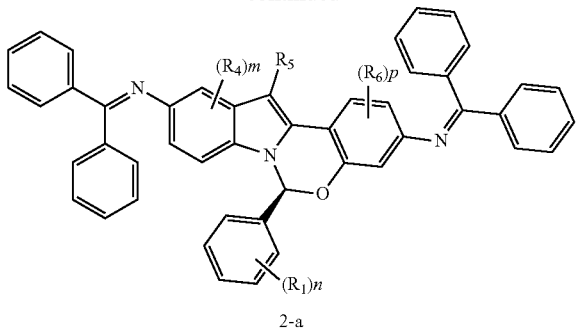
2-a (b) reacting the compound of formula (2-a) with an acid in an inert solvent to form a compound of formula (3-a);

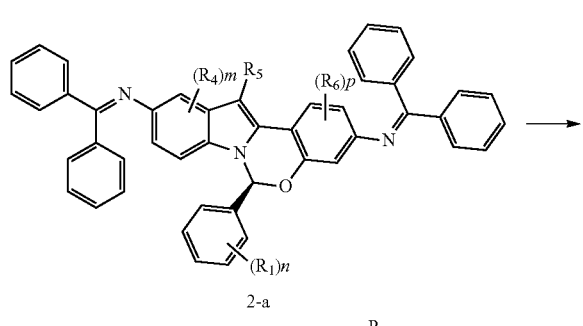
2-a

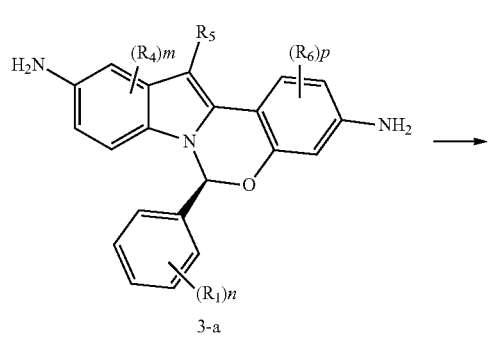
3-a (c) reacting the compound of formula (3-a) with

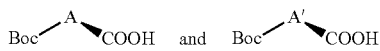

in an inert solvent to form a compound of formula (4-a);

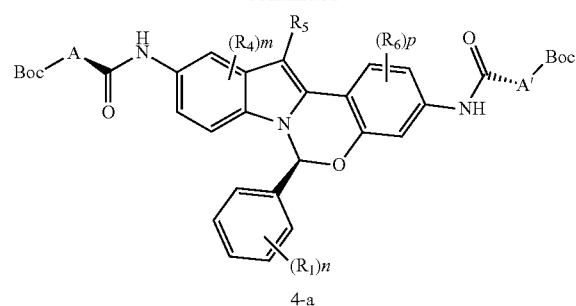
4-a (d) reacting the compound of formula (4-a) with an acid in an inert solvent to form a compound of formula (5-a); and

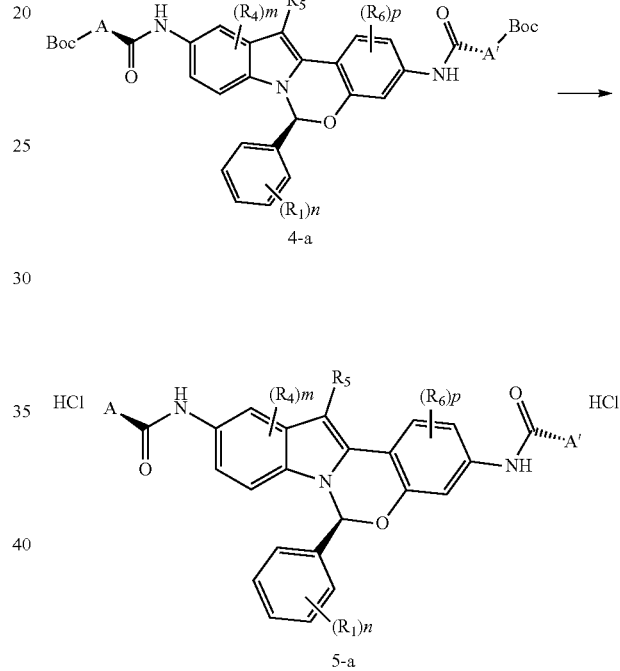

(e) reacting the compound of formula (5-a) with

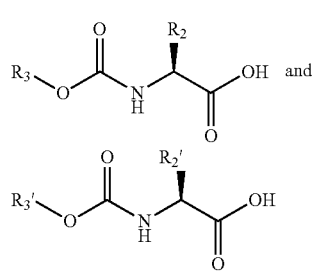

in an inert solvent to form the compound of formula (I-a).

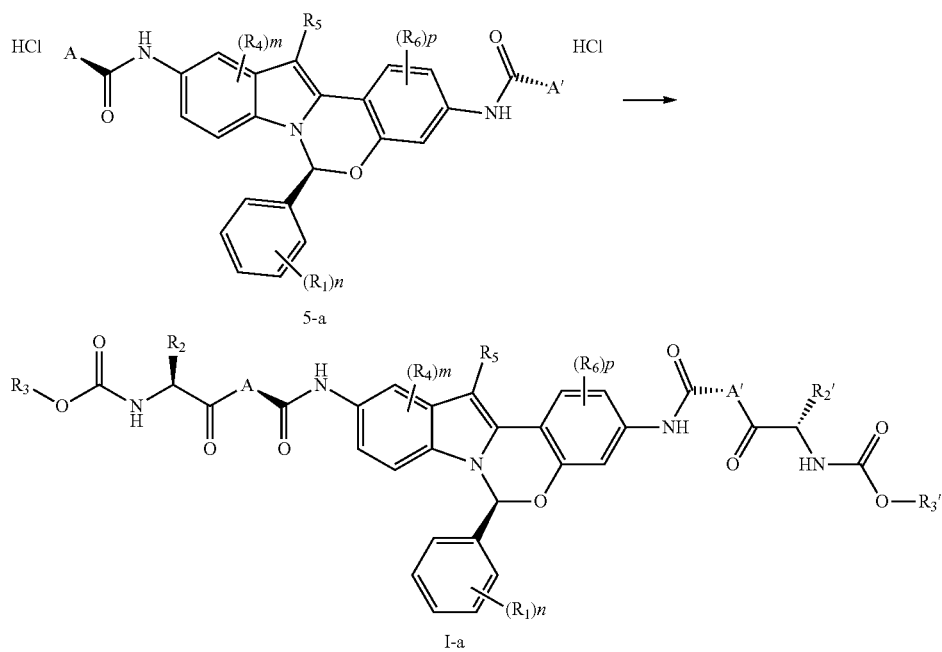

5-a

I-a

Similarly, those skilled in the art can also prepare a compound of formula (I-b) using the compound of formula (1-b) as a starting material.

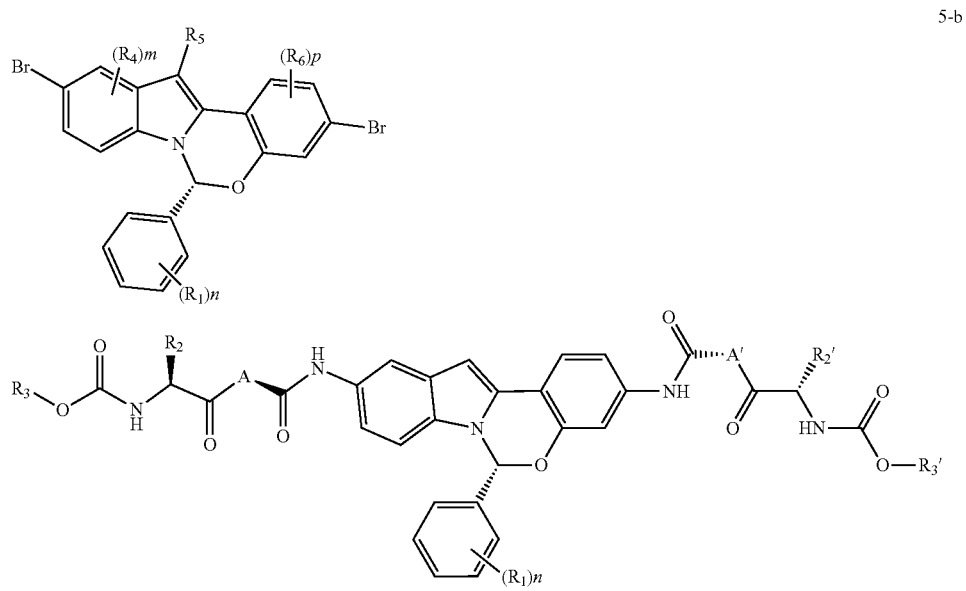

5-b

Pharmaceutical Composition and Administration

Since the compound of the present invention has an excellent inhibitory activity against hepatitis C virus (HCV), the compound of the present invention and various crystal forms, stereoisomers, tautomers, nitrogen oxides, metabolites, prodrugs, pharmaceutically acceptable inorganic or organic salts, hydrates or solvates thereof, and a pharmaceutical composition containing the compound of the present invention as a main active ingredient all can be used for the treatment, prevention, and alleviation of diseases caused by HCV infection. Based on the prior art, the compound of the invention can be used to treat the following disease: hepatitis C.

The pharmaceutical composition of the present invention comprises the compound of the invention or pharmaceutically acceptable salts thereof at a safe and effective amount and pharmaceutically acceptable excipients or carriers. Where, the "safe and effective amount" refers to an amount at which the compound used is sufficient to significantly improve symptoms without causing serious side effects. Generally, the pharmaceutical composition comprises the compound of the present invention at 0.1-1000 mg per dose, and preferably at 0.5-100 mg per dose. Preferably, the "per dose" refers to a capsule or tablet.

"Pharmaceutically acceptable carrier" refers to one or more solid or liquid fillers or gel materials of compatibility which are suitable for human use and must be of sufficient purity and sufficiently low toxicity. The "compatibility" indicates herein that each component of a composition is capable of blending with each other and with the compound of the invention without significantly reducing the effect of the compound. Parts of the pharmaceutically acceptable carriers comprise cellulose and its derivatives (such as sodium carboxymethylcellulose, sodium ethylcellulose and cellulose acetate), gelatin, talc, solid lubricants (such as stearic acid, magnesium stearate), calcium sulfate, vegetable oils (such as soybean oil, sesame oil, peanut oil and olive oil), polyols (such as propylene glycol, glycerin, mannitol and sorbitol), emulsifiers (such as Tween), wetting agents (such as sodium dodecyl sulfate), colorants, flavoring agents, stabilizers, antioxidants, preservatives and pyrogen-free water.

The administrations of the compound or the pharmaceutical composition of the present invention are not particularly limited, and representative administrations comprise but are not limited to: oral, rectal, parenteral (intravenous, intramuscular or subcutaneous) and topical administrations, and particularly preferably oral administration.

Solid preparations for oral administration comprise capsule, tablet, pill, powder and granule. In such solid preparations, the active compound is mixed with at least one conventional inert excipient (or carrier), such as sodium citrate or dicalcium phosphate, or mixed with the following components including: (a) a filler or compatibilizer such as starch, lactose, sucrose, glucose, mannitol and silicic acid; (b) a binder such as hydroxymethylcellulose, alginates, gelatin, polyvinylpyrrolidone, sucrose and gum arabic; (c) a humectant such as glycerin; (d) a disintegrating agent such as agar, calcium carbonate, potato starch or tapioca starch, alginic acid, some composite silicates and sodium carbonate; (e) a slow solvent, such as paraffin; (f) an absorbing accelerator, such as quaternary amine compounds; (g) a wetting agent, such as cetanol and glyceryl monostearate; (h) an adsorbent, such as kaoline; and (i) a lubricant, such as talc, calcium stearate, magnesium stearate, solid polyethylene glycol, sodium dodecyl sulfate, or a mixture thereof. A buffering agent may be also comprised in capsule, tablet and pill preparations.

Solid preparations such as tablet, sugar pill, capsule, pill and granule can be prepared using a coating or shell, such as casing and other materials known in the art. Such preparations may comprise an opacifying agent, and the release of the active compound or the compound of the composition may be carried out in a certain part of digestive tract in a tardive manner. Embedding components such as polymeric materials and waxy materials may be employed herein. If necessary, the active compound may also be used to prepare a microcapsule with one or more of the above excipients.

Liquid preparations used for oral administration comprised pharmaceutically acceptable emulsion, solution, suspension, syrup or tincture. In addition to the active compound, the liquid preparations may also comprise an inert diluent conventionally used in the art, such as water or other solvents, solubilizer and emulsifier, including ethanol, isopropanol, ethyl carbonate, ethyl acetate, propylene glycol, 1,3-butanediol, dimethylformamide and oils, especially cottonseed oil, peanut oil, corn germ oil, olive oil, castor oil and sesame oil or a mixture thereof.

In addition to such inert diluents, the composition may also comprise an auxiliary, such as wetting agent, emulsifier, suspending agent, sweetener, corrigent and spice.

In addition to the active compound, the suspension may comprise a suspending agent, such as ethoxylated isostearyl alcohol, polyoxyethylene sorbitol and sorbitan ester, microcrystalline cellulose, aluminum methylate and agar or a mixture thereof.

The composition for parenteral injection may comprise a physiologically acceptable sterile aqueous or non-aqueous solution, dispersion, suspension or emulsion, and sterile powder for reconstitution into sterile injectable solutions or dispersions. Appropriate aqueous and non-aqueous carriers, diluents, solvents or excipients comprise water, ethanol, polyols and an appropriate mixture thereof.

Preparations of the compound of the present invention for topical administration comprise ointment, powder, patch, spray and inhalant. The active ingredient is mixed under sterile conditions with a physiologically acceptable carrier and any preservatives, buffering agents, or propellants which may be required if necessary.

The compound of the invention may be administered alone or in combination with other pharmaceutically acceptable compounds. When the pharmaceutical composition is used, a safe and effective amount of the compound of the invention is administered to mammals (such as humans) needed to be treated, where a pharmaceutically acceptable effective dosage is employed for administration. For a human of 60 kg body weight, a daily dosage is usually 0.2-1000 mg and preferably 0.5-500 mg. Certainly, other factors including administration routes and health of patients should also be taken into consideration for determining a specific dosage which is within the skill of the skilled physician.

Advantages of the present invention are described as follows.

1. The present invention provides a compound for prevention and/or treatment of diseases (such as hepatitis C) caused by HCV infection. The compound can be used to selectively inhibit the HCV replication. In addition, the compound is capable of effectively inhibiting the function of NS5A protein encoded by hepatitis C virus.

2. The present invention provides a preparation method of the compound and use of the compound as an inhibitor of NS5A.

3. The present further provides an intermediate used in the preparation of the compound.

The invention will be further illustrated below in conjunction with specific embodiments. It should be understood that these embodiments are merely used to describe the invention but not intended to limit the scope of the invention. In the following examples, the experimental methods of which the specific conditions are not specified, are usually carried out according to conventional conditions or the conditions recommended by the manufacturer. Unless otherwise specified, percentage and portion are calculated by weight.

Meanings of abbreviations used in the invention are listed as follows:

PPA: polyphosphoric acid; and DEA: diethylamine.

Example 1: PA6001
Synthetic Route:
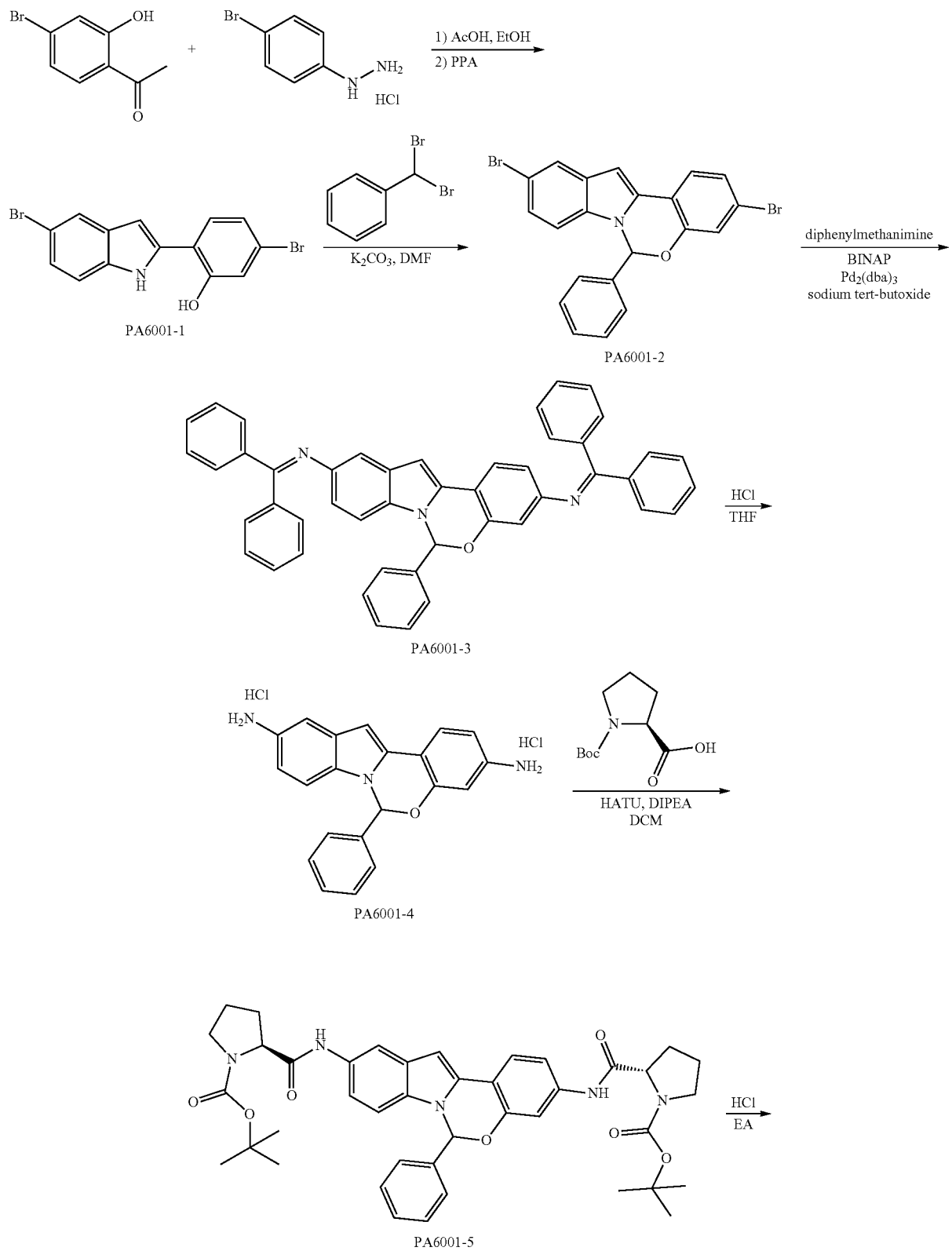

-continued
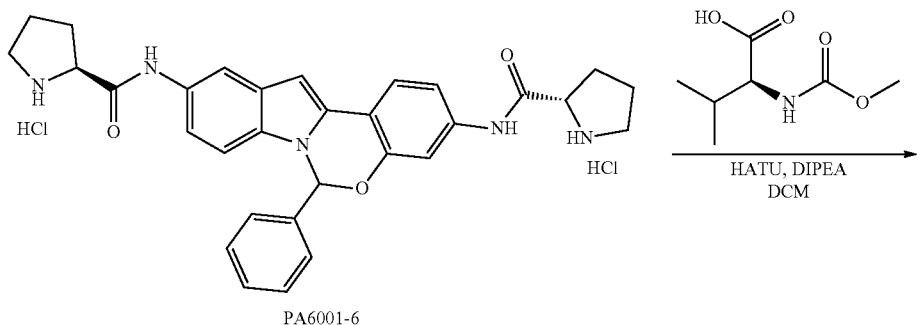
PA6001-6
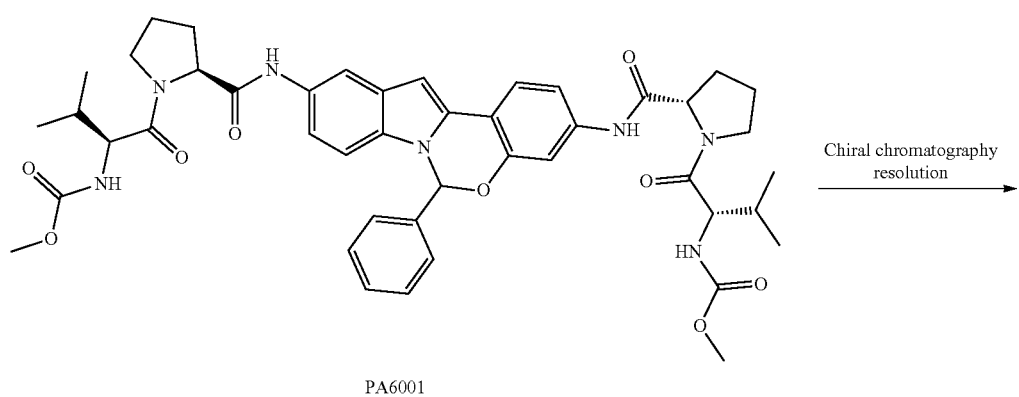
PA6001
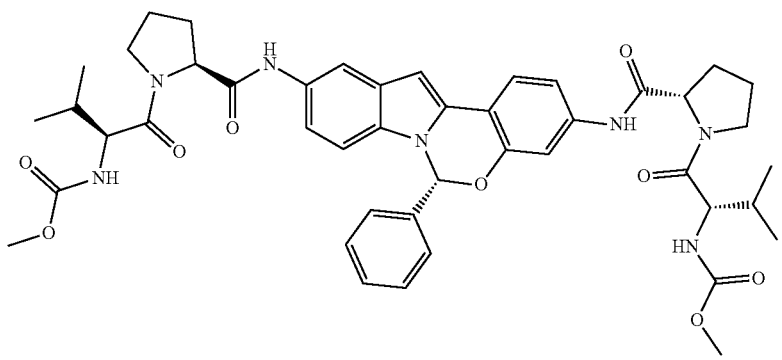
PA6001-A
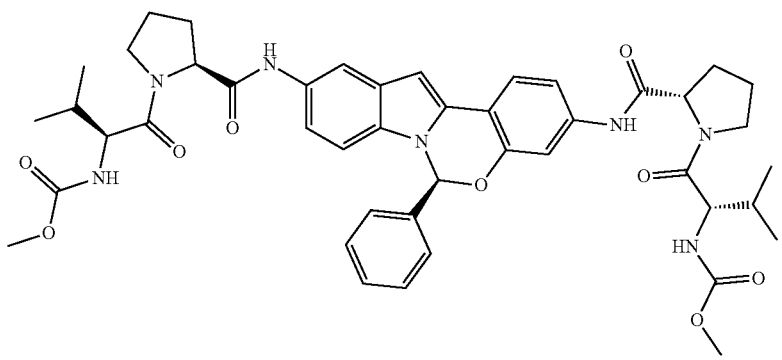
PA6001-B

Experiment

Step (1) Synthesis of Compound PA6001-1

10 g of 4-bromo-2-hydroxyacetophenone (46.5 mmol) was dissolved in 165 mL of a solvent prepared by acetic acid and ethanol at a ratio of 1:10 to produce a solution. 10 g of 4-bromophenylhydrazine hydrochloride (44.7 mmol) was added to the solution. The reaction was heated to reflux for 6 hours. After the reaction, the resulting product was cooled to room temperature and then evaporated under rotation to remove the solvent. 14 g of a white solid crude product was obtained with a yield of 78%. 10 g of the crude solid product was dissolved in 60 mL of PPA to produce a blend. The blend was reacted at 80° C. for 2 hours.

The resulting product was cooled to room temperature and added with 200 mL of ice water to obtain a mixture. The mixture was extracted with DCM three times each of 150 mL. The organic phases were collected and combined. The combined organic phase was washed with a saturated saline, dried with anhydrous $Na_2SO_4$ and desolventized under vacuum to produce a residue. The residue was separated and purified using silica gel column chromatography with an eluent prepared by PE and EA at a volume ratio of 3:1 to obtain 6.6 g of a white solid product with a yield of 69%.

Step (2) Synthesis of Compound PA6001-2

1.0 g of compound PA6001-1 (2.72 mmol) was dissolved in 15 mL of DMF to produce a solution. 2.0 g of dibromotoluene (8.17 mmol) and 1.1 g of $K_2CO_3$ (8.17 mmol) were added to the solution. The reaction was stirred at 100° C. for 3 hours. The resulting product was cooled to room temperature and added with 100 mL of water to produce a mixture. The mixture was extracted with DCM three times each of 150 mL. The organic phases were collected and combined. The combined organic phase was washed with a saturated saline, dried with anhydrous $Na_2SO_4$ and desolventized under vacuum to obtain a residue. The residue was separated and purified using silica gel column chromatography with an eluent prepared by PE and EA at a volume ratio of 50:1 to obtain 600 mg of a white solid product with a yield of 48%.

Step (3) Synthesis of Compound PA6001-3

0.6 g of compound PA6001-2 (1.32 mmol) was dissolved in 10 mL of toluene to produce a solution. 525 mg of diphenylmethanimine (2.90 mmol), 60 mg of $Pd_2(dba)_3$ (0.06 mmol), 124 mg of BINAP (0.15 mmol) and 380 mg of sodium tert-butoxide (3.96 mmol) were added to the solution. The reaction was stirred under nitrogen protection at 100° C. for 10 hours. The resulting product was cooled to room temperature and added with 100 mL of water to produce a mixture. The mixture was extracted with DCM three times each of 150 mL. The three organic phases were collected and combined. The combined organic phase was washed with a saturated saline, dried with anhydrous $Na_2SO_4$ and desolventized under vacuum. The resulting product was separated and purified using silica gel column chromatography with an eluent prepared by PE and DCM at a volume ratio of 1:1 to obtain 650 mg of a yellow solid product with a yield of 75%.

Step (4) Synthesis of Compound PA6001-4

0.6 g of compound PA6001-3 (0.916 mmol) was dissolved in 5 mL of THF to produce a solution. 6 N hydrochloric acid was dripped into the solution at a rate of two drops per hour to start a reaction. The reaction was carried out for 12 hours and the progress thereof was monitored at any time. After the reaction, an off-white solid product, was observed in the resulting product and obtained with a filtration. The resulting solid product was washed with THF and dried under vacuum to obtain 340 mg of a final off-white solid product with a yield of 93%.

$^1$H NMR (400 MHz DMSO-$d_6$): δ:10.086 (s, 4H), 7.684 (s, 1H), 7.548-7.588 (m, 2H), 7.275-7.385 (m, 4H), 6.889-7.038 (m, 4H), 6.462 (d, J=9.2 Hz, 1H), 6.370 (s, 1H) ppm.

Step (5) Synthesis of Compound PA6001-5

300 mg of compound PA6001-4 (0.751 mmol) was dissolved in 5 mL of DCM to produce a solution. 415 mg of t-butoxycarbonyl-L-proline (1.654 mmol), 856 mg of HATU (2.251 mmol) and 582 mg of DIPEA (4.506 mmol) were added to the solution. The reaction was stirred at room temperature overnight. After the reaction, the resulting product was added with 100 mL of water to produce a mixture. The mixture was extracted with DCM three times each of 150 mL. The organic phases were collected and combined. The combined organic phase was washed with a saturated saline, dried with anhydrous $Na_2SO_4$ and desolventized under vacuum to produce a residue. The residue was separated and purified using silica gel column chromatography with an eluent prepared by PE and EA at a volume ratio of 1:1 to obtain 522 mg of a yellow solid product with a yield of 96%.

Step (6) Synthesis of Compound PA6001-6

590 mg of compound PA6001-5 (0.818 mmol) was dissolved in 3 mL of an EA solution containing 3 M HCl. The reaction was stirred at room temperature for 2-3 hours and a solid product was precipitated. When the reaction was confirmed to be completed through LC-MS monitoring, the resulting product was filtered to obtain 400 mg of a light brown solid crude product, which was directly employed in the next reaction.

Step (7) Synthesis of Compound PA6001

400 mg of the crude product of compound PA6001-6 was dissolved in 20 mL of DCM to produce a solution. 236 mg of N-methoxycarbonyl-L-valine (1.35 mmol), 768 mg of HATU (2.019 mmol) and 513 mg of DIPEA (4.038 mmol) were added to the solution. The reaction was stirred at room temperature overnight. After the reaction, the resulting product was added with 100 mL of water to produce a mixture. The mixture was extracted with DCM three times each of 150 mL. The organic phases were collected and combined. The combined organic phase was washed with a saturated saline, dried with anhydrous $Na_2SO_4$ and desolventized under vacuum to produce a residue. The residue was separated and purified using silica gel column chromatography with an eluent prepared by PE and EA at a volume ratio of 1:3 to obtain 450 mg of a yellow solid product with a yield of 66% (two-step reaction).

Step (8) Formation of Compound PA6001-A and Compound PA6001-B 300 mg of compound PA6001 was separated chirally to obtain 100 mg of PA6001-A with an ee value greater than 98% and 110 mg of PA6001-B with an ee value greater than 98%, respectively.

Chiral Analysis Parameters:

Analytical column: Cellulose-4, purchased from Guangzhou FLM Scientific Instrument Co., Ltd.

Mobile phase: a methanol solution containing 0.1% DEA.

Wavelength: 214 nm and 254 nm.

Flow rate: 1.0 mL/min.

Temperature: 40° C.

Example 2: PA6002
Synthetic Route
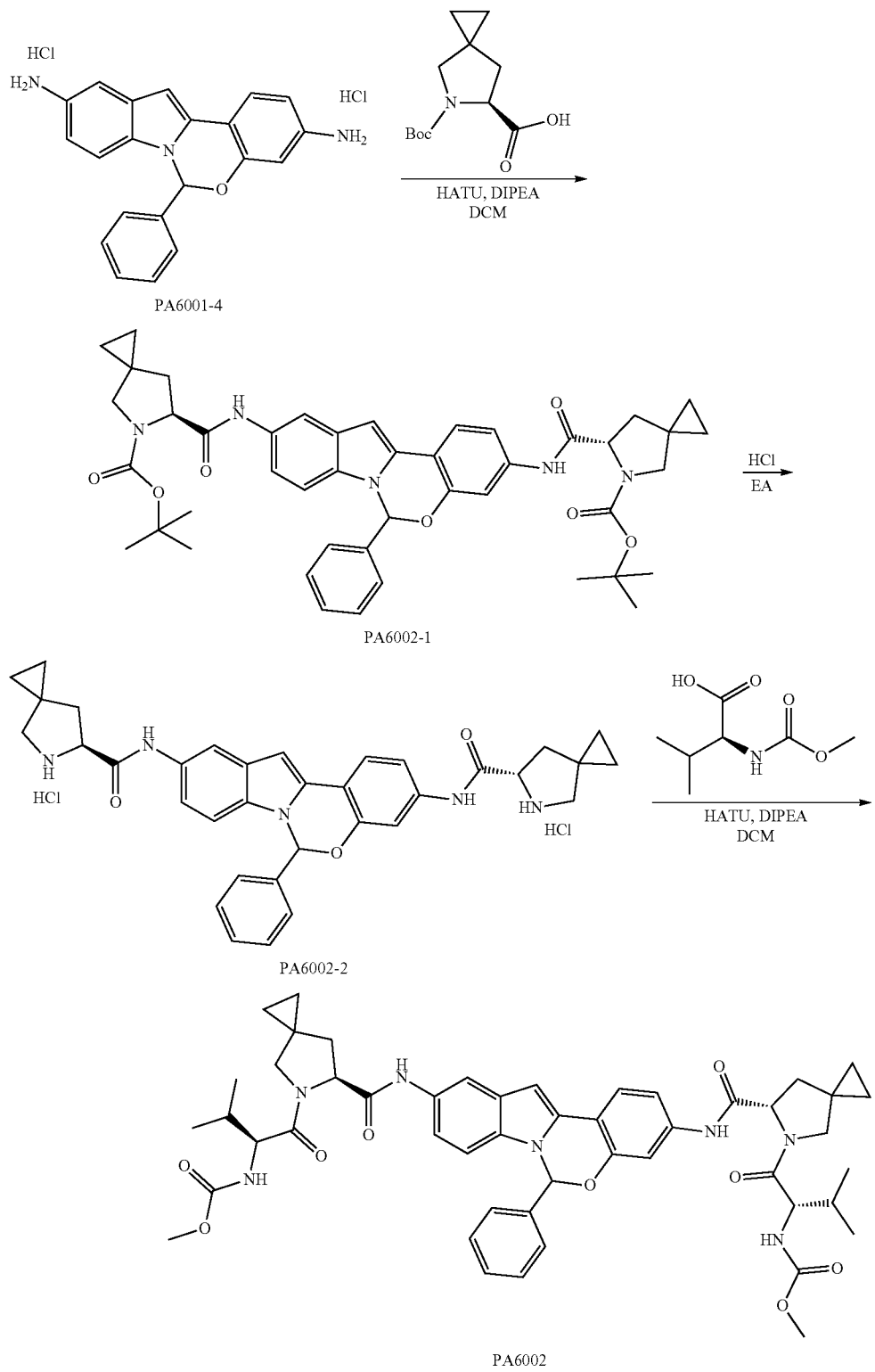

Experiment

Step (1) Synthesis of Compound PA6002-1

290 mg of compound PA6001-4 (0.886 mmol) was dissolved in 5 mL of DCM to produce a solution. 544 mg of (S)-5-t-butoxycarbonyl-5-azaspirol [2.4]heptane-6-carboxyl (1.949 mmol), 1 g of HATU (2.658 mmol) and 573 mg of DIPEA (4.43 mmol) were added to the solution. The reaction was stirred at room temperature overnight. After the reaction, the resulting product was added with 100 mL of water to produce a mixture. The mixture was extracted with DCM three times each of 150 mL. The organic phases were collected and combined. The combined organic phase was washed with a saturated saline, dried with anhydrous $Na_2SO_4$ and desolventized under vacuum to produce a residue. The residue was separated and purified using silica gel column chromatography with an eluent prepared by PE and EA at a volume ratio of 1:1 to obtain 560 mg of a yellow solid product with a yield of 82%.

Step (2) Synthesis of Compound PA6002-2

560 mg of compound PA6002-1 (0.724 mmol) was dissolved in 5 mL of an EA solution containing 3 M HCl. The reaction was stirred at room temperature for 2-3 hours and a solid product was precipitated. When the reaction was confirmed to be completed through LC-MS monitoring, the resulting product was filtered to obtain 327 mg of a slight brown solid crude product, which was directly employed in the next reaction.

Step (3) Synthesis of Compound PA6002

327 mg of the crude product of compound PA6002-2 was dissolved in 20 mL of DCM to produce a solution. 195 mg of N-methoxycarbonyl-L-valine (1.113 mmol), 578 mg of HATU (1.518 mmol) and 359 mg of DIPEA (2.783 mmol) were added to the solution. The reaction was stirred at room temperature overnight. After the reaction, the resulting product was added with 100 mL of water to produce a mixture. The mixture was extracted with DCM three times each of 160 mL. The organic phases were collected and combined. The combined organic phase was washed with a saturated saline, dried with anhydrous $Na_2SO_4$ and desolventized under vacuum to produce a residue. The residue was separated and purified using silica gel column chromatography with an eluent prepared by PE and EA at a volume ratio of 1:3 to obtain 513 mg of a white solid product with a yield of 80% (two-step reaction).

Example 3: PA6010

Synthetic Route

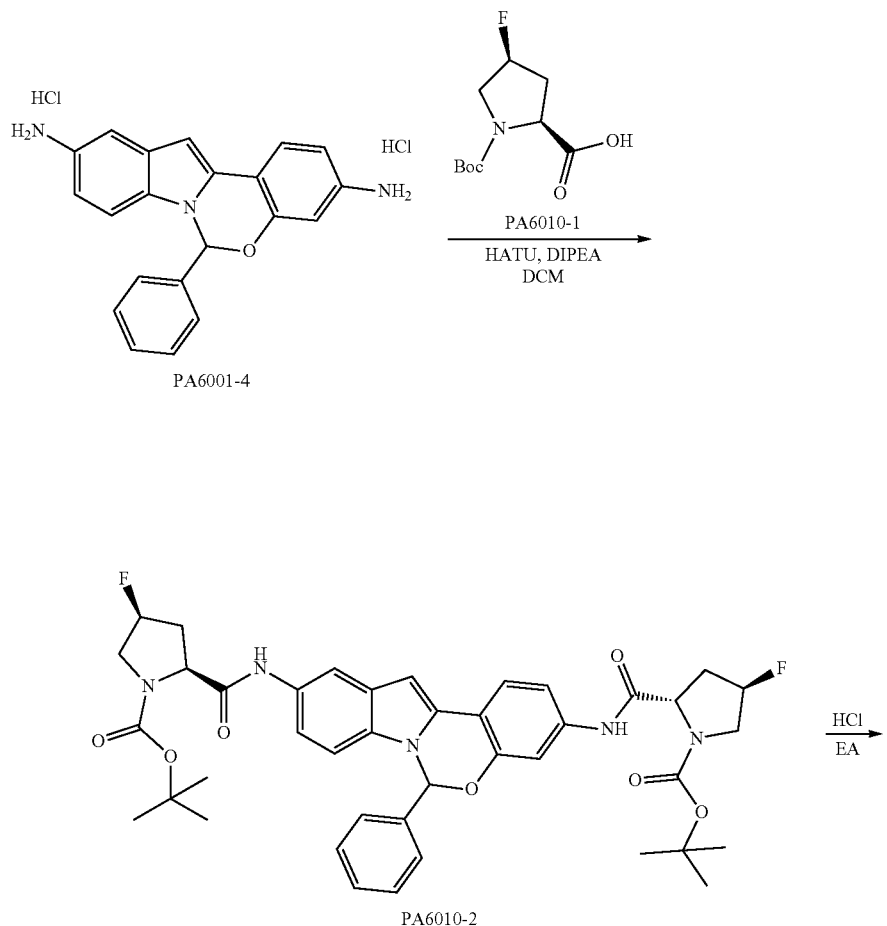

-continued

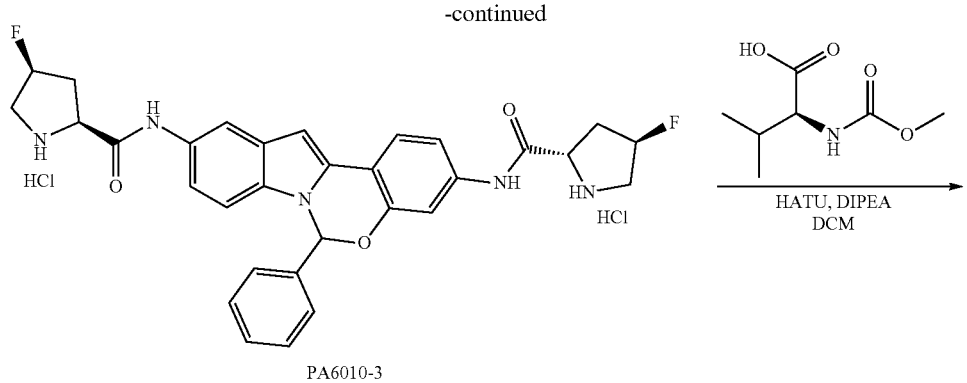

PA6010-3

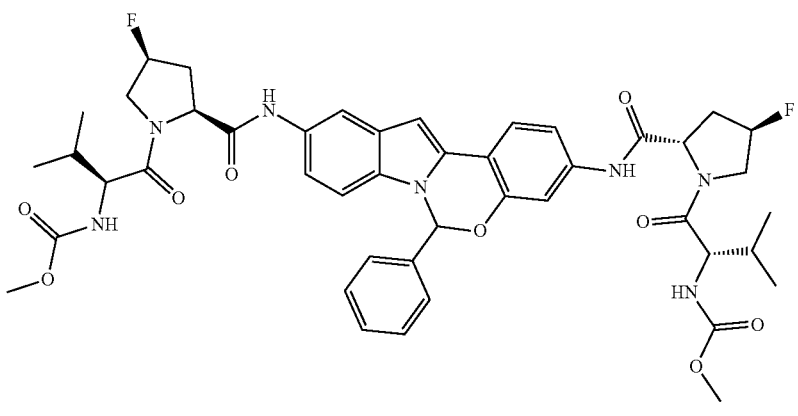

PA6010

Experiment

Step (1) Synthesis of Compound PA6010-2

80 mg of compound PA6010-2 (0.200 mmol) was dissolved in 5 mL of DCM to produce a solution. 102.8 mg of PA6010-1 (0.441 mmol), 228 mg of HATU (0.60 mmol) and 129 mg of DIPEA (1.00 mmol) were added to the solution. The reaction was stirred at room temperature overnight. After the reaction, the resulting product was added with 50 mL of water to produce a mixture. The mixture was extracted with DCM three times each of 100 mL. The organic phases were collected and combined. The combined organic phase was washed with a saturated saline, dried with anhydrous $Na_2SO_4$ and desolventized under vacuum to produce a residue. The residue was separated and purified using silica gel column chromatography with an eluent prepared by PE and EA at a volume ratio of 2:1 to obtain 140 mg of a yellow solid product with a yield of 93%.

Step (2) Synthesis of Compound PA6010-3

100 mg of compound PA6010-2 (0.132 mmol) was dissolved in 3 mL of an EA solution containing 3 M HCl. The reaction was stirred at room temperature overnight and a solid product was precipitated. The reaction was confirmed to be completed through LC-MS monitoring. The resulting product was filtered to obtain 40 mg of a slight brown solid crude product, which was directly employed in the next reaction.

Step (3) Synthesis of Compound PA6010

40 mg of the crude product of compound PA6010-3 was dissolved in 10 mL of DCM to produce a solution. 25 mg of N-methoxycarbonyl-L-valine (0.140 mmol), 73 mg of HATU (0.1908 mmol) and 49 mg of DIPEA (0.3816 mmol) were added to the solution. The reaction was stirred at room temperature overnight. After the reaction, the resulting product was added with 50 mL of water to produce a mixture. The mixture was extracted with DCM three times each of 100 mL. The organic phases were collected and combined. The combined organic phase was washed with a saturated saline, dried with anhydrous $Na_2SO_4$ and desolventized under vacuum to produce a residue. The residue was separated and purified using silica gel column chromatography with an eluent prepared by PE and EA at a volume ratio of 1:1 to obtain 45 mg of a white solid product with a yield of 39% (two-step reaction).

Example 4: PA6011
Synthetic Route
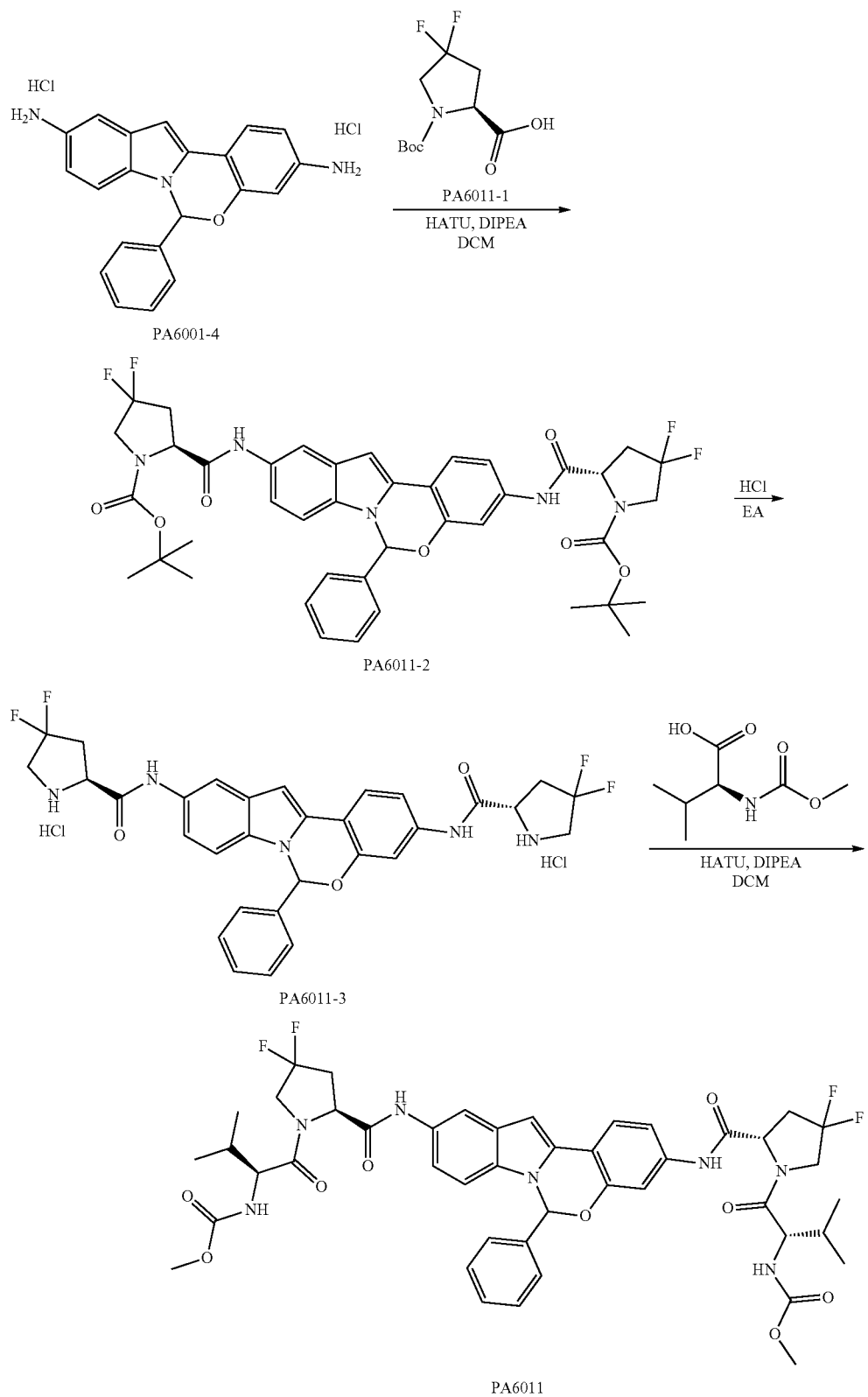

Experiment

Step (1) Synthesis of Compound PA6011-2

90 mg of compound PA6001-4 (0.225 mmol) was dissolved in 5 mL of DCM to produce a solution. 125 mg of PA6011-1 (0.496 mmol), 290 mg of HATU (0.765 mmol) and 171 mg of DIPEA (1.35 mmol) were added to the solution. The reaction was stirred at room temperature overnight. After the reaction, the resulting product was added with 50 mL of water to produce a mixture. The mixture was extracted with DCM three times each of 100 mL. The organic phases were collected and combined. The combined organic phase was washed with a saturated saline, dried with anhydrous $Na_2SO_4$ and desolventized under vacuum to produce a residue. The residue was separated and purified using silica gel column chromatography with an eluent prepared by PE and EA at a volume ratio of 2:1 to obtain 169 mg of a yellow solid product with a yield of 95%.

Step (2) Synthesis of Compound PA6011-3

150 mg of compound PA6011-2 (0.198 mmol) was dissolved in 3 mL of an EA solution containing 3 M HCl. The reaction was stirred at room temperature overnight and a solid product was precipitated. The reaction was confirmed to be completed through LC-MS monitoring. The resulting product was filtered to obtain 108 mg of a slight brown solid crude product, which was directly employed in the next reaction.

Step (3) Synthesis of Compound PA6011

100 mg of the crude product of compound PA6011-3 was dissolved in 10 mL of DCM to produce a solution. 58 mg of N-methoxycarbonyl-L-valine (0.330 mmol), 173 mg of HATU (0.450 mmol) and 116 mg of DIPEA (0.900 mmol) were added to the solution. The reaction was stirred at room temperature overnight. After the reaction, the resulting product was added with 50 mL of water to produce a mixture. The mixture was extracted with DCM three times each of 100 mL. The organic phases were collected and combined. The combined organic phase was washed with a saturated saline, dried with anhydrous $Na_2SO_4$ and desolventized under vacuum to produce a residue. The residue was separated and purified using silica gel column chromatography with an eluent prepared by PE and EA at a volume ratio of 1:3 to obtain 120 mg of a white solid product with a yield of 88%.

Example 5: PA6016

Synthetic Route

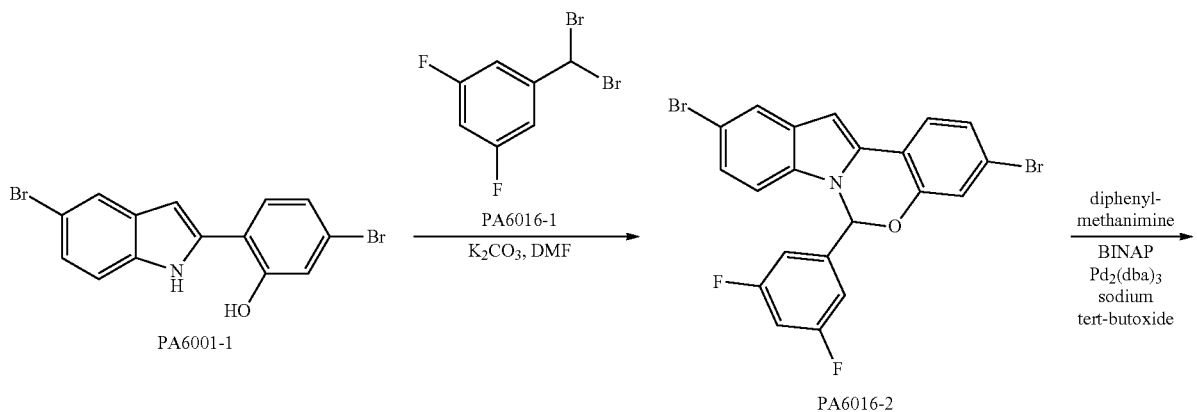

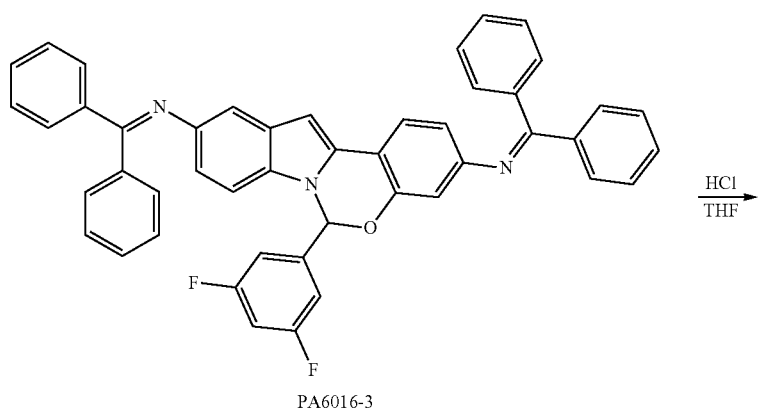

-continued
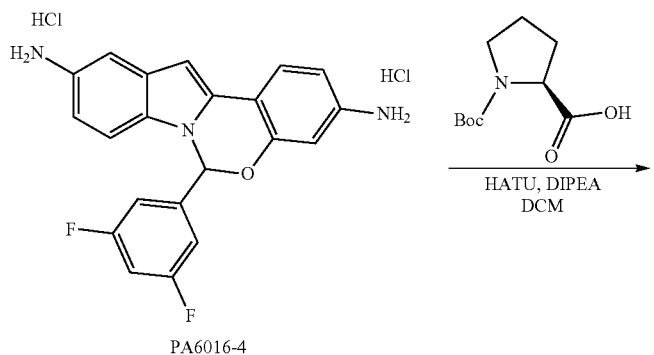
PA6016-4
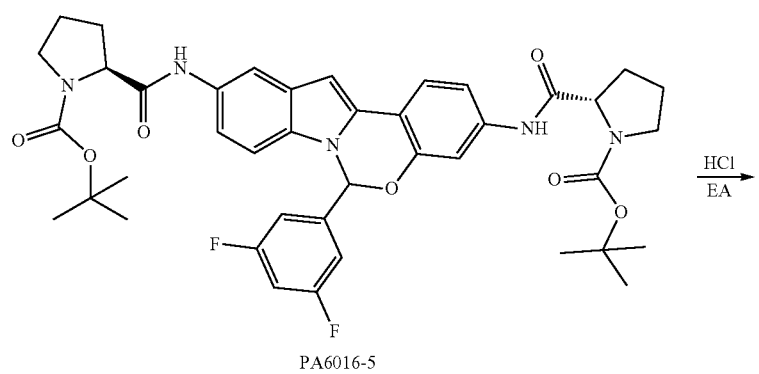
PA6016-5
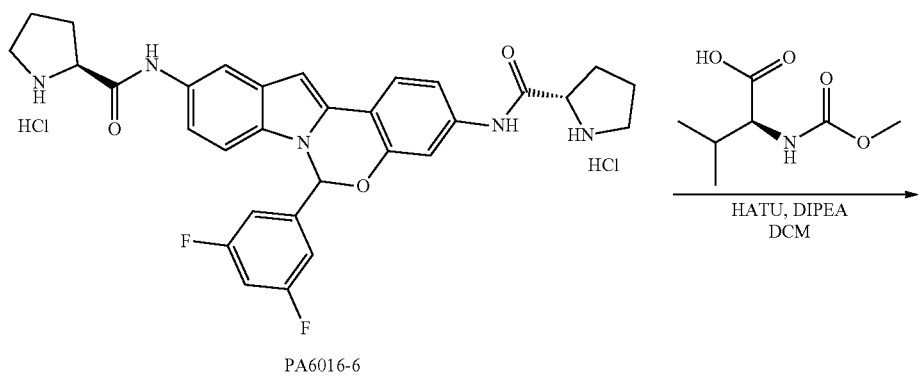
PA6016-6
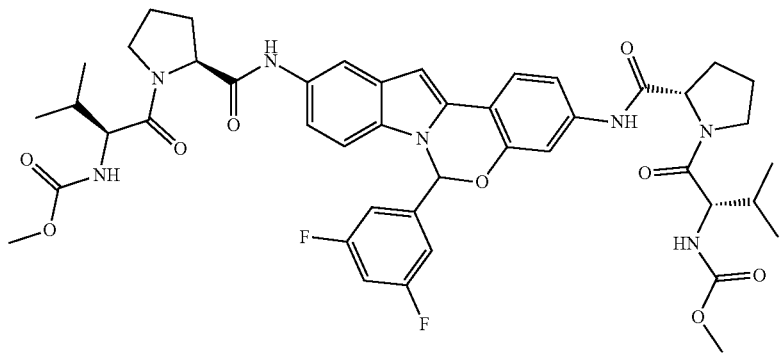
PA6016

Experiment

Step (1) synthesis of compound PA6016-2

1.23 g of compound PA6001-1 (3.35 mmol) was dissolved in 50 mL of DMF to produce a solution. 2.57 g of PA6016-1 (8.99 mmol) and 1.24 g of $K_2CO_3$ (8.99 mmol) were added to the solution. The reaction was stirred at 100° C. for 3 hours. The resulting product was cooled to room temperature and added with 150 mL of water to produce a mixture. The mixture was extracted with DCM three times each of 150 mL. The organic phases were collected and combined. The combined organic phase was washed with a saturated saline, dried with anhydrous $Na_2SO_4$ and desolventized under vacuum to produce a residue. The residue was separated and purified using silica gel column chromatography with an eluent prepared by PE and EA at a volume ratio of 50:1 to obtain 1.06 g of a white solid product with a yield of 64%.

Step (2) Synthesis of Compound PA6016-3

491 mg of compound PA6016-2 (1 mmol) was dissolved in 30 mL of toluene to produce a solution. 400 mg of diphenylmethanimine (2.2 mmol), 46 mg of $Pd_2(dba)_3$ (0.05 mmol), 93 mg of BINAP (0.15 mmol) and 288 mg of sodium tert-butoxide (3 mmol) were added to the solution. The reaction was stirred under nitrogen protection at 110° C. overnight. The resulting product was cooled to room temperature and added with 100 mL of water to produce a mixture. The mixture was extracted with DCM three times each of 150 mL. The organic phases were collected and combined. The combined organic phase was washed with a saturated saline, dried with anhydrous $Na_2SO_4$ and desolventized under vacuum to produce a residue. The residue was separated and purified using silica gel column chromatography with an eluent prepared by PE and DCM at a volume ratio of 1:1 to obtain 484 mg of a yellow solid product with a yield of 70%.

Step (3) Synthesis of Compound PA6016-4

484 mg of compound PA6016-3 (0.7 mmol) was dissolved in 5 mL of THF to produce a solution. 6 N hydrochloric acid was dripped into the solution at a rate of two drops per hour to start a reaction. The reaction was carried out for 12 hours and the progress thereof was monitored at any time. After the reaction, an off-white solid product was observed in the resulting product, and obtained with a filtration. The resulting solid product was washed with THF and dried under vacuum to obtain 275 mg of a final off-white solid product with a yield of 90%.

Step (4) Synthesis of Compound PA6016-5

75 mg of compound PA6016-4 (0.172 mmol) was dissolved in 8 mL of DCM to produce a solution. 81 mg of t-butoxycarbonyl-L-proline (0.378 mmol), 196 mg of HATU (0.516 mmol) and 111 mg of DIPEA (0.86 mmol) were added to the solution. The reaction was stirred at room temperature overnight. After the reaction, the resulting product was added with 50 mL of water to produce a mixture. The mixture was extracted with DCM three times each of 100 mL. The organic phases were collected and combined. The combined organic phase was washed with a saturated saline, dried with anhydrous $Na_2SO_4$ and desolventized under vacuum to produce a residue. The residue was separated and purified using silica gel column chromatography with an eluent prepared by DCM and MeOH at a volume ratio of 50:1 to obtain 117 mg of a colorless liquid with a yield of 90%.

Step (5) Synthesis of Compound PA6016-6

117 mg of compound PA6010-2 (0.154 mmol) was dissolved in 3 mL of an EA solution containing 3 M HCl. The reaction was stirred at room temperature overnight and a solid product was precipitated. The reaction was confirmed to be completed through LC-MS monitoring. The resulting product was filtered to obtain 60 mg of a slight brown solid crude product, which was directly employed in the next reaction.

Step (6) Synthesis of Compound PA6016

60 mg of the crude product of compound PA6016-6 was dissolved in 10 mL of DCM to produce a solution. 37 mg of N-methoxycarbonyl-L-valine (0.210 mmol), 108 mg of HATU (0.285 mmol) and 61 mg of DIPEA (0.475 mmol) were added to the solution. The reaction was stirred at room temperature overnight. After the reaction, the resulting product was added with 50 mL of water to produce a mixture. The mixture was extracted with DCM three times each of 100 mL. The organic phases were collected and combined. The combined organic phase was washed with a saturated saline, dried with anhydrous $Na_2SO_4$ and desolventized under vacuum to produce a residue. The residue was separated and purified using silica gel column chromatography with an eluent prepared by DCM and MeOH at a volume ratio of 50:1 to obtain 24 mg of a white solid product with a yield of 29%.

Example 6: PA6017

Synthetic Route

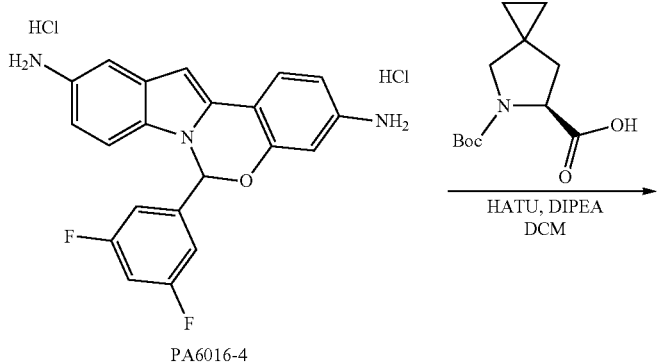

-continued

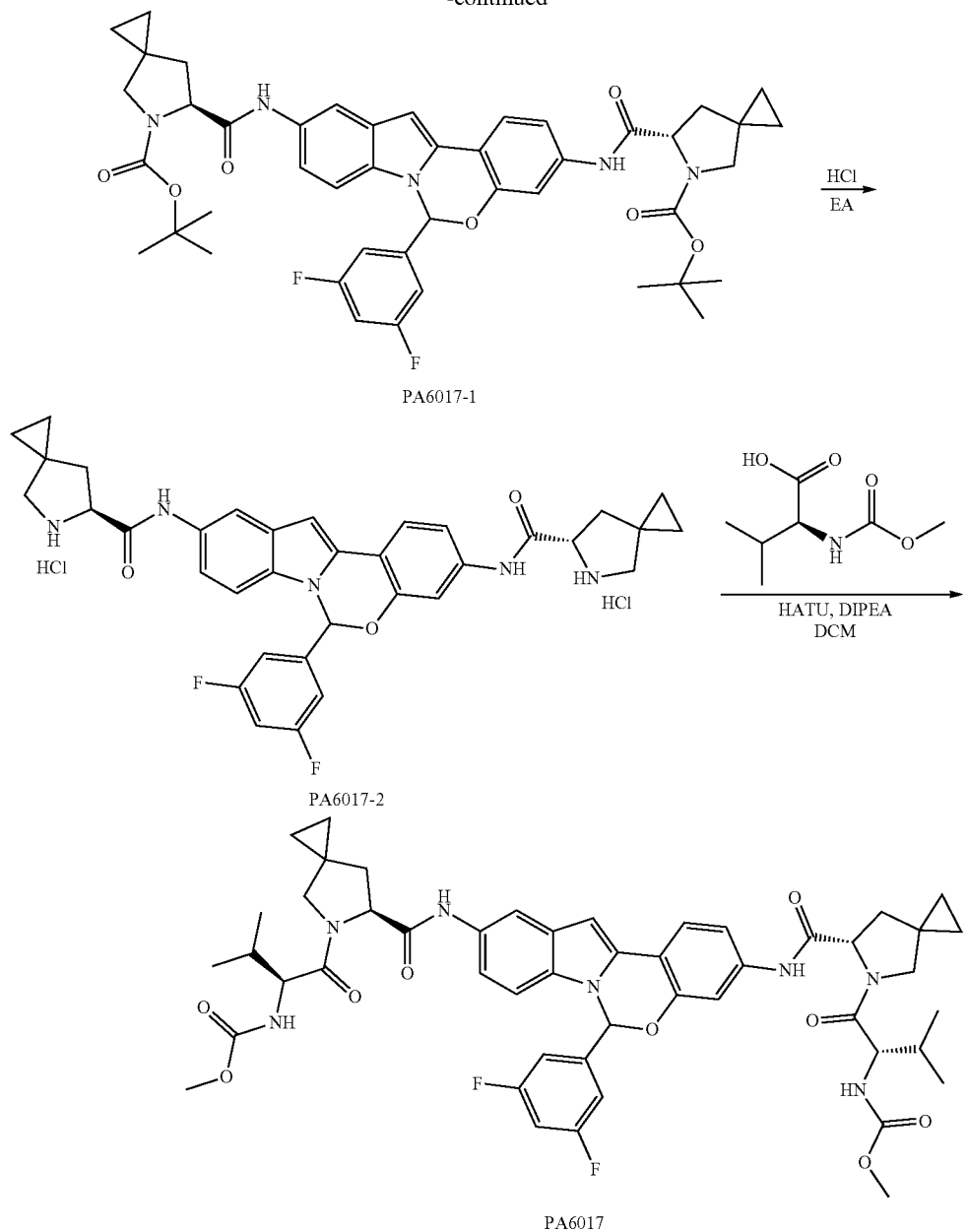

Experiment

Step (1) Synthesis of Compound PA6017-1

75 mg of compound PA6016-4 (0.172 mmol) was dissolved in 8 mL of DCM to produce a solution. 91 mg of (S)-5-t-butoxycarbonyl-5-azaspirol [2.4]heptane-6-carboxyl (0.378 mmol), 196 mg of HATU (0.516 mmol) and 111 mg of DIPEA (0.86 mmol) were added to the solution. The reaction was stirred at room temperature overnight. After the reaction, the resulting product was added with 50 mL of water to produce a mixture. The mixture was extracted with DCM three times each of 100 mL. The organic phases were collected and combined. The combined organic phase was washed with a saturated saline, dried with anhydrous $Na_2SO_4$ and desolventized under vacuum to produce a residue. The residue was separated and purified using silica gel column chromatography with an eluent prepared by DCM and MeOH at a volume ratio of 50:1 to obtain 118 mg of a colorless liquid with a yield of 85%.

Step (2) Synthesis of Compound PA6017-2

117 mg of compound PA6017-1 (0.154 mmol) was dissolved in 3 mL of an EA solution containing 3 M HCl. The reaction was stirred at room temperature overnight and a solid product was precipitated. When the reaction was confirmed to be completed through LC-MS monitoring, the resulting product was filtered to obtain 86 mg of a light brown solid crude product, which was directly employed in the next reaction.

Step (3) Synthesis of Compound PA6017

86 mg of the crude product of compound PA6017-2 was dissolved in 10 mL of DCM to produce a solution. 48 mg of N-methoxycarbonyl-L-valine (0.277 mmol), 144 mg of HATU (0.378 mmol) and 81 mg of DIPEA (0.63 mmol) were added to the solution. The reaction was stirred at room temperature overnight. After the reaction, the resulting product was added with 50 mL of water to produce a mixture. The mixture was extracted with DCM three times each of 100 mL. The organic phases were collected and combined. The combined organic phase was washed with a saturated saline, dried with anhydrous Na₂SO₄ and desolventized under vacuum to produce a residue. The residue was separated and purified using silica gel column chromatography with an eluent prepared by DCM and MeOH at a volume ratio of 50:1 to obtain a crude product. The crude product was purified with Combiflash and lyophilized to obtain 52 mg of a white solid product with a yield of 45%.

Example 7: PA6018

Synthetic Route

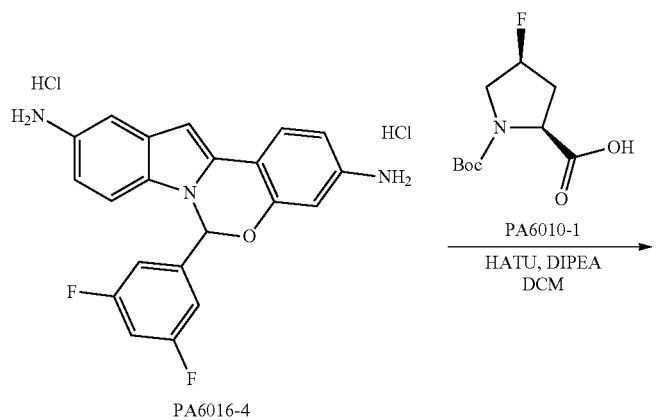

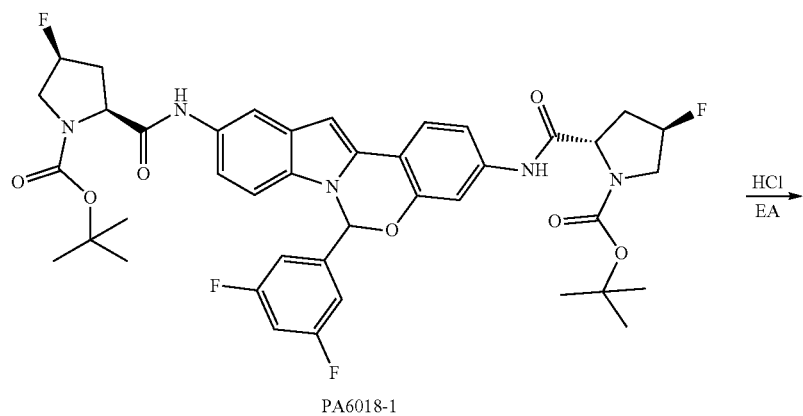

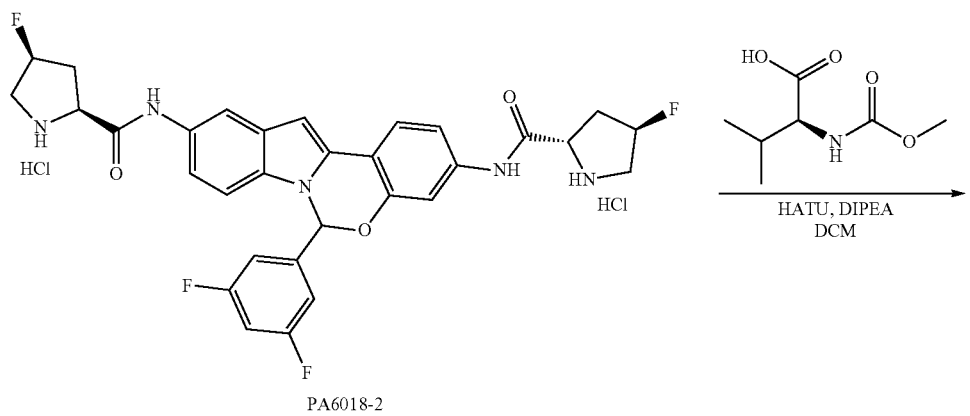

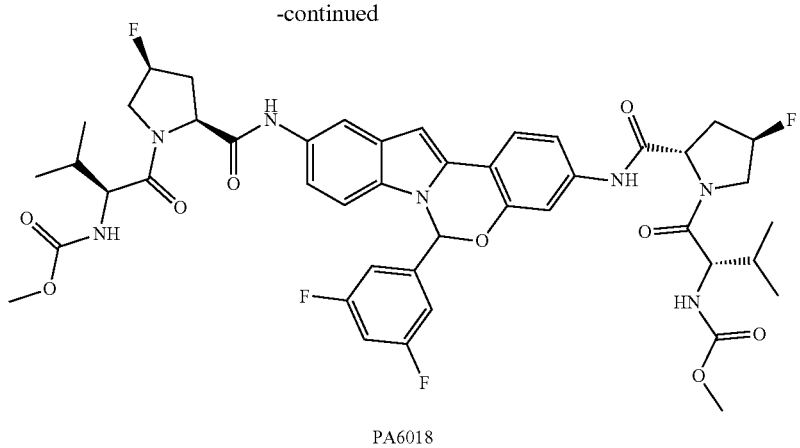

PA6018

Experiment

Step (1) Synthesis of PA6018-1

75 mg of compound PA6016-4 (0.172 mmol) was dissolved in 8 mL of DCM to produce a solution. 88 mg of PA6010-1 (0.378 mmol), 196 mg of HATU (0.516 mmol) and 111 mg of DIPEA (0.86 mmol) were added to the solution. The reaction was stirred at room temperature overnight. After the reaction, the resulting product was added with 50 mL of water to produce a mixture. The mixture was extracted with DCM three times each of 100 mL. The organic phases were collected and combined. The combined organic phase was washed with a saturated saline, dried with anhydrous $Na_2SO_4$ and desolventized under vacuum to produce a residue. The residue was separated and purified using silica gel column chromatography with an eluent prepared by DCM and MeOH at a volume ratio of 50:1 to obtain 120 mg of a colorless liquid with a yield of 88%.

Step (2) Synthesis of Compound PA6018-2

120 mg of compound PA6017-1 (0.151 mmol) was dissolved in 3 mL of an EA solution containing 3 M HCl. The reaction was stirred at room temperature overnight and a solid product was precipitated. When the reaction was confirmed to be completed through LC-MS monitoring, the resulting product was filtered to obtain 79 mg of a light brown solid crude product, which was directly employed in the next reaction.

Step (3) Synthesis of Compound PA6018

79 mg of the crude product of compound PA6018-2 was dissolved in 10 mL of DCM to produce a solution. 46 mg of N-methoxycarbonyl-L-valine (0.261 mmol), 136 mg of HATU (0.357 mmol) and 77 mg of DIPEA (0.595 mmol) were added to the solution. The reaction was stirred at room temperature overnight. After the reaction, the resulting product was added with 50 mL of water to produce a mixture. The mixture was extracted with DCM three times each of 100 mL. The organic phases were collected and combined. The combined organic phase was washed with a saturated saline, dried with anhydrous $Na_2SO_4$ and desolventized under vacuum to produce a residue. The residue was separated and purified using silica gel column chromatography with an eluent prepared by DCM and MeOH at a volume ratio of 50:1 to obtain a crude product. The crude product was purified with Combiflash and lyophilized to obtain 34 mg of a white solid product with a yield of 31%.

Example 8: PA6019

Synthetic Route

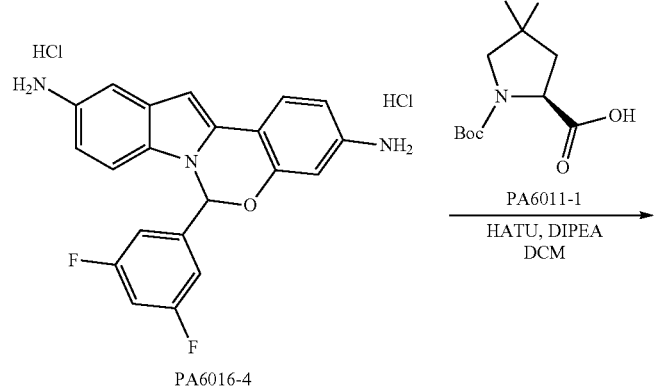

-continued

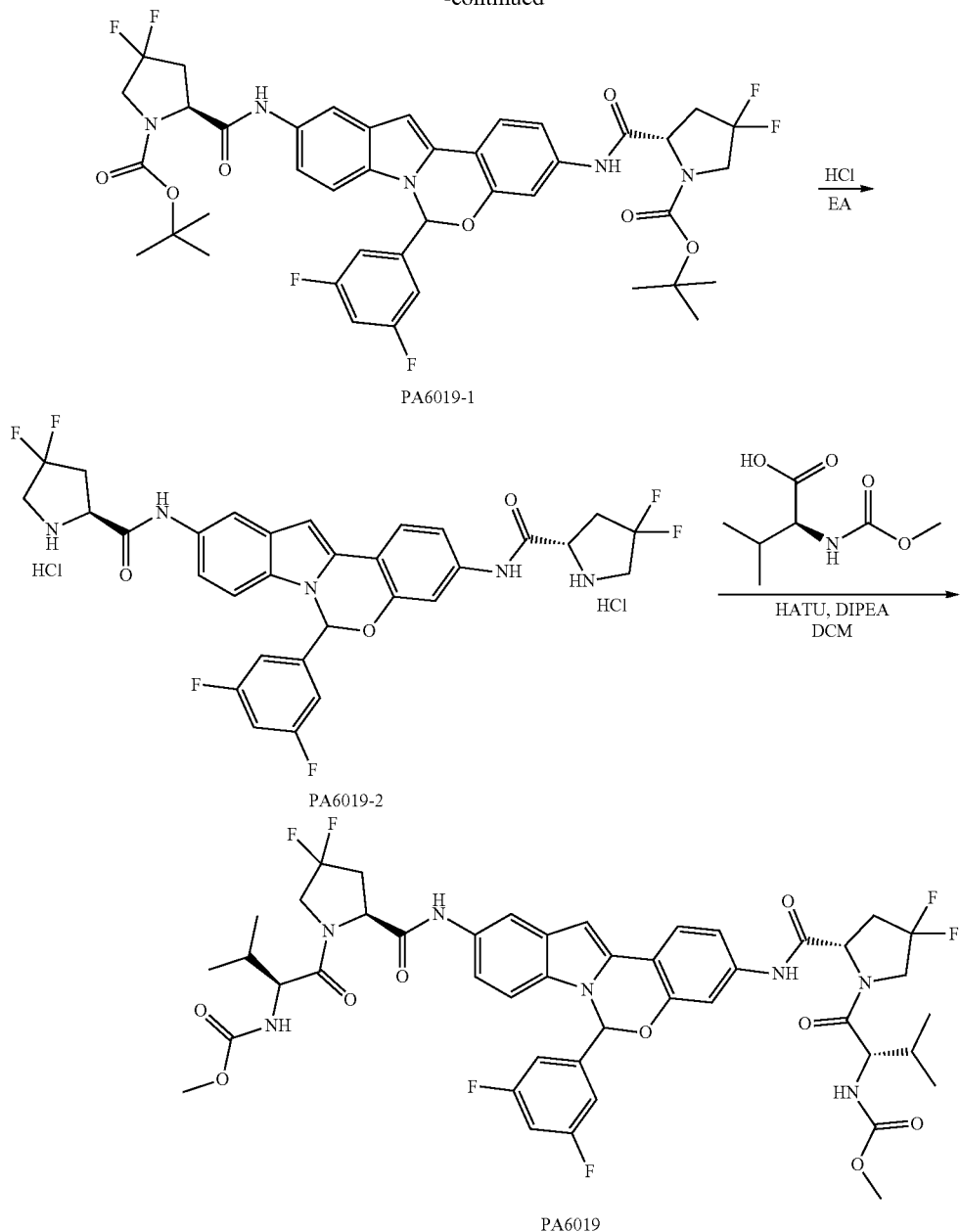

PA6019-1

PA6019-2

PA6019

Experiment

Step (1) Synthesis of Compound PA6019-1

75 mg of compound PA6016-4 (0.172 mmol) was dissolved in 8 mL of DCM to produce a solution. 95 mg of PA6011-1 (0.378 mmol), 196 mg of HATU (0.516 mmol) and 111 mg of DIPEA (0.86 mmol) were added to the solution. The reaction was stirred at room temperature overnight. After the reaction, the resulting product was added with 50 mL of water to produce a mixture. The mixture was extracted with DCM three times each of 100 mL. The organic phases were collected and combined. The combined organic phase was washed with a saturated saline, dried with anhydrous $Na_2SO_4$ and desolventized under vacuum to produce a residue. The residue was separated and purified using silica gel column chromatography with an eluent prepared by DCM and MeOH at a volume ratio of 50:1 to obtain 121 mg of a colorless liquid with a yield of 85%.

Step (2) Synthesis of Compound PA6019-2

121 mg of compound PA6019-1 (0.146 mmol) was dissolved in 3 mL of an EA solution containing 3 M HCl. The reaction was stirred at room temperature overnight and a solid product was precipitated. When the reaction was confirmed to be completed through LC-MS monitoring, the resulting product was filtered to obtain 72 mg of a light brown solid crude product, which was directly employed in the next reaction.

Step (3) Synthesis of Compound PA6019

72 mg of the crude product of compound PA6019-2 was dissolved in 10 mL of DCM to produce a solution. 39 mg of N-methoxycarbonyl-L-valine (0.227 mmol), 117 mg of HATU (0.309 mmol) and 66 mg of DIPEA (0.515 mmol) were added to the solution. The reaction was stirred at room temperature overnight. After the reaction, the resulting product was added with 50 mL of water to produce a mixture. The mixture was extracted with DCM three times each of 100 mL. The organic phases were collected and combined. The combined organic phase was washed with a saturated saline, dried with anhydrous $Na_2SO_4$ and desolventized under vacuum to produce a residue. The residue was separated and purified using silica gel column chromatography with an eluent prepared by DCM and MeOH at a volume ratio of 50:1 to obtain a crude product. The crude product was purified with Combiflash and lyophilized to obtain 23 mg of a white solid product with a yield of 24%.

Example 9: PA6016-B

Synthetic Route

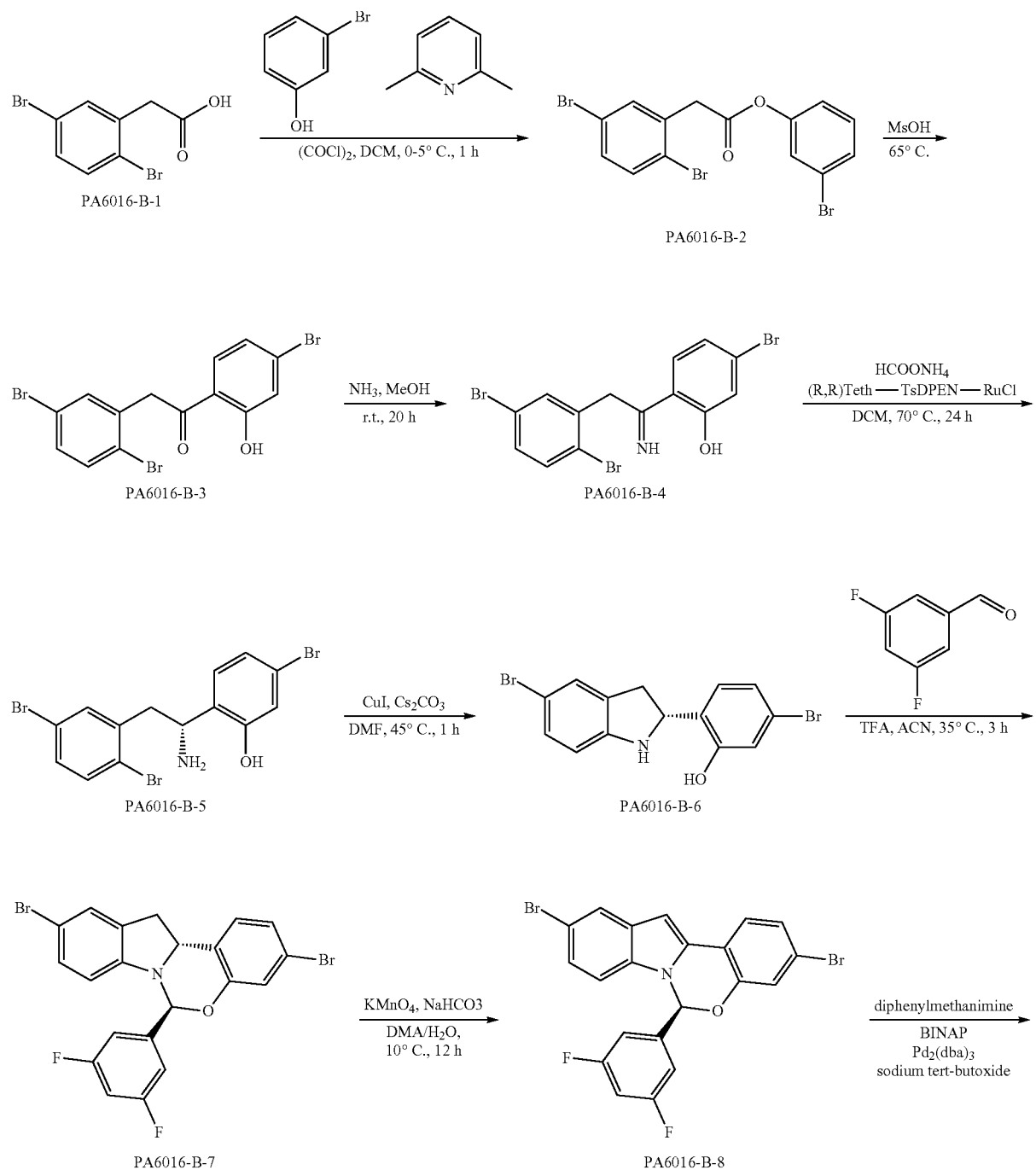

-continued
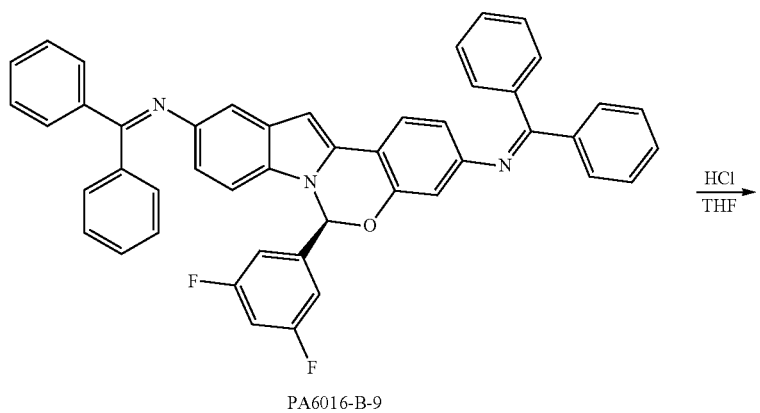
PA6016-B-9
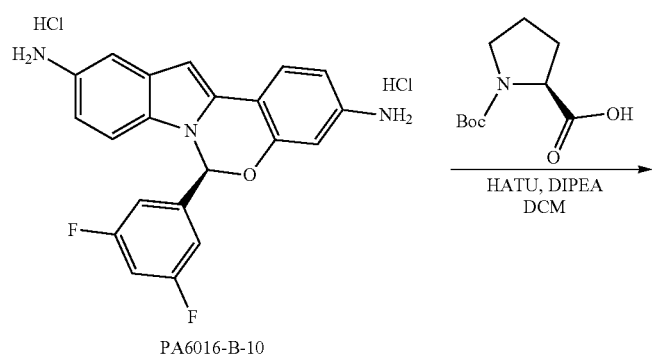
PA6016-B-10
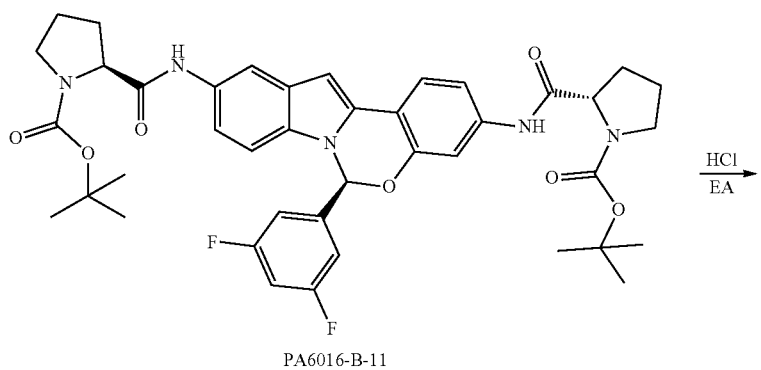
PA6016-B-11
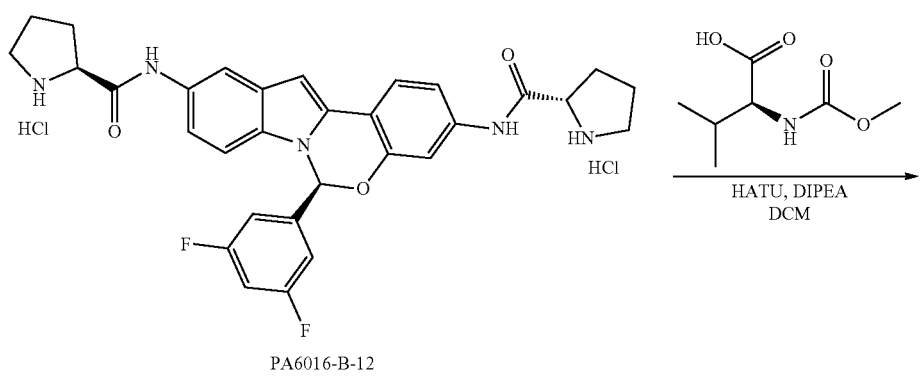
PA6016-B-12

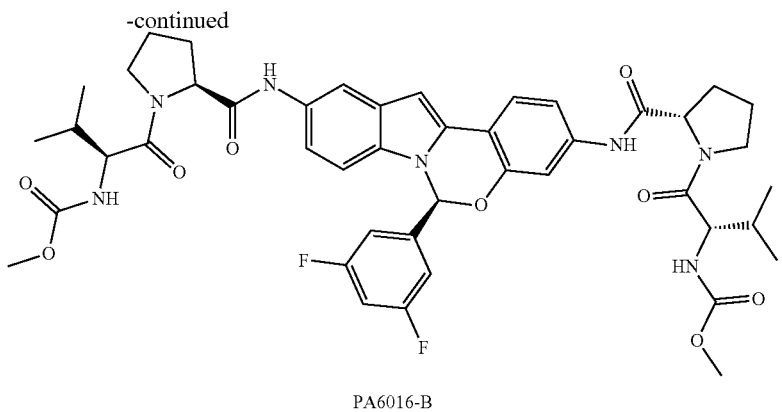

PA6016-B

Experiment

Step (1) Synthesis of Compound PA6016-B-2

100 g of compound PA6016-B-1 (339 mmol) was dissolved in 1200 mL of DCM to produce a solution. 48.3 g of oxalyl chloride (380.6 mmol) was added slowly to the solution for more than 20 minutes to produce a mixture. 1.24 g of DMF (17.0 mmol) was then added slowly to the mixture to carry out a reaction at room temperature for 1 hour. After the reaction, the resulting product was concentrated to a volume of 500 mL to produce an acyl chloride solution. 62.9 g of m-bromophenol (356 mmol), 530 mL of DCM and 2,6-lutidine were mixed in a 2000 mL three-necked reaction flask to produce a blend. The blend was cooled to 0-5° C., and then was dripped with the acyl chloride solution. The reaction was maintained at 0-5° C. during the dripping process. After the dripping, the reaction was stirred at 0-5° C. for 1 hour. After the reaction, the resulting product was dripped slowly with 530 mL of 1 N HCl to obtain an organic and aqueous phase. The organic phase was washed with 530 mL of water and dried using rotary evaporation to produce a residue. The residue was mixed uniformly with 300 mL of acetonitrile to produce a mixture. 318 mL of water was slowly dripped into the mixture and a large amount of precipitates was formed to produce a turbid liquid. The resulting turbid liquid was filtrated to obtain a filter cake. The filter cake was washed with 318 mL of a mixture of acetonitrile and water at a ratio of 1:1, and dried to obtain 146 g of a solid product with a yield of 91%. MS-ESI: m/z, 449[M+1]$^+$.

Step (2) Synthesis of Compound PA6016-B-3

10.61 g of methanesulfonic anhydride (59.1 mmol) was dissolved in 384 mL of methanesulfonic acid to produce a solution. The solution was stirred at 90° C. for 1 hour and then cooled to 65° C. 132.5 g of PA6016-B-2 (295 mmol) was slowly added to the solution for a reaction at 65° C. for 22-24 hours. After the reaction, the resulting product was cooled to room temperature. 1115 mL of a mixture of isopropanol and water at a ratio of 3:1 was slowly dripped into the resulting product and a large amount of precipitates was formed to produce a turbid liquid. The resulting turbid liquid was filtrated to obtain a filter cake. The filter cake was washed with 418 mL of a mixture of isopropanol and water at a ratio of 1:1 and dried to obtain 108.0 g of a white solid product with a yield of 82%. MS-ESI: m/z, 451 [M+1]$^+$.

Step (3) Synthesis of Compound PA6016-B-4

78.2 mg of compound PA6016-B-3 (174 mmol) was dissolved in 423 mL of a methanol solution containing 7 N ammonia (2.96 mmol) to produce a solution. The solution was stirred at room temperature for a reaction for 20 hours. After the reaction, the resulting product was directly filtrated to obtain a filter cake. The filter cake was washed with a small amount of methanol and dried to obtain 73.3 g of a yellow solid product with a yield of 94%. MS-ESI: m/z, 448[M+1]$^+$.

Step (4) Synthesis of Compound PA6016-B-5

29.6 g of compound PA6016-B-4 (66.1 mmol) was dissolved in 326 mL of DCM to produce a solution. 9.17 g of ammonium formate (145 mmol) and 123 mg of a catalyst (R,R)Teth-TsDPEN-RuCl (CAS number: 1192620-83-9, 0.198 mmol) were slowly added to the solution to produce a mixture. The mixture was reacted at 70° C. under sealing for 24 hours with pressure in a reaction flask at 39 psi. After the reaction, the resulting product was cooled to room temperature and adjusted to pH of 7.5 with a 10% sodium bicarbonate solution to obtain an organic and aqueous phase. The organic phase was washed with water twice each of 90 mL and dried using rotary evaporation to produce a residue. The residue was mixed uniformly with 150 mL of acetonitrile to produce a blend. The blend was slowly dripped with 120 mL of water at room temperature and a large amount of precipitates was formed to produce a turbid liquid. The turbid liquid was filtered to obtain a filter cake. The filter cake was washed with 20 mL of a mixture of acetonitrile and water at a ratio of 1:1 and dried to obtain 26.2 g of a white solid product with a yield of 88%. MS-ESI: m/z, 450 [M+1]$^+$.

Step (5) Synthesis of Compound PA6016-B-6

33.0 g of compound PA6016-B-5 (73.3 mmol) was dissolved in 165 mL of DMF to produce a solution. 47.8 g of cesium carbonate (147 mmol) and 698 mg of CuI (3.67 mmol) was slowly added to the solution to produce a mixture. The mixture was reacted at 45° C. for 1 hour. After the reaction, the resulting product was added with 100 mL of ethyl acetate and immediately adjusted to pH of 7.5 with a 25% aqueous ammonium chloride solution to obtain an organic and aqueous phase. The aqueous phase was stripped with 70 mL of ethyl acetate. The organic phases were combined. The combined organic phase was washed with 120 mL of a 10% saline and then with 120 mL of water, and dried using rotary evaporation to produce a residue. The residue was mixed uniformly with 150 mL of acetonitrile to produce a blend. The blend was slowly dripped with 150 mL of water and a large amount of precipitates was formed to produce a turbid liquid. The turbid liquid was filtered to obtain a filter cake. The filter cake was washed with 30 mL of a mixture of acetonitrile and water at a ratio of 1:1 and dried to obtain 24.6 g of a white solid product with a yield of 91%. MS-ESI: m/z, 370 [M+1]$^+$.

Step (6) Synthesis of Compound PA6016-B-7

1.17 g of compound PA6016-B-6 (3 mmol) was dissolved in 15 mL of acetonitrile to produce a solution. 0.64 g of 3,5-difluorobenzaldehyde (4.5 mmol) and 0.1 g of trifluoroacetic acid were added to the solution at room temperature. The reaction was stirred at 36° C. for 3 hours under nitrogen. After the reaction, the resulting product was cooled to room temperature and added with 2 mL of a saturated sodium carbonate and 15 mL of water to produce a mixture. The mixture was stirred for 3 hours and a grey red solid product was precipitated to produce a turbid liquid. The turbid liquid was filtered under vacuum to obtain 1.42 g of a solid crude product with a yield of 91%, which can be directly employed in the next reaction. MS: 494.2 (M+H)$^+$.

Step (7) Synthesis of Compound PA6016-B-8

1.4 g of compound PA6016-B-7 (2.8 mmol) was dissolved in 15 mL of N-dimethyl acetamide to produce a solution. 2 mL of water, 1.06 mg of Na$_2$HCO$_3$ (0.01 mol) and 0.98 g of potassium permanganate (6 mmol) were added to the solution. The reaction was stirred at room temperature overnight. After the reaction, the resulting product was added with 10 mL of a saturated sodium bisulfite solution and stirred for half an hour until black was completely faded to produce a blend. The blend was extracted with ethyl acetate three times each of 150 mL. The extracted three organic phases were collected and combined. The combined organic phase was washed with a saturated saline, dried with anhydrous Na$_2$SO$_4$ and desolventized under vacuum to produce a residue. The residue was separated and purified using silica gel column chromatography with an eluent prepared by PE and EA at a volume ratio of 50:1 to obtain 1.11 g of a white crystal with a yield of 80%. MS: 492.0 (M+H)+.

Step (8) Synthesis of Compound PA6016-B-9

1.11 g of compound PA6016-B-8 (2.27 mmol) was dissolved in 20 mL of toluene to produce a solution. 1.23 g of diphenylmethanimine (6.6 mmol), 110 mg of Pd$_2$(dba)$_3$ (0.1 mmol), 210 mg of BINAP (0.33 mmol) and 650 mg of sodium tert-butoxide (6.6 mmol) were added to the solution. The reaction was stirred under nitrogen protection at 100° C. overnight. The resulting product was cooled to room temperature and added with 100 mL of water to produce a mixture. The mixture was extracted with DCM three times each of 150 mL. The organic phases were collected and combined. The combined organic phase was washed with a saturated saline, dried with anhydrous Na$_2$SO$_4$ and desolventized under vacuum to produce a residue. The residue was separated and purified using silica gel column chromatography with an eluent prepared by PE and DCM at a volume ratio of 1:1 to obtain 1.42 g of a yellow solid product with a yield of 90%. MS: 692 (M+H)$^+$.

Step (9) Synthesis of Compound PA6016-B-10

820 mg of compound PA6016-B-9 (1.18 mmol) was dissolved in 5 mL of THF to produce a solution. The solution was slowly dripped with 0.6 mL of 6 N HCl and reacted at room temperature for 2 hours. After the reaction, the resulting product was added with 20 mL of water and 5 mL of EA to obtain an organic phase and an aqueous phase. The aqueous phase was extracted with EA twice each of 5 mL. The aqueous phase after extraction was adjusted to pH of 9.5 with ammonia and a large amount of solid product was precipitated to produce a turbid liquid. The turbid liquid was filtered to obtain a filter cake. The filter cake was washed with a solvent of EA and PE at a ratio of 1:3 to obtain 400 mg of a light yellow solid product with a yield of 93%. MS: 364.2 (M+H)$^+$.

Step (10) Synthesis of Compound PA6016-B-11

400 mg of compound PA6016-B-10 (1.1 mmol) was dissolved in 10 mL of DCM to produce a solution. 0.53 g of t-butoxycarbonyl-L-proline (2.5 mmol), 1.3 g of HATU (3.3 mmol) and 850 mg of DIPEA (6.1 mmol) were added to the solution. The reaction was stirred at room temperature overnight. After the reaction, the resulting product was added with 50 mL of water to produce a mixture. The mixture was extracted with DCM three times each of 100 mL. The organic phases were collected and combined. The combined organic phase was washed with a saturated saline, dried with anhydrous Na$_2$SO$_4$ and desolventized under vacuum to produce a residue. The residue was separated and purified using silica gel column chromatography with an eluent prepared by PE and EA at a volume ratio of 1:1 to obtain 450 mg of a white solid product with a yield of 54%. MS: 758.4 (M+H)$^+$.

Step (11) Synthesis of Compound PA6016-B-12

400 mg of compound PA6016-B-11 (0.528 mmol) was dissolved in 3 mL of an EA solution containing 3 M HCl to produce a solution. The solution was stirred at room temperature overnight for a reaction and a solid product was precipitated. When the reaction was confirmed to be completed through LC-MS monitoring, the resulting product was filtered to obtain 250 mg of a light yellow solid crude product with a yield of 85%, which was directly employed in the next reaction. MS: 558.3 (M+H)$^+$.

Step (12) Synthesis of Compound PA6016-B 190 mg of crude product of compound PA6016-B-12 was dissolved in 10 mL of DCM to produce a solution. 280 mg of N-methoxycarbonyl-L-valine (1.6 mmol), 646 mg of HATU (1.7 mmol) and 250 mg of DIPEA (1.944 mmol) were added to the solution. The reaction was stirred at room temperature overnight. After the reaction, the resulting product was added with 50 mL of water to produce a mixture. The mixture was extracted with DCM three times each of 100 mL. The organic phases were collected and combined. The combined organic phase was washed with a saturated saline, dried with anhydrous Na$_2$SO$_4$ and desolventized under vacuum to produce a residue. The residue was separated and purified using silica gel column chromatography with an eluent prepared by DCM and MeOH at a volume ratio of 50:1 to obtain 220 mg of a white solid product, which may be further purified to obtain 80 mg of a pure product of compound PA6016-B using preparative liquid chromatography.

Example 10: PA6030
Synthetic Route
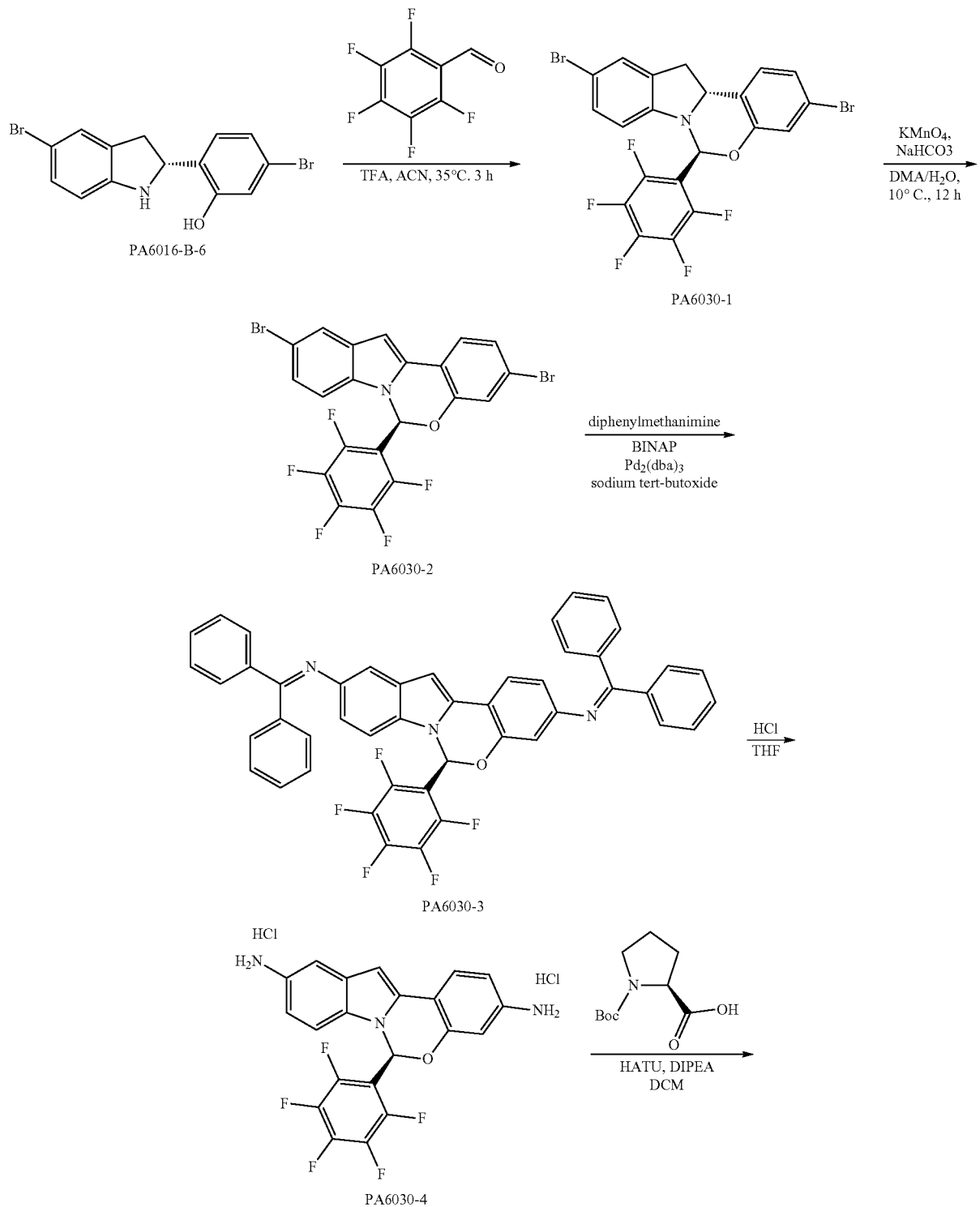

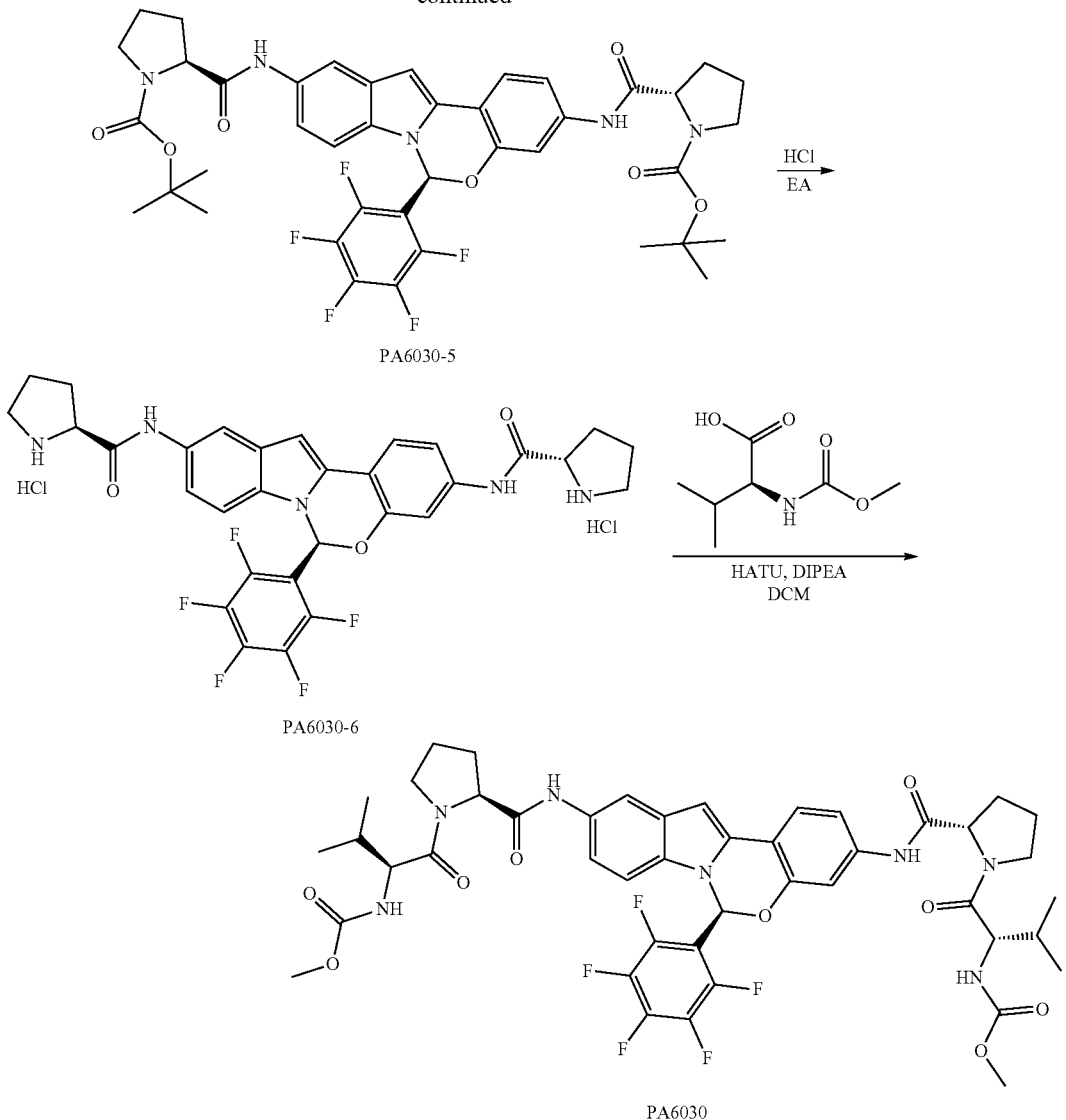

PA6030

Experiment

Step (1) Synthesis of Compound PA6030-1

29.0 mg of compound PA6016-B-6 (78.57 mmol) was dissolved in 30 mL of acetonitrile to produce a solution. The solution was added with 21.57 g of pentafluorobenzaldehyde (110.0 mmol) and then slowly dripped with 0.45 g of trifluoroacetic acid (3.95 mmol). After the dripping, the reaction was stirred at 30-35° C. for 3 hours. After the reaction, the resulting product was cooled to 20-25° C. and added slowly with 58 mL of water to produce a mixture. The mixture was then slowly dripped with 13.2 mL of a 5% sodium bicarbonate solution and stirred for 3 hours to produce a crystallization solution. The crystallization solution was filtered to obtain a filter cake. The filter cake was washed with 87 mL of a mixture of acetonitrile and water at a ratio of 2:1 and then washed with 58 mL of water, and dried to obtain 39.8 g of a white solid product with a yield of 93%. MS-ESI: m/z, 548[M+1]$^+$.

Step (2) Synthesis of Compound PA6030-2

45 g of compound PA6030-1 (82.25 mmol) was dissolved in 450 mL of N,N-dimethyl acetamide to produce a solution. 20.8 g of sodium bicarbonate (247.6 mmol) was added to the solution to produce a mixture. The mixture was cooled to 10° C. and was added slowly with 24.91 g of potassium permanganate (157.7 mmol) and 100 mL of water at a temperature below 15° C. After that, the reaction was stirred at 10° C. for 12 hours. After the reaction, the resulting product was added with 800 mL of ethyl acetate to produce a blend. The blend was stirred at room temperature for 1 hour and then dripped slowly with a freshly-prepared sodium bisulfite solution (prepared by dissolving 24.03 g of sodium bisulfate in 400 mL of water) at 30° C. The reaction was stirred for 1 hour and then was stood for liquid separation to obtain an organic and an aqueous phase. The aqueous phase was stripped with 400 mL of ethyl acetate. The organic phases were combined. The combined phase was washed with a 10% saline three times each of 200 mL and dried with rotary evaporation to produce a residue. The residue was mixed uniformly with 400 mL of isopropanol to produce a mixed solution. The mixed solution was dripped slowly with 400 mL of water at room temperature and a large amount of precipitates were formed to produce a turbid liquid. The turbid liquid was filtered to obtain a filter cake. The filter cake was washed with 200 mL of a solution of isopropanol and water at a ratio of 1:1 and dried to obtain 37.2 g of a white solid product with a yield of 83%. MS-ESI: m/z, 546[M+1]$^+$.

Step (3) Synthesis of Compound PA6030-3

0.25 g of compound PA6030-2 (0.460 mmol) was dissolved in 10 mL of toluene to produce a solution. 0.250 g of diphenylmethanimine (1.38 mmol), 21 mg of Pd$_2$(dba)$_3$ (0.032 mmol), 43 mg of BINAP (0.069 mmol) and 133 mg of sodium tert-butoxide (1.38 mmol) were added to the solution. The reaction was stirred under nitrogen protection at 100° C. overnight. The resulting product was cooled to room temperature and added with 100 mL of water to produce a mixture. The mixture was extracted with DCM three times each of 150 mL. The organic phases were collected and combined. The combined organic phase was washed with a saturated saline, dried with anhydrous Na$_2$SO$_4$ and desolventized under vacuum to produce a residue. The residue was separated and purified using silica gel column chromatography with an eluent prepared by PE and DCM at a volume ratio of 1:1 to obtain 220 mg of a yellow solid product with a yield of 64%.

Step (4) Synthesis of Compound PA6030-4

0.22 g of compound PA6030-3 (0.295 mmol) was dissolved in 5 mL of THF to produce a solution. 6 N hydrochloric acid was dripped into the solution to start a reaction and at a rate of two drops per hour. The reaction was carried out for 12 hours and the progress thereof was monitored at any time. After the reaction, a light yellow solid product was precipitated in the resulting product and obtained with a filtration. The resulting solid product was washed with THF and dried under vacuum to obtain 80 mg of a final light yellow solid product with a yield of 55%.

Step (5) Synthesis of Compound PA6030-5

80 mg of compound PA6030-4 (0.163 mmol) was dissolved in 5 mL of DCM to produce a solution. 90 mg of t-butoxycarbonyl-L-proline (0.360 mmol), 186 mg of HATU (0.489 mmol) and 126 mg of DIPEA (0.987 mmol) were added to the solution. The reaction was stirred at room temperature overnight. After the reaction, the resulting product was added with 50 mL of water to produce a mixture. The mixture was extracted with DCM three times each of 100 mL. The organic phases were collected and combined. The combined organic phase was washed with a saturated saline, dried with anhydrous Na$_2$SO$_4$ and desolventized under vacuum to produce a residue. The residue was separated and purified using silica gel column chromatography with an eluent prepared by PE and EA at a volume ratio of 2:1 to obtain 150 mg of a yellow solid product with a yield of 95%.

Step (6) Synthesis of Compound PA6030-6

150 mg of compound PA6030-5 (0.185 mmol) was dissolved in 3 mL of an EA solution containing 3 M HCl. The reaction was stirred at room temperature overnight and a solid product was precipitated. When the reaction was confirmed to be completed through LC-MS monitoring, the resulting product was filtered to obtain 80 mg of an off-white solid crude product, which was directly employed in the next reaction.

Step (7) Synthesis of Compound PA6030

80 mg of the crude product of compound PA6030-6 was dissolved in 10 mL of DCM to produce a solution. 45 mg of N-methoxycarbonyl-L-valine (0.257 mmol), 113 mg of HATU (0.351 mmol) and 90 mg of DIPEA (0.702 mmol) were added to the solution. The reaction was stirred at room temperature overnight. After the reaction, the resulting product was added with 50 mL of water to produce a mixture. The mixture was extracted with DCM three times each of 100 mL. The organic phases were collected and combined. The combined organic phase was washed with a saturated saline, dried with anhydrous Na$_2$SO$_4$ and desolventized under vacuum to produce a residue. The residue was separated and purified using silica gel column chromatography with an eluent prepared by PE and EA at a volume ratio of 1:3 to obtain 60 mg of a white solid product with a yield of 35%.

Example 11: PA6031

Synthetic Route

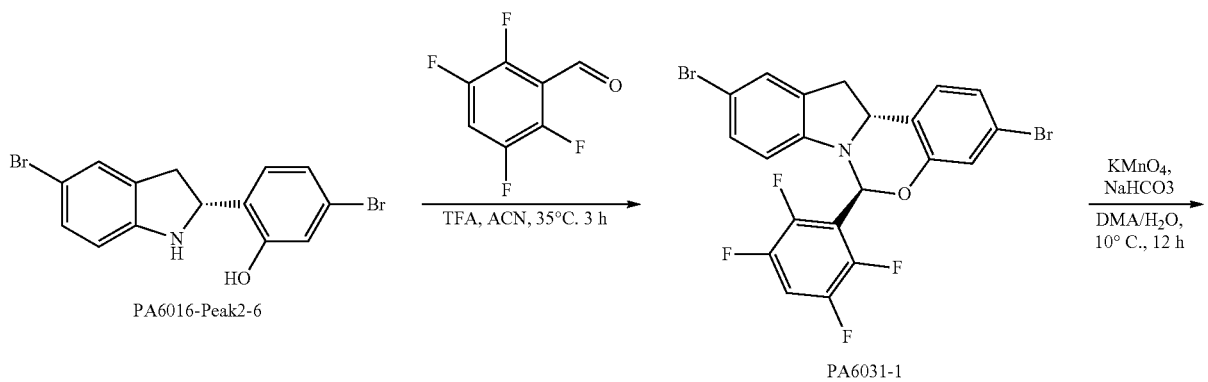

PA6031-1

-continued
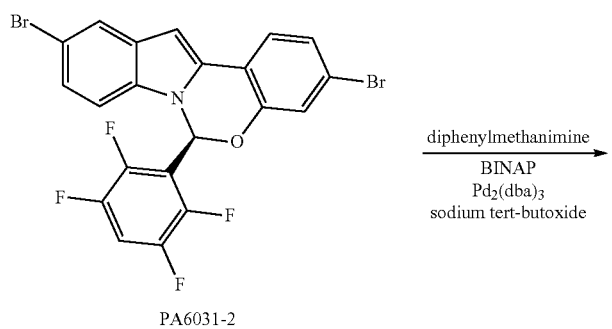
PA6031-2
diphenylmethanimine
BINAP
Pd$_2$(dba)$_3$
sodium tert-butoxide
→
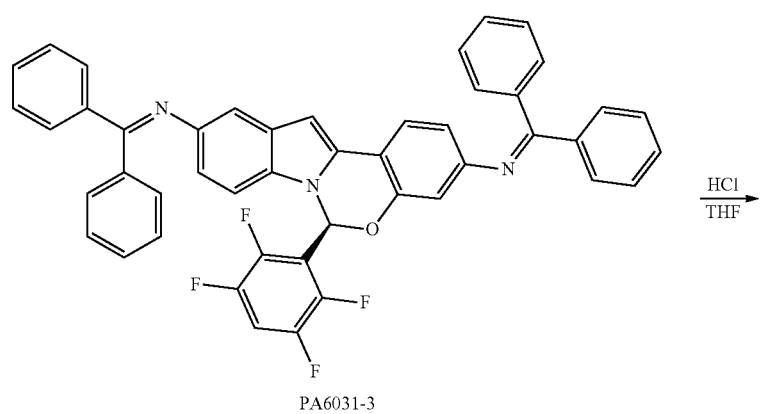
PA6031-3
HCl
THF
→
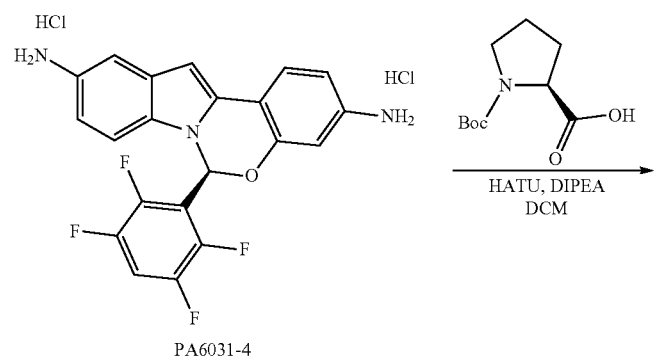
PA6031-4
HATU, DIPEA
DCM
→
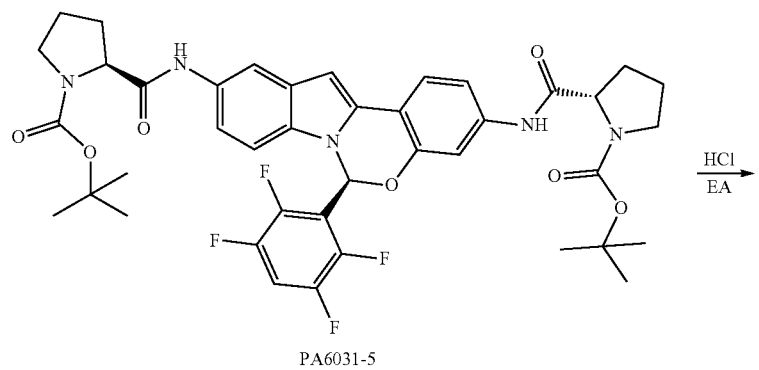
PA6031-5
HCl
EA
→

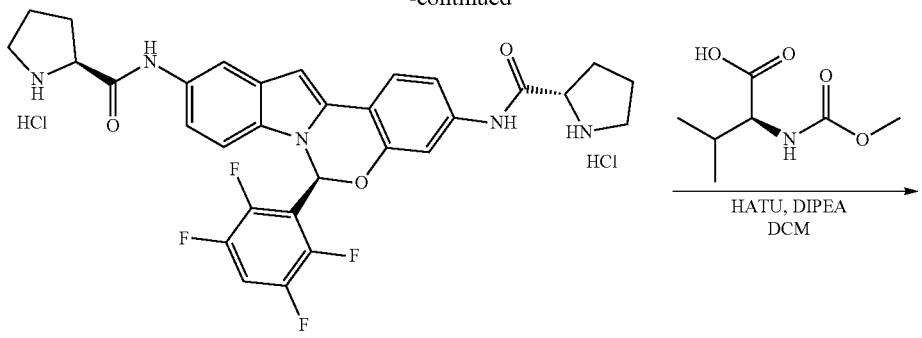

PA6031-6

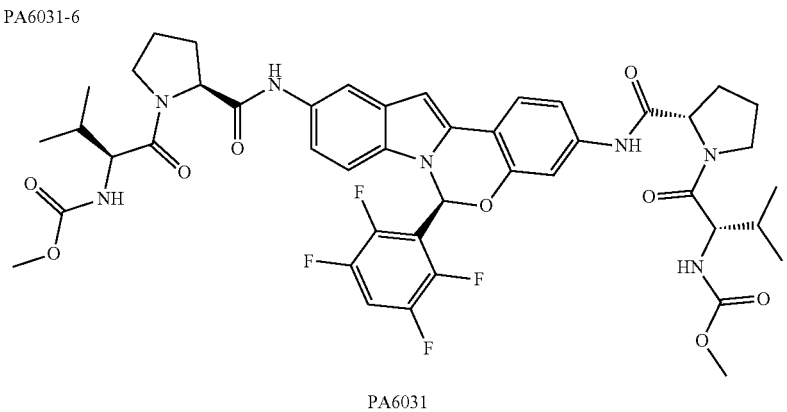

PA6031

Experiment

Step (1) Synthesis of Compound PA6031-1

1 g of compound PA6016-B-6 (2.71 mmol) was dissolved in 10 mL of $CH_3CN$ to produce a solution. The solution was added with 675 mg of 2,3,5,6-tetrafluorobenzaldehyde (3.79 mmol) and slowly added with 15.96 mg of TFA (0.14 mmol). The reaction was heated to 35° C. under nitrogen protection and maintained for 3 hours. After the reaction, the resulting product was cooled to 25° C. and added with 4 mL of water and 4 mL of a saturated $NaHCO_3$ solution to produce a mixture. The mixture was stirred for 3 hours and filtered under vacuum to obtain a filter cake. The filter cake was respectively washed with 3 mL and 2 mL of a mixed solvent of $CH_3CN$ and $H_2O$ at a volume ratio of 2:1 and dried to obtain 1.592 g of a grey-purple solid crude product.

Step (2) Synthesis of Compound PA6031-2

1 g of compound PA6031-1 (1.89 mmol) was dissolved in 15 mL of DMA to produce a solution. 476.28 mg of $NaHCO_3$ (5.67 mmol) and 2.5 mL of water were added to the solution to produce a mixture. 567.22 mg of $KMnO_4$ (3.59 mmol) was added to the mixture in portions within 20 minutes under nitrogen protection. The reaction was stirred overnight. After the reaction, the resulting product was added with 100 mL of EA and 100 mL of a saturated $NaHSO_3$ solution to produce a blend. The blend was stirred for 1 hour to obtain an organic and an aqueous phase. The aqueous phase was extracted with EA three times each of 30 mL. The organic phases were combined. The combined organic phase was washed with a saturated saline, dried with 5 g of anhydrous $Na_2SO_4$, filtered under vacuum and dried using rotary evaporation to obtain 0.93 g of a purple solid product. The purple solid product was washed with DCM to obtain 644 mg of a final purple solid product with a yield of 64.66%.

Step (3) Synthesis of Compound PA6031-3

644 mg of compound PA6031-2 (1.22 mmol) was dissolved in 12 mL of toluene to produce a solution. 666 mg of diphenylmethanimine (3.67 mmol), 65 mg of $Pd_2(dba)_3$ (0.07 mmol), 119 mg of BINAP (0.19 mmol) and 353 mg of sodium tert-butoxide (3.67 mmol) were added to the solution. Then reaction system was vacuumed and nitrogen was introduced for three replacements. The reaction was stirred at 90° C. overnight. After that, the resulting product was dried at 40° C. using vacuum rotary evaporation to remove toluene and produce a residue. The residue product was dissolved in 100 mL of DCM to produce a mixture. The mixture was washed three times with water each of 30 mL and washed with 30 mL of a saturated saline, dried with anhydrous $Na_2SO_4$, filtered under vacuum and dried using rotary evaporation to obtain a tan solid product. The tan solid product was separated and purified through a chromatography column with an eluent of PE and EA at a ratio of 10:1 to obtain 340 mg of a final tan solid product with a yield of 38.29%.

Step (4) Synthesis of Compound PA6031-4

340 mg of compound PA6031-3 (0.47 mmol) was dissolved in 4 mL of THF to produce a solution. 6 drops of 6 M HCl aqueous solution was dripped to the solution in three portions within 1 hour. The reaction was stirred at room temperature. After that, the resulting product was filtered under vacuum to obtain a filter cake. The filter cake was washed with 2 mL of THF and dried to obtain 190 mg of a tan solid product with a yield of 86.36%.

Step (5) Synthesis of Compound PA6031-5

190 mg of compound PA6031-4 (0.40 mmol) was dissolved in 10 mL of DCM to produce a solution. 223 mg of t-butoxycarbonyl-L-proline (0.89 mmol), 468 mg of HATU (1.23 mmol) and 318 mg of DIPEA (2.46 mmol) were added to the solution. The reaction was stirred at room temperature overnight. After the reaction, the resulting product was added with 100 mL of DCM to produce an organic and an aqueous phase. The organic phase was washed with water three times each of 30 mL and washed with 30 mL of a saturated saline once, dried with 5 g of anhydrous $Na_2SO_4$ for half an hour, filtered under vacuum and dried at 35° C. using vacuum rotary evaporation to obtain 476 mg of a light yellow solid product. The light yellow solid product was separated and purified through a chromatography column with an eluent prepared by PE and EA at a volume ratio of 2:1 to obtain 249 mg of a final light yellow solid product.

Step (6) Synthesis of Compound PA6031-6

249 mg of compound PA6031-5 (0.31 mmol) was dissolved in 2 mL of EA to produce a solution. 4 mL of an EA solution containing hydrochloride acid was added to the solution. The reaction was stirred at room temperature overnight. After the reaction, the resulting product was filtered under vacuum to obtain a filter cake. The filter cake was washed with 2 mL of EA and dried to obtain 173 mg of a light yellow solid product with a yield of 82.78%.

Step (7) Synthesis of Compound PA6031

173 mg of compound PA6031-6 (0.26 mmol) was dissolved in 10 mL of DCM to produce a solution. 100 mg of Moc-L-valine (0.57 mmol), 297 mg of HATU (0.78 mmol) and 202 mg of DIPEA (1.56 mmol) were added to the solution. The reaction was stirred at room temperature overnight. After the reaction, the resulting product was added with 100 mL of DCM to produce an organic and an aqueous phase. The organic phase was washed with water three times each of 30 mL and with 30 mL of a saturated saline once, dried with 5 g of anhydrous $Na_2SO_4$ for half an hour, filtered under vacuum and dried using rotary evaporation to obtain 357 mg of a light yellow solid product. The light yellow solid product was separated and purified through a chromatography column with an eluent prepared by PE and EA at a volume ratio of 1:1 to obtain 178 mg of an off-white solid product with a yield of 75.74%.

Example 12: PA6032

Synthetic Route

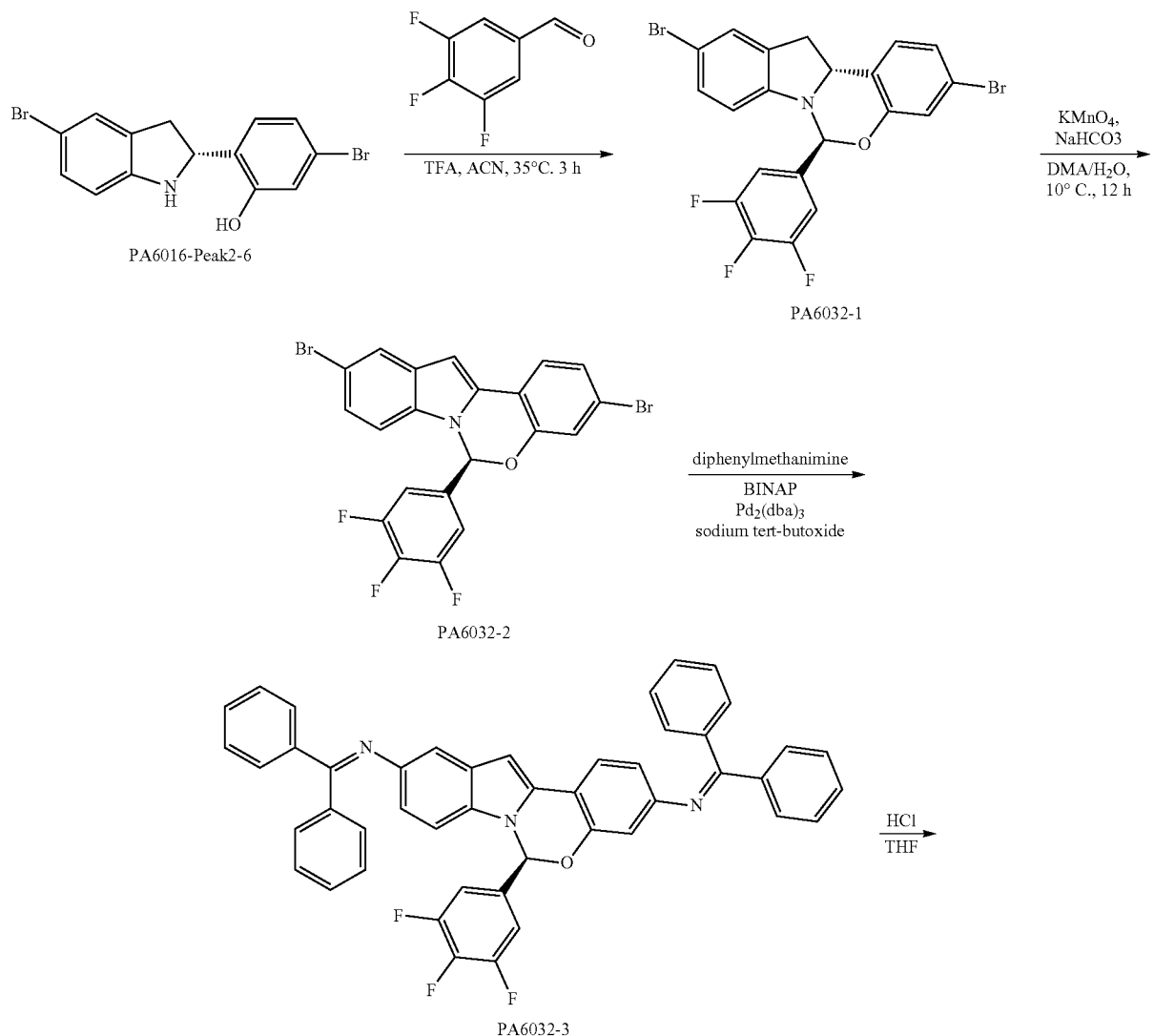

-continued
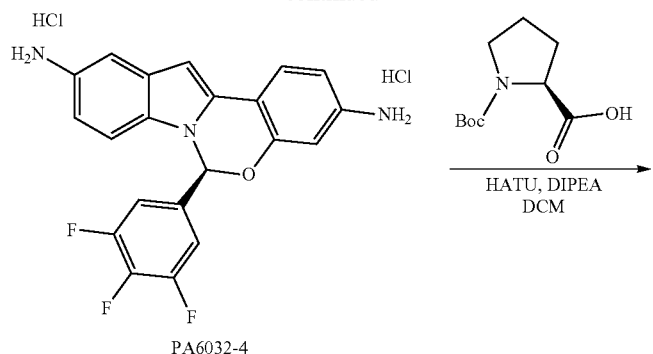
PA6032-4
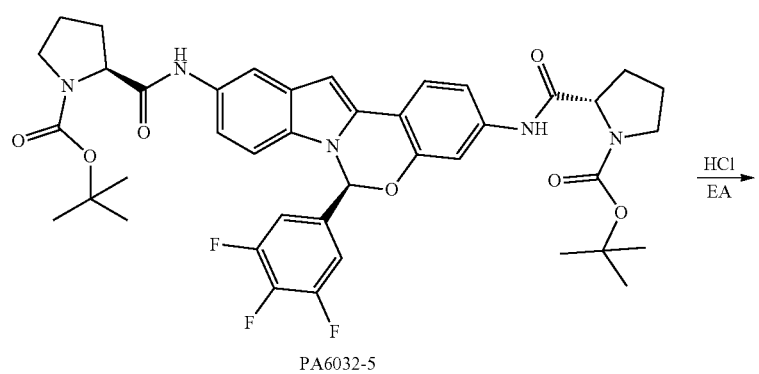
PA6032-5
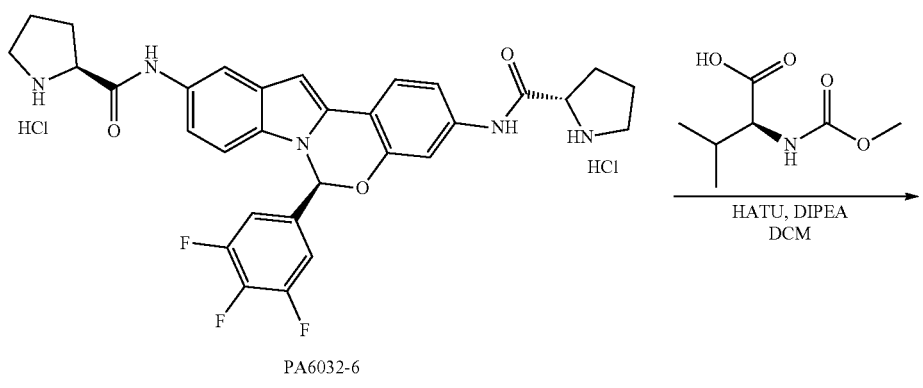
PA6032-6
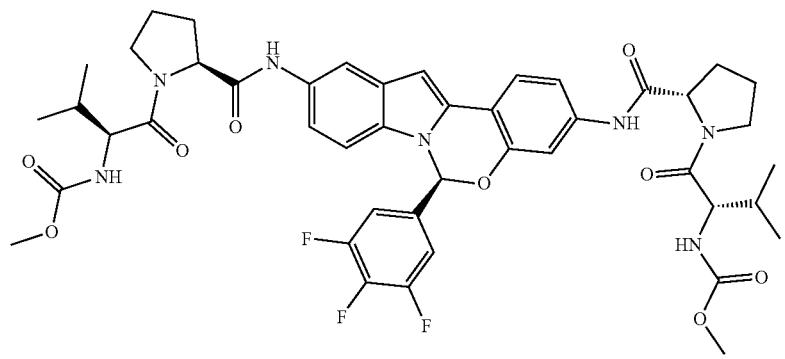
PA6032

Experiment

Step (1) Synthesis of Compound PA6032-1

29.0 g of compound PA6016-B-6 (78.57 mmol) was dissolved in 30 mL of acetonitrile to produce a solution. The solution was added with 17.61 g of trifluorobenzaldehyde (110.0 mmol) and then slowly dripped with 0.45 g of trifluoroacetic acid (3.95 mmol). After the dripping, the reaction was stirred at 30-35° C. for 3 hours. After the reaction, the resulting product was cooled to 20-25° C. and slowly added with 58 mL of water to produce a mixture. The mixture was then slowly dripped with 13.2 mL of a 5% sodium bicarbonate solution and stirred for 3 hours to produce a crystallization solution. The crystallization solution was filtered to obtain a filter cake. The filter cake was washed with 87 mL of a mixture of acetonitrile and water at a ratio of 2:1 and then washed with 58 mL of water, and dried to obtain 37.4 g of a white solid product with a yield of 93%. MS-ESI: m/z, 512 [M+1]$^+$.

Step (2) Synthesis of Compound PA6032-2

45 g of compound PA6032-1 (88.05 mmol) was dissolved in 450 mL of N,N-dimethyl acetamide to produce a solution. 22.2 g of sodium bicarbonate (264.3 mmol) was added to the solution to produce a mixture. The mixture was cooled to 10° C. and was added slowly with 26.57 g of potassium permanganate (168.2 mmol) and 100 mL of water at a temperature below 15° C. After that, the reaction was stirred at 10° C. for 12 hours. After the reaction, the resulting product was added with 800 mL of ethyl acetate to produce a blend. The blend was stirred at room temperature for 1 hour and then dripped slowly with a freshly-prepared sodium bisulfite solution (prepared by dissolving 24.03 g of sodium bisulfate in 400 mL of water) at a temperature below 30° C. The reaction was stirred for 1 hour and then was stood for liquid separation to obtain an organic and an aqueous phase. The aqueous phase was stripped with 400 mL of ethyl acetate. The organic phases were combined, and the combined organic phase was washed with a 10% saline three times each of 200 mL and dried with rotary evaporation to produce a residue. The residue was mixed uniformly with 400 mL of isopropanol to produce a mixed solution. The mixed solution was dripped slowly with 400 mL of water at room temperature and a large amount of precipitates were formed to produce a turbid liquid. The turbid liquid was filtered to obtain a filter cake. The filter cake was washed with 200 mL of a solution of isopropanol and water at a ratio of 1:1 and dried to obtain 37.2 g of a white solid product with a yield of 83%. MS-ESI: m/z, 510 [M+1]$^+$.

Step (3) Synthesis of Compound PA6032-3

480 mg of compound PA6032-2 (0.946 mmol) was dissolved in 10 mL of toluene to produce a solution. 342 mg of diphenylmethanimine (1.892 mmol), 43 mg of Pd$_2$(dba)$_3$ (0.047 mmol), 89 mg of BINAP (0.142 mmol) and 272 mg of sodium tert-butoxide (2.84 mmol) were added to the solution. The reaction was stirred under nitrogen protection at 100° C. overnight. The resulting product was cooled to room temperature and added with 100 mL of water to produce a mixture. The mixture was extracted with DCM three times each of 150 mL. The organic phases were collected and combined. The combined organic phase was washed with a saturated saline, dried with anhydrous Na$_2$SO$_4$ and desolventized under vacuum to produce a residue. The residue was separated and purified using silica gel column chromatography with an eluent prepared by PE and DCM at a volume ratio of 1:1 to obtain 600 mg of a yellow solid product with a yield of 89%.

Step (4) Synthesis of Compound PA6032-4

500 mg of compound PA6032-3 (0.705 mmol) was dissolved in 5 mL of THF to produce a solution. 6 N hydrochloric acid was dripped into the solution to start a reaction and at a rate of two drops per hour. The reaction was carried out for 12 hours and the progress thereof was monitored at any time. After the reaction, a light yellow solid product was precipitated in the resulting product and obtained with a filtration. The light yellow solid product was washed with THF and dried under vacuum to obtain 240 mg of a final light yellow solid product with a yield of 75%.

Step (5) Synthesis of Compound PA6032-5

230 mg of compound PA6032-4 (0.507 mmol) was dissolved in 5 mL of DCM to produce a solution. 281 mg of t-butoxycarbonyl-L-proline (1.117 mmol), 579 mg of HATU (1.523 mmol) and 393 mg of DIPEA (3.046 mmol) were added to the solution. The reaction was stirred at room temperature overnight. After the reaction, the resulting product was added with 50 mL of water to produce a mixture. The mixture was extracted with DCM three times each of 100 mL. The organic phases were collected and combined. The combined organic phase was washed with a saturated saline, dried with anhydrous Na$_2$SO$_4$ and desolventized under vacuum to produce a residue. The residue was separated and purified using silica gel column chromatography with an eluent prepared by PE and EA at a volume ratio of 1:1 to obtain 380 mg of a yellow solid product with a yield of 97%.

Step (6) Synthesis of Compound PA6032-6

380 mg of compound PA6032-5 (0.490 mmol) was dissolved in 3 mL of an EA solution containing 3 M HCl. The reaction was stirred at room temperature overnight and a solid product was precipitated. When the reaction was confirmed to be completed through LC-MS monitoring, the resulting product was filtered to obtain 210 mg of a light yellow solid crude product, which was directly employed in the next reaction.

Step (7) Synthesis of Compound PA6032

80 mg of the crude product of compound PA6032-6 was dissolved in 10 mL of DCM to produce a solution. 113 mg of N-methoxycarbonyl-L-valine (0.649 mmol), 369 mg of HATU (0.972 mmol) and 250 mg of DIPEA (1.944 mmol) were added to the solution. The reaction was stirred at room temperature overnight. After the reaction, the resulting product was added with 50 mL of water to produce a mixture. The mixture was extracted with DCM three times each of 100 mL. The organic phases were collected and combined. The combined organic phase was washed with a saturated saline, dried with anhydrous Na$_2$SO$_4$ and desolventized under vacuum to produce a residue. The residue was separated and purified using silica gel column chromatography with an eluent prepared by PE and EA at a volume ratio of 1:3 to obtain 110 mg of a white solid product with a yield of 36%.

TABLE 1

| Number | Structure | Molecular weight |
|---|---|---|
| PA6001 | 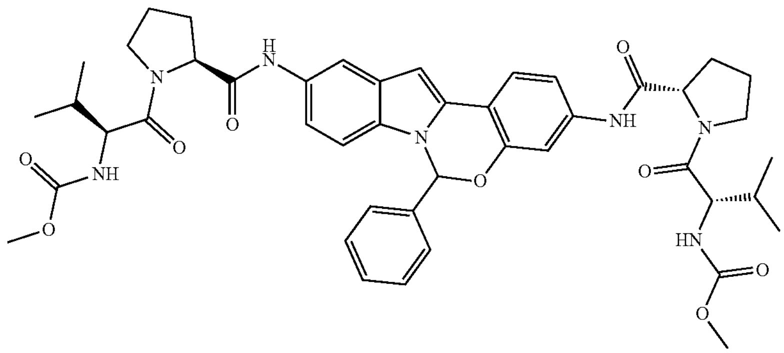 [SMILES: COC(=O)N[C@H](C(=O)N1CCC[C@H]1C(=O)Nc1ccc2c(c1)OC(c1ccccc1)n1c-2cc2cc(NC(=O)[C@@H]3CCCN3C(=O)[C@@H](NC(=O)OC)C(C)C)ccc21)C(C)C] | 835.94 |
| PA6001-A | 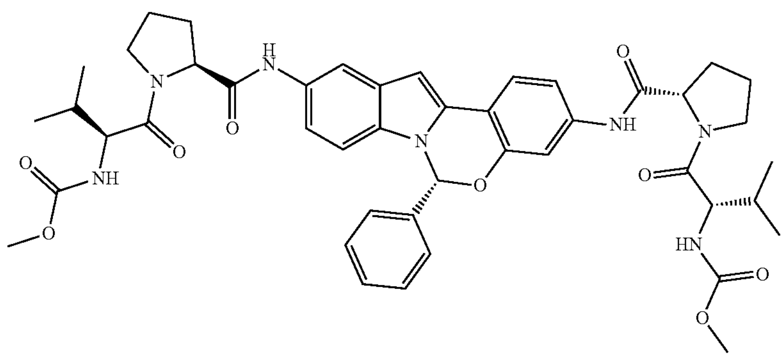 [SMILES: COC(=O)N[C@H](C(=O)N1CCC[C@H]1C(=O)Nc1ccc2c(c1)O[C@H](c1ccccc1)n1c-2cc2cc(NC(=O)[C@@H]3CCCN3C(=O)[C@@H](NC(=O)OC)C(C)C)ccc21)C(C)C] | 835.94 |
| PA6001-B | 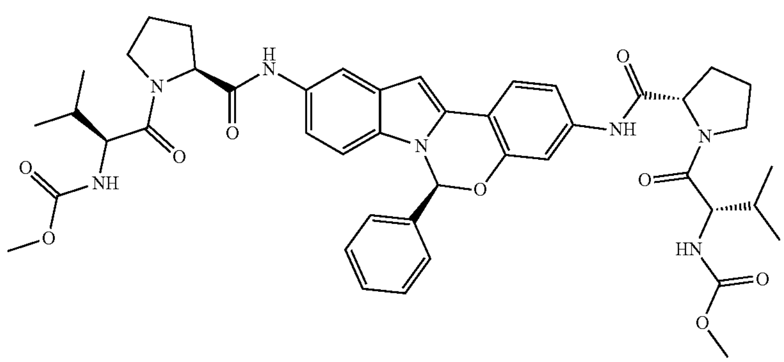 [SMILES: COC(=O)N[C@H](C(=O)N1CCC[C@H]1C(=O)Nc1ccc2c(c1)O[C@@H](c1ccccc1)n1c-2cc2cc(NC(=O)[C@@H]3CCCN3C(=O)[C@@H](NC(=O)OC)C(C)C)ccc21)C(C)C] | 835.94 |
| PA6002 | 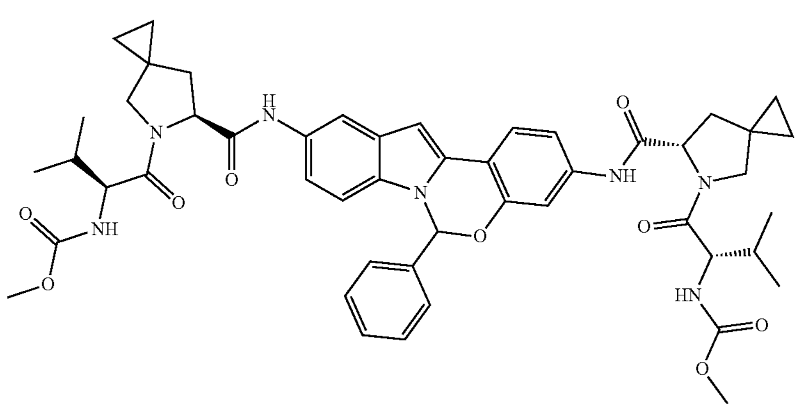 [SMILES: COC(=O)N[C@H](C(=O)N1CC2(CC2)C[C@H]1C(=O)Nc1ccc2c(c1)OC(c1ccccc1)n1c-2cc2cc(NC(=O)[C@@H]3CC4(CC4)CN3C(=O)[C@@H](NC(=O)OC)C(C)C)ccc21)C(C)C] | 888.02 |

TABLE 1-continued

Compounds: number, structure and molecular weight

| Number | Structure | Molecular weight |
|---|---|---|
| PA6010 | 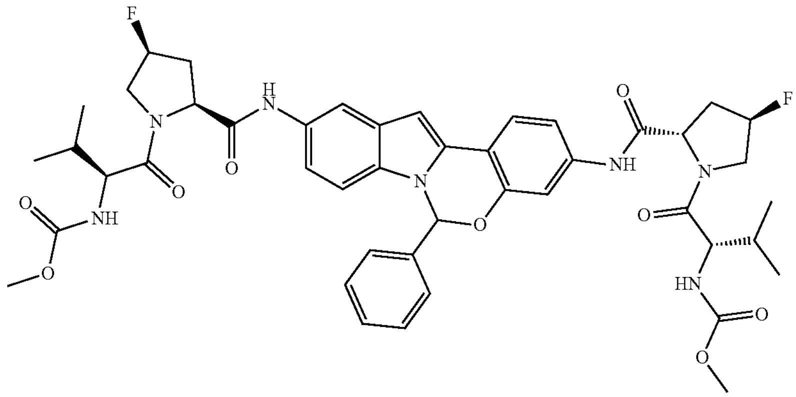 [SMILES: COC(=O)N[C@H](C(=O)N1C[C@H](F)C[C@H]1C(=O)Nc1ccc2c(c1)OC(c1ccccc1)n1c-2cc2cc(NC(=O)[C@@H]3C[C@H](F)CN3C(=O)[C@@H](NC(=O)OC)C(C)C)ccc21)C(C)C] | 871.92 |
| PA6011 | 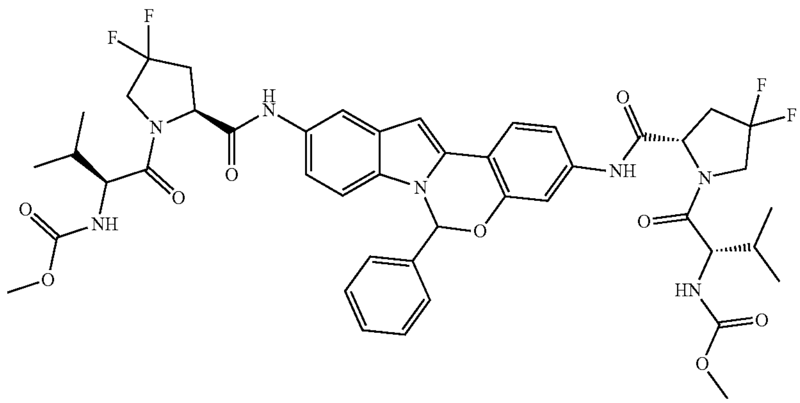 [SMILES: COC(=O)N[C@H](C(=O)N1CC(F)(F)C[C@H]1C(=O)Nc1ccc2c(c1)OC(c1ccccc1)n1c-2cc2cc(NC(=O)[C@@H]3CC(F)(F)CN3C(=O)[C@@H](NC(=O)OC)C(C)C)ccc21)C(C)C] | 907.91 |
| PA6016 | 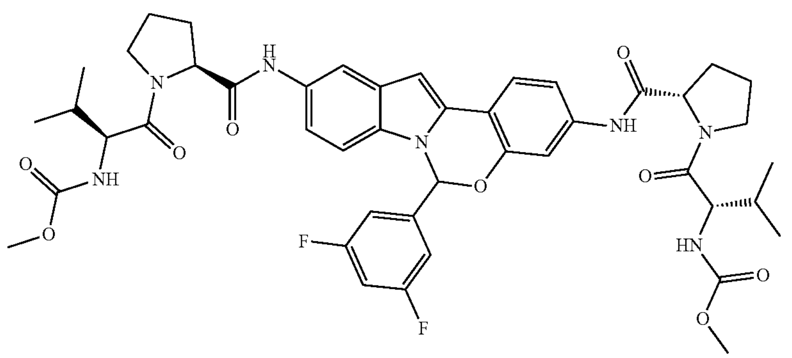 [SMILES: COC(=O)N[C@H](C(=O)N1CCC[C@H]1C(=O)Nc1ccc2c(c1)OC(c1cc(F)cc(F)c1)n1c-2cc2cc(NC(=O)[C@@H]3CCCN3C(=O)[C@@H](NC(=O)OC)C(C)C)ccc21)C(C)C] | 871.92 |
| PA6017 | 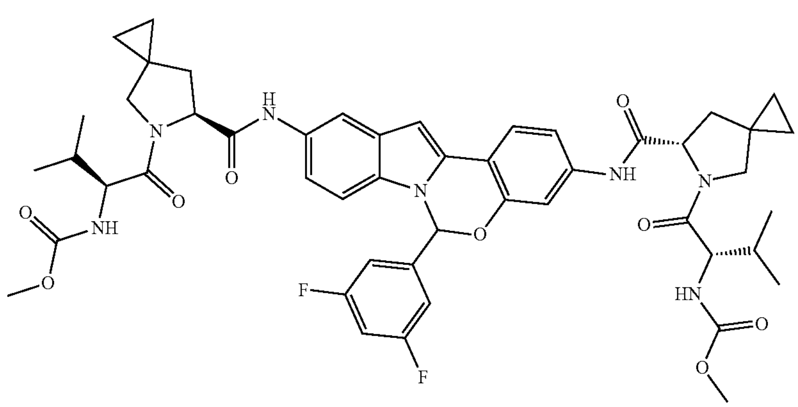 [SMILES: COC(=O)N[C@H](C(=O)N1CC2(CC2)C[C@H]1C(=O)Nc1ccc2c(c1)OC(c1cc(F)cc(F)c1)n1c-2cc2cc(NC(=O)[C@@H]3CC4(CC4)CN3C(=O)[C@@H](NC(=O)OC)C(C)C)ccc21)C(C)C] | 924.00 |

TABLE 1-continued

Compounds: number, structure and molecular weight

| Number | Structure | Molecular weight |
|---|---|---|
| PA6018 | 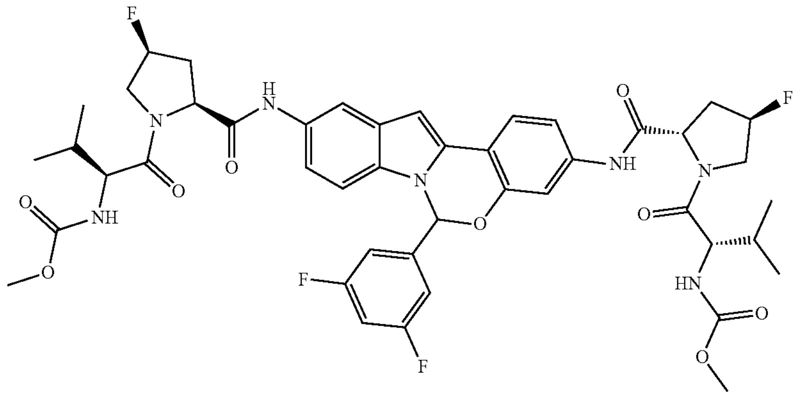 [SMILES: COC(=O)N[C@H](C(=O)N1C[C@H](F)C[C@H]1C(=O)Nc1ccc2c(c1)OC(c1cc(F)cc(F)c1)n1c-2cc2cc(NC(=O)[C@@H]3C[C@H](F)CN3C(=O)[C@@H](NC(=O)OC)C(C)C)ccc21)C(C)C] | 907.91 |
| PA6019 | 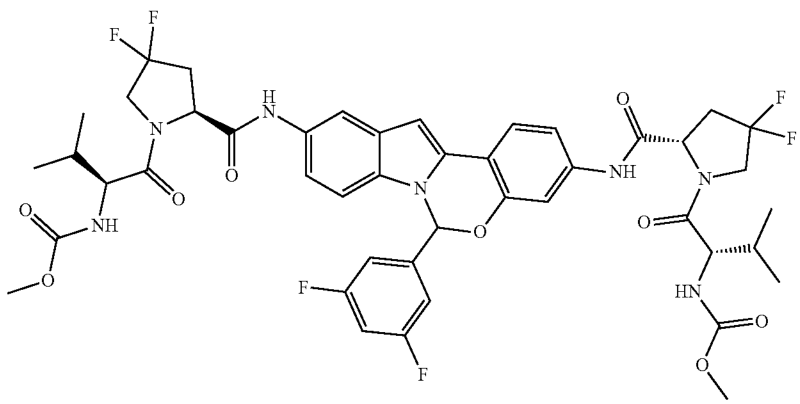 [SMILES: COC(=O)N[C@H](C(=O)N1CC(F)(F)C[C@H]1C(=O)Nc1ccc2c(c1)OC(c1cc(F)cc(F)c1)n1c-2cc2cc(NC(=O)[C@@H]3CC(F)(F)CN3C(=O)[C@@H](NC(=O)OC)C(C)C)ccc21)C(C)C] | 943.89 |
| PA6016-B | 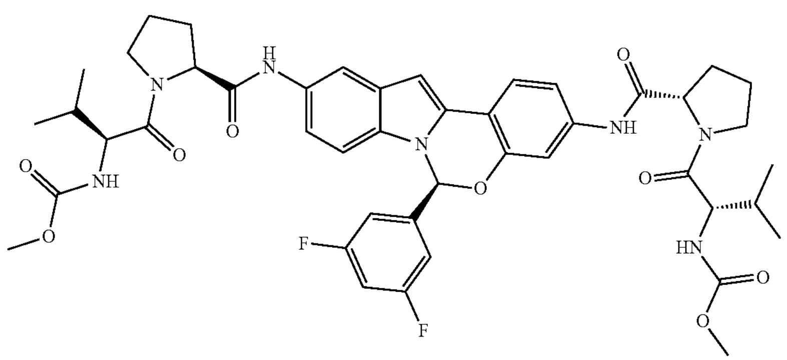 [SMILES: COC(=O)N[C@H](C(=O)N1CCC[C@H]1C(=O)Nc1ccc2c(c1)O[C@@H](c1cc(F)cc(F)c1)n1c-2cc2cc(NC(=O)[C@@H]3CCCN3C(=O)[C@@H](NC(=O)OC)C(C)C)ccc21)C(C)C] | 871.92 |
| PA6030 | 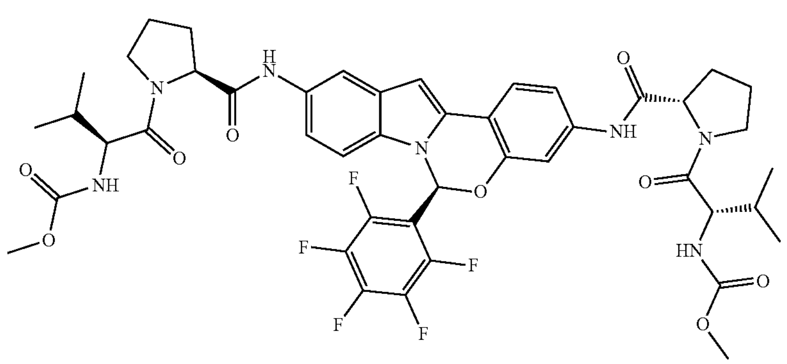 [SMILES: COC(=O)N[C@H](C(=O)N1CCC[C@H]1C(=O)Nc1ccc2c(c1)O[C@@H](c1c(F)c(F)c(F)c(F)c1F)n1c-2cc2cc(NC(=O)[C@@H]3CCCN3C(=O)[C@@H](NC(=O)OC)C(C)C)ccc21)C(C)C] | 925.90 |

TABLE 1-continued

Compounds: number, structure and molecular weight

| Number | Structure | Molecular weight |
|---|---|---|
| PA6031 | 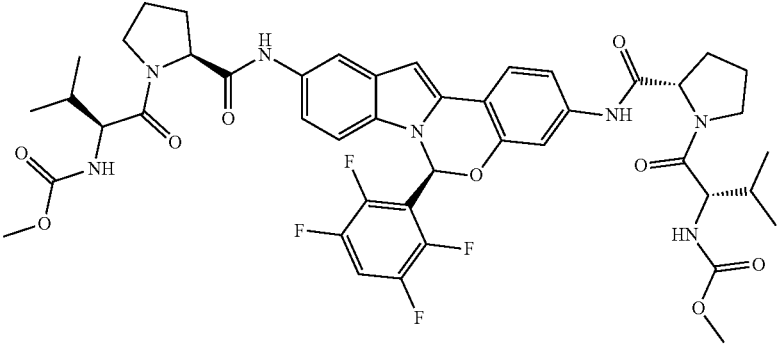 [SMILES: COC(=O)N[C@H](C(=O)N1CCC[C@H]1C(=O)Nc1ccc2c(c1)O[C@@H](c1c(F)c(F)cc(F)c1F)n1c-2cc2cc(NC(=O)[C@@H]3CCCN3C(=O)[C@@H](NC(=O)OC)C(C)C)ccc21)C(C)C] | 907.91 |
| PA6032 | 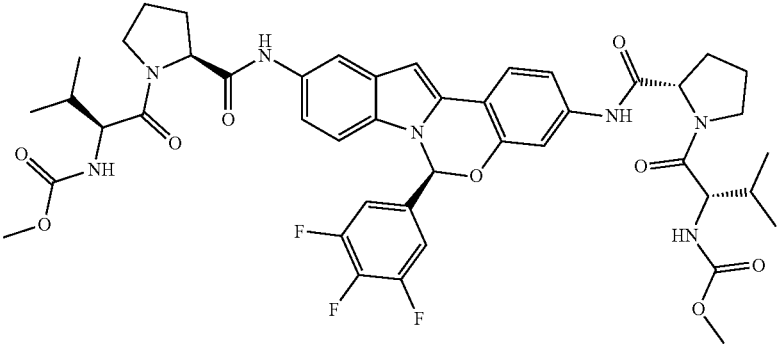 [SMILES: COC(=O)N[C@H](C(=O)N1CCC[C@H]1C(=O)Nc1ccc2c(c1)O[C@@H](c1cc(F)c(F)c(F)c1)n1c-2cc2cc(NC(=O)[C@@H]3CCCN3C(=O)[C@@H](NC(=O)OC)C(C)C)ccc21)C(C)C] | 889.92 |

TABLE 2

Compounds: Number and NMR data

| Number | NMR data |
|---|---|
| PA6001 | $^1$H NMR (400 MHz, DMSO-d$_6$): δ: 10.195(s, 1H), 9.912(s, 1H), 7.999(d, J = 1.6 Hz, 1H), 7.730(d, J = 8.4 Hz, 1H), 7.676(s, 1H), 7.516(d, J = 2.0 Hz, 1H), 7.358(s, 1H), 7.337(s, 1H) 7.239-7.281(m, 4H), 7.123-7.188(m, 2H), 6.975(s, 1H), 6.869-6.892(m, 2H), 4.458-4.491(m, 1H), 4.386-4.418(m, 1H), 4.038(q, J = 8.4 Hz, 2H), 3.781-3.837 (m, 2H), 3.637-3.680(m, 2H), 3.535(s, 3H), 3.525(s, 3H), 1.836-2.189(m, 10H), 0.954(t, J = 7.6 Hz, 6H), 0.894(t, J = 5.6 Hz, 6H) ppm. |
| PA6001-A | $^1$H NMR (400 MHz, CDCl$_3$): δ: 9.773(s, 1H), 9.683(s, 1H), 8.114(s, 1H), 7.616(s, 1H), 7.083-7.145(m, 4H), 7.006(d, J = 8.0 Hz, 1H), 6.863(s, 1H), 6.846(s, 1H), 6.678(d, J = 8.8 Hz, 1H), 6.508(d, J = 8.8 Hz, 1H), 6.318(s, 1H), 6.171(d, J = 7.6 Hz, 1H), 5.286-5.343(m, 2H), 4.692-4.773(m, 2H), 4.391-4.451(m, 2H), 3.773-3.903(m, 4H), 3.704 (s, 3H), 3.698(s, 3H), 1.976-2.305(m, 10H), 1.178(d, J = 6.4 Hz, 3H), 1.120(d, J = 6.4 Hz, 3H), 1.064(d, J = 6.4 Hz, 3H), 1.017(d, J = 6.4 Hz, 3H) ppm. |
| PA6001-B | $^1$H NMR (400 MHz, CDCl$_3$): δ: 9.576(s, 1H), 9.316(s, 1H), 7.741(s, 1H), 7.390(d, J = 8.4 Hz, 1H), 7.280-7.306(m, 3H), 7.219-7.244(m, 2H), 6.965-7.096(m, 4H), 6.581(s, 1H), 6.506(d, J = 8.8 Hz, 1H), 5.341-5.417(m, 2H), 4.743-4.817(m, 2H), 4.333-4.389 (m, 2H), 3.790-3.826(m, 2H), 3.639-3.690(m, 8H), 2.430-2.481(m, 2H), 1.931-2.253 (m, 8H), 1.005(t, J = 6.4 Hz, 6H), 0.940-0.967(m, 6H) ppm. |
| PA6002 | $^1$H NMR (400 MHz, CDCl$_3$): δ: 8.931-9.320(m, 2H), 7.869-8.039(m, 1H), 7.490-7.543(m, 1H), 7.252-7.324(m, 2H), 7.020-7.220(m, 5H), 6.938-6.980(m, 1H), 6.685-6.784(m, 2H), 6.535(s, 1H), 5.274-5.435(m, 4H), 4.895-4.999(m, 2H), 3.893-4.307 (m, 6H), 3.707(s, 6H), 2.791-3.111(m, 2H), 2.032-2.369(m, 4H), 1.006-1.153(m, 12H) ppm. |
| PA6010 | $^1$H NMR (400 MHz, CDCl$_3$): δ: 8.931-9.320(m, 2H), 7.869-8.039(m, 1H), 7.490-7.543(m, 1H), 7.252-7.324(m, 2H), 7.020-7.220(m, 5H), 6.938-6.980(m, 1H), 6.685-6.784(m, 2H), 6.535(s, 1H), 5.274-5.435(m, 4H), 4.895-4.999(m, 2H), 3.893-4.307 (m, 6H), 3.707(s, 6H), 2.791-3.111(m, 2H), 2.032-2.369(m, 4H), 1.006-1.153(m, 12H) ppm. |
| PA6011 | $^1$H NMR (400 MHz, CDCl$_3$): δ: 9.318-9.659(m, 2H), 7.301-7.706(m, 3H), 7.055-7.239(m, 4H), 6.712-7.020(m, 3H), 6.327-6.574(m, 2H), 6.075-6.095(m, 1H), 5.204-5.263(m, 2H), 4.806-4.889(m, 2H), 4.015-4.439(m, 6H), 3.726(s, 6H), 2.546-2.829 (m, 4H), 2.030-2.153(m, 2H), 0.849-1.197(m, 12H) ppm. |
| PA6016 | $^1$H NMR (400 MHz, CDCl$_3$): δ: 9.495-9.932(m, 2H), 7.465-7.802(m, 1H), 7.292-7.347(m, 1H), 7.180-7.247(m, 1H), 6.930-7.020(m, 2H), 6.619-6.742(m, 2H), 6.448- |

TABLE 2-continued

Compounds: Number and NMR data

| Number | NMR data |
|---|---|
| | 6.581(m, 3H), 6.294-6.328(m, 1H), 5.300-5.419(m, 2H), 4.705-4.835(m, 2H), 4.367-4.468(m, 2H), 3.730-3.927(m, 4H), 3.709(s, 6H), 1.959-2.431(m, 10H), 0.978-1.077 (m, 12H) ppm. |
| PA6017 | $^1$H NMR (400 MHz, CDCl$_3$): δ: 9.447-9.861(m, 2H), 7.760-8.267(m, 1H), 7.305-7.544(m, 1H), 7.204-7.266(m, 1H), 6.935-7.021(m, 2H), 6.469-6.757(m, 4H), 6.182-6.354(m, 2H), 5.252-5.412(m, 2H), 4.862-4.983(m, 2H), 4.290-4.372(m, 2H), 3.733-3.880(m, 3H), 3.709(s, 3H), 3.700(s, 3H), 3.559-3.653(m, 1H), 1.989-2.348(m, 6H), 0.984-1.189(m, 12H), 0.593-0.883(m, 8H) ppm. |
| PA6018 | $^1$H NMR (400 MHz, CDCl$_3$): δ: 8.980-9.447(m, 2H), 7.822-8.109(m, 1H), 7.462-7.608(m, 1H), 7.020-7.179(m, 3H), 6.579-6.917(m, 3H), 6.365-6.501(m, 3H), 5.272-5.456(m, 4H), 4.880-5.021(m, 2H), 3.915-4.348(m, 6H), 3.712(s, 6H), 2.007-2.411 (m, 6H), 1.015-1.187(m, 12H) ppm. |
| PA6019 | $^1$H NMR (400 MHz, CDCl$_3$): δ: 9.372-9.771(m, 2H), 7.543-8.296(m, 1H), 7.153-7.272(m, 2H), 6.712-7.021(m, 3H), 6.436-6.648(m, 3H), 6.099-6.342(m, 2H), 5.170-5.262(m, 2H), 4.812-4.956(m, 2H), 4.367-4.446(m, 2H), 4.038-4.320(m, 4H), 3.731 (s, 6H), 2.580-2.883(m, 4H), 2.009-2.263(m, 2H), 0.994-1.216(m, 12H) ppm. |
| PA6016-B | $^1$H NMR (400 MHz, CDCl$_3$): δ: 9.645(s, 1H), 9.402(s, 1H), 7.784(s, 1H), 7.424-7.445(m, 1H), 7.020-7.266(m, 4H), 6.688-6.829(m, 2H), 6.620(s, 1H), 6.511-6.525 (m, 2H), 5.325-5.437(m, 2H), 4.779-4.887(m, 2H), 4.356-4.413(m, 2H), 3.752-3.847(m, 2H), 3.712(s, 6H), 3.644-3.663(m, 2H), 2.224-2.263(m, 2H), 2.035-2.130 (m, 8H), 0.963-1.043(m, 12H) ppm. |
| PA6030 | $^1$H NMR (400 MHz, CDCl$_3$): δ: 9.809(s, 1H), 9.469(s, 1H), 7.524(s, 1H), 7.249-7.271 (m, 2H), 7.171(s, 1H), 7.005-7.024(s, 2H), 6.374(s, 1H), 6.299(d, J = 8.8 Hz, 1H), 5.348-5.410(m, 2H), 4.692-4.784(m, 2H), 4.369-4.423(m, 2H), 3.747-3.876(m, 4H), 3.704(s, 6H), 2.008-2.307(m, 10H), 1.076(s, 3H), 1.061(s, 3H), 0.999(s, 3H), 0.984 (s, 3H) ppm. |
| PA6031 | $^1$H NMR (400 MHz, CDCl$_3$): δ: 9.751(s, 1H), 9.405(s, 1H), 7.511-7.594(m, 1H), 7.302-7.361(m, 2H), 7.149-7.267(m, 2H), 6.999-7.020(m, 2H), 6.382-6.472(m, 2H), 5.367-5.418(m, 2H), 4.718-4.789(m, 2H), 4.360-4.411(m, 2H), 3.732-3.881(m, 4H), 3.703(s, 6H), 2.200-2.260(m, 2H), 2.009-2.102(m, 8H), 1.055(s, 3H), 1.038(s, 3H), 0.988(s, 3H), 0.971(s, 3H) ppm. |
| PA6032 | $^1$H NMR (400 MHz, CDCl$_3$): δ: 9.731(s, 1H), 9.497(s, 1H), 7.655(s, 1H), 7.328(d, J = 8.4 Hz, 1H), 7.228(d, J = 8.4 Hz, 1H), 7.164(d, J = 8.4 Hz, 1H), 7.105(s, 1H), 6.937(s, 1H), 6.715(d, J = 8.8 Hz, 1H), 6.598(t, J = 7.2, 2H), 6.482(s, 1H), 5.362-5.452(m, 2H), 4.749-4.846(m, 2H), 4.373-4.426(m, 2H), 3.813-3.896(m, 2H), 3.738-3.769(m, 2H), 3.712(s, 6H), 1.984-2.473(m, 10H), 0.987-1.092(m, 12H) ppm. |

Experimental Example 14 In-Vitro Evaluation

Objective

The HCV Replicon System was employed as an evaluation model to demonstrate the effect of the compound described herein on HCV. The HCV replicon was first reported in Science. 1999 Jul. 2; 285 (5424), 110-3. The HCV replicon system has been one of the most important tools to investigate the RNA replication, pathogenicity and virus persistence of HCV. For example, the replicon has been successfully used to verify the 5'-NCR minimum region essential for HCV RNA replication, in addition, the HCV replicon system has been successfully used as an evaluation model for antiviral drugs.

The demonstration was achieved according to the method described in Science. 1999-07-02; 285(5424), 110-3 and J. Virol. 2003-03; 77(5), 3007-19.

In brief, three stably-transfected cell lines containing different HCV genotypes of replicons were used to test activity of the compounds in inhibiting the HCV replication.

A Huh7-Con1b cell line contained an HCV 1b-genotype replicon Con1b and a reporter gene of firefly luciferase. An Huh7-H77 and an Huh7-JFH1 cell line both contained a reporter gene of renilla luciferase and respectively contained an HCV 1a-genotype replicon H77 and an HCV 2a-genotype replicon JFH1. The replication level of HCV in host cells can be characterized by the expression of the firefly luciferase gene or the renilla luciferase gene. The effect of the compounds described herein on the HCV replication can be evaluated through a chemiluminescence detection of the expression of the above two luciferase genes. Meanwhile, the CC50 value of each Huh7 cell line was measured using a CellTiter GLO kit to evaluate the toxicity of the compounds.

Operation

1. Determination of EC$_{50}$ of Compound Based on Luciferase Activity

The compounds described herein were subjected to three-fold serial dilutions using a Bravo liquid treatment system to obtain a total of 11 concentration points prior to cell plating. The prepared compounds were added to cell culture plates using an Echo 550 system. The Huh7-H77 and the Huh7-JFH1 cells were inoculated into the 96-well plate added with the compounds at an amount of 10000 cells per well. The Huh7-Con1b and the Huh7 cells were inoculated into the 384-well plate added with the compounds at an amount of 5000 cells per well. The cell culture plates were incubated in a CO$_2$ incubator (5%) at 37° C. for 72 hours.

1.1 Reading of the Reporter Gene of Firefly Luciferase

The 384-well plate was taken out of the incubator and cooled at room temperature for 30 minutes. After removing the medium, each well was added with 50 μL of DPBS (Dulbecco's Phosphate Buffered Saline) and then added with 50 μL of a Britelit plus reagent (PerkinElmer Inc.). Then the 384-well plate was placed in a shaker at a shaking rate of 1000 rpm at room temperature for 1 minute. Finally, the 384-well plate was read using an Envision Plate Reader at a signal accumulation time of per well of 0.1 s.

1.2 Reading of the Reporter Gene of Renilla Luciferase

The 96-well plate was taken out of the incubator and cooled at room temperature for 30 minutes. After removing the medium, each well was added with 30 μL of a diluted Promega lysate (diluted using pure water in a volume ratio of 1:4). The 96-well plate was placed in a shaker at a shaking rate of 1000 rpm at room temperature for 15 minutes. Each well was added with 100 μL of a diluted Premega luciferase reagent (Promega Inc.) (diluted using a substrate buffer in a volume ratio of 1:99) and then, the 96-well plate was immediately read using an Envision Plate Reader at a signal accumulation time of per well of 0.1 s.

2. Determination of $CC_{50}$ Value Using a CellTiter-GLO Kit

The CellTiter-GLO reagent was heated to room temperature. The 384-well plate plated with the Huh 7 cells was transferred from the incubator and cooled at room temperature for 20 minutes. Each well was added with 50 μL of the CellTiter-GLO reagent (Promega Inc.), and then the 384-well plate was shaken for 2 minutes. The 384-well plate was subsequently incubated in a dark environment at room temperature for 10 minutes. After the incubation, the 384-well plate was read using an Envision Plate Reader at a signal accumulation time of per well of 0.1 s.

The results were shown in Table 3.

TABLE 3

Test results of EC50/CC50 of the compounds for HCV replicon cell

| Compounds | HCV-1b replicon | | HCV-1a replicon | | HCV-2a replicon | |
|---|---|---|---|---|---|---|
| | $EC_{50}$(pM) | $CC_{50}$/nM | $EC_{50}$(pM) | $CC_{50}$/nM | $EC_{50}$(pM) | $CC_{50}$/nM |
| PA6001 | 20 | >100 | 1566 | >100 | 59 | >100 |
| PA6001-A | 8.14 | >100 | 2940 | >100 | 54.61 | >100 |
| PA6001-B | 6.8 | >100 | 59.34 | >100 | 62.65 | >100 |
| PA6002 | 5 | >100 | 30 | >100 | 148 | >100 |
| PA6010 | 4.495 | >100 | 106.7 | >100 | 199.55 | >100 |
| PA6011 | 1.18 | >100 | 47.555 | >100 | 312.4 | >100 |
| PA6016 | 3.65 | >100 | 43.29 | >100 | 49.945 | >100 |
| PA6017 | 2.36 | >100 | 26.835 | >100 | 743.35 | >100 |
| PA6018 | 2.95 | >100 | 35.105 | >100 | 101.62 | >100 |
| PA6019 | 0.88 | >100 | 53.435 | >100 | 233.8 | >100 |
| PA6016-B | 4.3405 | >100 | 18.045 | >100 | 61.49 | >100 |
| PA6030 | 3.1475 | >100 | 76.26 | >100 | 206.7 | >100 |
| PA6031 | 2.2995 | >100 | 36.925 | >100 | 40.1 | >100 |
| PA6032 | 3.0395 | >100 | 16.815 | >100 | 147.3 | >100 |

Notes:
EC50 indicates an activity of the compound against hepatitis C virus (HCV) in vitro, and an $EC_{50}$ value of less than 1 uM means that the compound has an activity in vitro; and the $CC_{50}$ value can be used to evaluate a toxicity of the compound in vitro, and a greater value indicates a smaller toxicity.

Conclusion

As the data showed that the compounds of the present invention had an excellent activity against hepatitis C virus (HCV) in vitro due to an EC50 value far below 1 μM and an extremely low cytotoxicity. Specifically, most compounds of the present invention had an $EC_{50}$ value of less than 10 pM for the HCV-1b replicon. For the HCV-2a replicon, the compounds had an $EC_{50}$ value up to the order of 100 pM and the compounds such as PA6031 and PA6016 even had an $EC_{50}$ value of only about 40-50 pM. Since Chinese hepatitis C patients were mainly infected with the HCV genotype 1b and 2a, the compounds of the present invention had broad application prospects as an NS5A inhibitor.

Experimental Example 15 Bioavailability

1. Dosage Regimen

Sprague Dawley rats, male, weighing 250-280 g, were randomly divided into two groups, each having three rats. The rats were subjected to a jugular vein cannulation 3 days before administration. The two groups of rats were administered with the compounds in an intragastric or intravenous route, respectively. The specific scheme was shown in Table 4.

TABLE 4

Administration and dosage of the compounds

| Groups | Number of rats | Compounds | Administration | Dosage (mg/kg) |
|---|---|---|---|---|
| 1 | 3 | PA6001-A | intragastric | 15 |
| 2 | 3 | PA6001-A | intravenous | 15 |
| 1 | 3 | PA6016-B | intragastric | 15 |
| 2 | 3 | PA6016-B | intravenous | 15 |
| 1 | 3 | PA6032 | intragastric | 15 |
| 2 | 3 | PA6032 | intravenous | 15 |
| 1 | 3 | PA6031 | intragastric | 15 |
| 2 | 3 | PA6031 | intravenous | 15 |
| 1 | 3 | PA6030 | intragastric | 15 |
| 2 | 3 | PA6030 | intravenous | 15 |

The rats were fasted for 12 hours before the test, but were free to drink water. The rats were uniformly fed 2 hours after administration. The solvent used to dissolve the compounds was a mixture of polyoxyethylene castor oil, ethanol, PEG and 0.9% NaCl at a ratio of 10:10:40:40.

2. Blood Collection Time and Sample Processing 0.2 mL of blood of the tested rats was respectively collected at 0.083, 0.25, 0.5, 1, 2, 4, 8, 12, and 24 hours after administration through a jugular vein cannulate, and then transferred to heparin anticoagulation tubes. The blood sample was immediately centrifuged at 3000 g for 5 minutes to obtain a plasma. The process from the blood collection to the centrifugation for obtaining plasma was carried out in an ice bath. The obtained plasma was stored at −80° C. for testing.

3. Sample Testing and Data Analysis

Concentrations of the original compounds in the plasma of the rats were determined using a LC-MS-MS method.

A non-compartment model of WinNonlin 6.1 softwear (Pharsight Inc. US) was employed to calculate pharmacokinetic parameters after administration.

Peak concentration $C_{max}$ and peak time $T_{max}$ are measured values.

Area under the drug level-time curve, that is, $AUC_{0-4}$ value, was calculated as the following equation using a trapezoidal method.

$$AUC_{0-\infty} = AUC_{0-t} + C_t/k_e$$

Wherein, $C_t$ was the drug concentration in the blood sample collected at the last measurable time point, and $k_e$ was an elimination rate constant.

Elimination half-life was calculated as $t_{1/2} = 0.693/k_e$.

Mean residence time was calculated as MRT=AUMC/AUC.

Clearance was calculated as $CL = D/AUC_{0-\infty}$.

Steady state distribution volume was calculated as $V_{ss} = CL \times MRT$.

Absolute bioavailability was calculated as $F = (AUC_{ingastric} \times D_{intravenous})/(AUC_{intravenous} \times D_{intragastric}) \times 100\%$.

4. Results

After the rats were administered with 15 mg/kg of the compounds in an intragastric or an intravenous manner, a relative bioavailability of 50-120% was obtained based on pharmacokinetic and physicochemical properties, and a commercially available drug ABT-267 (an NS5A inhibitor) had been reported in a literature to have a bioavailability of 100% in the rats. This demonstrated that the compounds of the present invention have excellent pharmacokinetic properties due to a similar or equivalent bioavailability to the commercially available drugs, All documents mentioned in the present application are hereby incorporated by reference as if each document is individually incorporated by reference. In addition, it should be understood that various modifications and changes may be made to the present invention without departing from the disclosure of the invention. These equivalents also fall within the scope defined by the appended claims.

What is claimed is:

1. A compound of formula (I-a)

wherein A and A' are independently where $R^{2a}$ and $R^{2b}$ are independently selected from the group consisting of hydrogen, fluorine, chlorine, bromine and iodine; or $R^{2a}$ and $R^{2b}$ are cyclized to form a $C_3$-$C_8$ cycloalkyl;

each $R_1$ is selected from the group consisting of fluorine, chlorine, bromine and iodine;

each $R_4$ is selected from the group consisting of fluorine, chlorine, bromine and iodine;

each $R_6$ is selected from the group consisting of fluorine, chlorine, bromine and iodine;

$R_2$ and $R_2'$ are independently selected from substituted or unsubstituted $C_1$-$C_6$ alkyl; where substitution is performed by one or more substituents selected from the group consisting of halogen, $C_1$-$C_3$ alkyl, $C_1$-$C_3$ haloalkyl, nitro, hydroxyl, amino and cyano group;

$R_3$ and $R_3'$ are independently selected from substituted or unsubstituted $C_1$-$C_6$ alkyl, where substitution is performed by one or more substituents selected from the group consisting of halogen, $C_1$-$C_3$ alkyl $C_1$-$C_3$ haloalkyl, nitro, hydroxyl, amino and cyano group; and $R_5$ is selected from the group consisting of hydrogen, fluorine, chlorine, bromine and iodine;

n is 2, 3, 4 or 5;

m is 0, 1, 2 or 3; and p is 0, 1, 2 or 3.

2. The compound of claim 1, wherein the compound is selected from the group consisting of

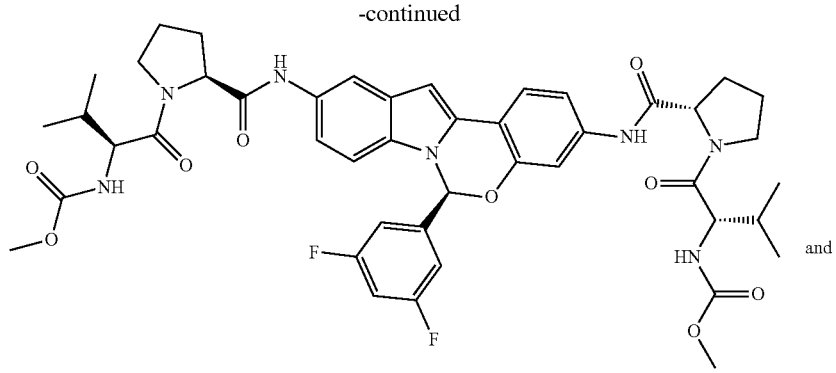

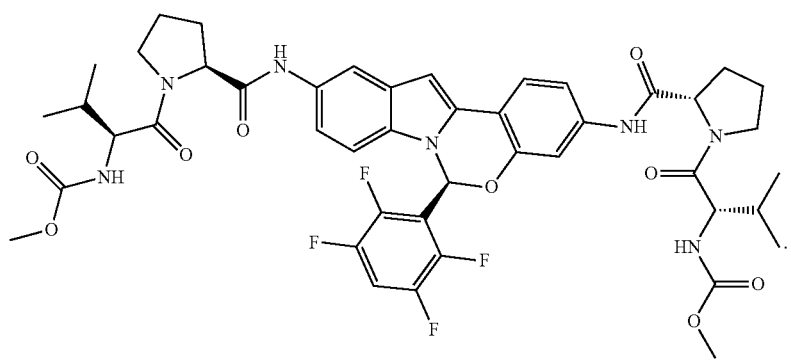

3. A pharmaceutical composition comprising the compound of claim 1 or an optical isomer, a pharmaceutically acceptable salt, a hydrate or a solvate thereof, and a pharmaceutically acceptable auxiliary, diluent or carrier.

4. The pharmaceutical composition of claim 3, further comprising at least one HCV inhibitor for inhibiting HCV replication process and/or function of HCV protein.

5. The pharmaceutical composition of claim 4, wherein the HCV replication process comprises HCV entry, HCV uncoating, HCV transcription, HCV replication, HCV assembly and/or HCV release.

6. The pharmaceutical composition of claim 4, wherein the HCV protein is selected from the group consisting of NS2, NS3, NS4A, NS4B, NS5A and NS5B.

7. A method of preparing the compound of claim 1, comprising:

(a) reacting compound 1 with diphenylmethanimine in an inert solvent to form compound 2

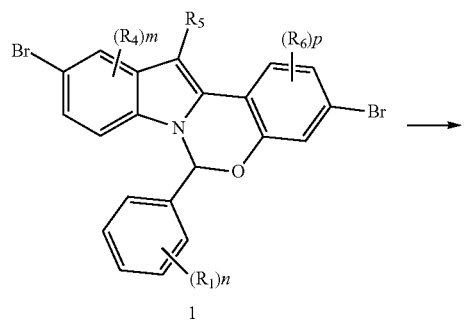

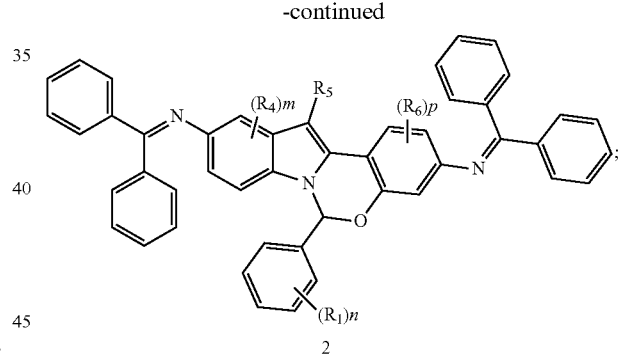

(b) reacting compound 2 with an acid in an inert solvent to form compound 3

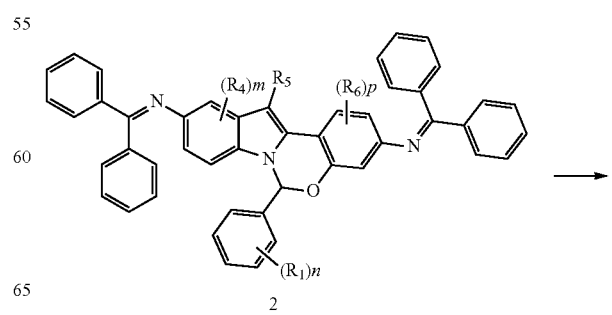

-continued
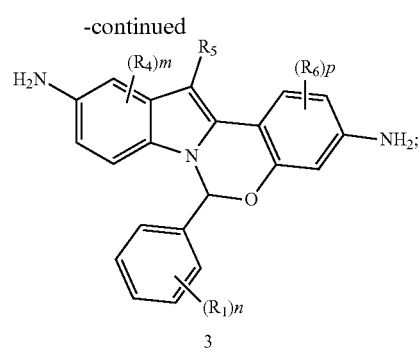
3
(c) reacting compound 3 with
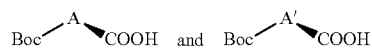
in an inert solvent to form compound 4
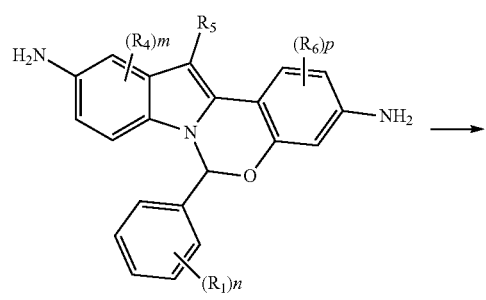
(d) reacting compound 4 with an acid in an inert solvent to form compound 5
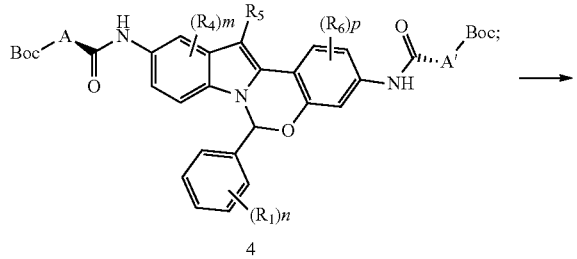
4
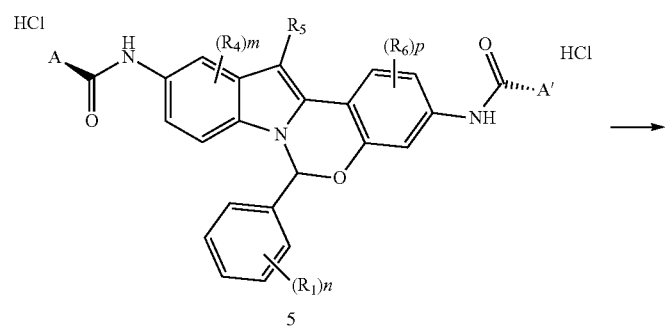
5
(e) reacting compound 5 with
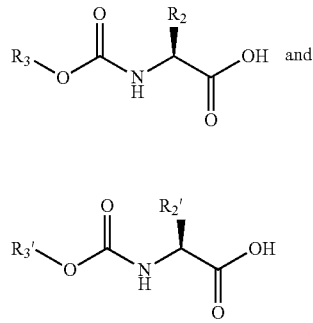
in an inert solvent to form the compound of formula (I)

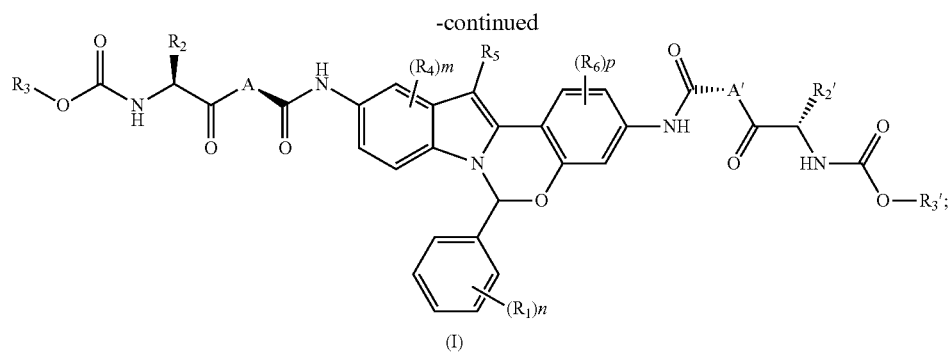
and
(f) subjecting the compound of formula (I) to chiral resolution to form the compound of formula (I-a);
wherein, A, A', $R_1$, n, $R_2$, $R_2'$, $R_3$, $R_3'$, $R_4$, m, $R_5$, $R_6$ and p are defined in the same manner as in claim 1.
* * * * *